(12) United States Patent
Jayyosi et al.

(10) Patent No.: US 6,376,512 B1
(45) Date of Patent: Apr. 23, 2002

(54) THERAPEUTIC USES OF QUINOLINE DERIVATIVES

(75) Inventors: Zaid Jayyosi, Collegeville; Gerard M. McGeehan, Chester Springs; Michael F. Kelley, West Chester, all of PA (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/490,897

(22) Filed: Jan. 27, 2000

Related U.S. Application Data

(63) Continuation of application No. PCT/US98/21947, filed on Oct. 16, 1998.
(60) Provisional application No. 60/062,318, filed on Oct. 17, 1997, and provisional application No. 60/065,902, filed on Nov. 17, 1997.

(51) Int. Cl.$^7$ .................. A61K 31/47; A61K 31/155
(52) U.S. Cl. .................. 514/311; 514/635; 514/824; 514/866; 514/884

(58) Field of Search .................. 514/311, 635, 514/824, 884, 866

(56) References Cited

U.S. PATENT DOCUMENTS 4,920,130 A * 4/1990 Huang et al. ............... 514/311

* cited by examiner

Primary Examiner—Kevin E. Weddington
(74) Attorney, Agent, or Firm—Finnegan, Henderson, Farabow, Garrett, & Dunner, LLP

(57) ABSTRACT

A method for mediating the activity of PPAR-γ receptor comprising contacting said PPAR-γ receptor with a compound of formula I defined herein. Also disclosed is the treatment of a patient suffering from a physiological disorder capable of being modulated by a compound of formula I having PPAR-γ ligand binding activity, comprising administering to the patient a pharmaceutically acceptable amount of the compound, or a pharmaceutically acceptable salt thereof.

18 Claims, 5 Drawing Sheets

THERAPEUTIC USES OF QUINOLINE DERIVATIVES

This application is a continuation of International Patent Application No. PCT/US98/21947, filed on Oct. 16, 1998, which is, in turn, a continuation-in-part of U.S. patent application Ser. No. 60/062,318, filed Oct. 17, 1997, and U.S. patent application Ser. No. 60/065,902, filed Nov. 17, 1997, both of which are now abandoned.

BACKGROUND OF THE INVENTION

This invention is directed to the use of quinolinyl phenyl compounds and their pharmaceutical compositions as PPAR-γ ligand receptor binders, wherein PPAR-γ ligand receptor binders of this invention are useful as agonists or antagonists of the PPAR-γ receptor.

FIELD OF THE INVENTION

Biological processes modulated by PPAR-γ are considered biological processes which are modulated by receptor, or receptor combinations, which are responsive to the PPAR-γ ligand receptor binders described herein. For example, cell differentiation to produce lipid accumulating cells, regulation of insulin sensitivity and blood glucose levels, which are involved in hypoglycemia/hyperinsulinism (resulting from for example, abnormal pancreatic beta cell function, insulin secreting tumors and/or autoimmune hypoglycemia due to autoantibodies to insulin, the insulin receptor, or autoantibodies that are stimulatory to pancreatic beta cells) and macrophage formation which lead to the formation of atherosclerotic plaques.

Two isoforms of PPAR-γ receptor have been identified, namely PPAR-γ1 and PPAR-γ2, and are shown to differ in their amino termini.

Obesity is an excessive accumulation of adipose tissue. Recent work in this area indicates that peroxisome proliferator activated receptor-γ (PPAR-γ) plays a central role in the adipocyte gene expression and differentiation. Excess adipose tissue is associated with the development of serious medical conditions, for example, non-insulin-dependent diabetes mellitus (NIDDM), hypertension, coronary artery disease, hyperlipidemia and certain malignancies. The adipocyte may also influence glucose homeostasis through the production of tumor necrosis factor α (TNFα) and other molecules. One of the earliest events in the differentiation of an adipocyte is the expression of the γ isoform of the PPAR-γ.

Non-insulin-dependent diabetes mellitus (NIDDM), or Phase II diabetes, is the most common form of diabetes, with 90–95% of the hyperglycemic patients experiencing this form of disease. In NIDDM there appears to be a reduction in the pancreatic β-cell mass, several distinct defects in insulin secretion and a decrease in tissue sensitivity to insulin. The symptoms of this form of diabetes include fatigue, frequent urination, thirst, weight loss, blurred vision, frequent infections and slow healing of sores, diabetic nerve damage and renal disease.

Resistance to the metabolic actions of insulin is one of the key features of non-insulin dependent diabetes (NIDDM). Insulin resistance is characterised by impaired uptake and utilization of glucose in insulin-sensitive target organs, for example, adipocytes and skeletal muscle, and by impaired inhibition of hepatic glucose output. The relative insulin deficiency and the failure of insulin to surpress hepatic glucose output results in fasting hyperglycemia. The β-cells in the liver try to compensate for the insulin resistance by secreting increased levels of insulin, however the β-cells are unable to maintain this high output of insulin and eventually the glucose-induced insulin secretion falls, leading to the deterioration of glucose homeostasis and to the subsequent development of overt diabetes.

Hyperinsulinemia is also linked to insulin resistance, hypertriglyceridaemia and increased plasma concentration of low density lipoproteins. The association of insulin resistance and hyperinsulinemia with these metabolic disorders has been termed "Syndrome X" and as been strongly linked to an increased risk of hypertension and coronary artery disease.

Metformin is known in the art to be used in the treatment of diabetes in humans (U.S. Pat. No. 3,174,901). Metformin acts primarily to decrease the patient's liver glucose production. Troglitazone is known to work primarily on enhancing the ability of the patient's muscle to respond to insulin and take up glucose. It is known that combination therapy comprising metformin and troglitazone can be used in the treatment of abnormalities associated with diabetes (Today's News Connection, AAAS EurekaAlert Press Releases, Mar. 26, 1996).

The present invention discloses a series of compounds for use in stimulating insulin sensitization and providing glycemic control, as well as a number of other pharmaceutical uses associated with it.

SUMMARY OF THE INVENTION

An object of this invention is the use of quinolinyl phenyl compounds and their pharmaceutical compositions as PPAR-γ ligand receptor binders, which are useful as agonists or antagonists of the PPAR-γ receptor.

The quinolinyl phenyl compounds for use according to the invention are of formula I

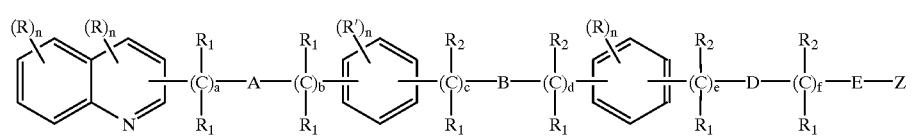

wherein:

A is O, S

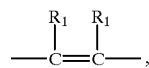

or a chemical bond;

B is O, S, SO, SO$_2$, NR$_1$, a chemical bond,

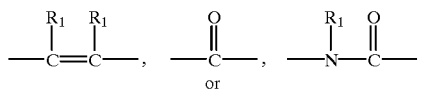

D is O, S, NR$_1$,

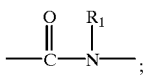

or a chemical bond;

E is a chemical bond or

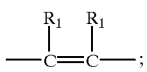

a is 0–2;
b is 0–1;
c is 0–4;
d is 0–5;
e is 0–4;
f is 0–5;
n is 0–2;
R is independently hydrogen, alkyl, hydroxy, alkoxy, carboxy, alkoxycarbonyl, halo, nitro, cyano or acyl;
R' is independently hydrogen, alkyl, hydroxy, alkoxy or halo;
R$_1$ is independently hydrogen, alkyl or aralkyl, or geminal R$_1$ and R$_1$ taken together with the carbon atom to which the geminal R$_1$ and R$_1$ are attached to form =CHR$_1$;
R$_2$ is —(CH$_2$)$_q$—X, or two vicinal R$_2$ taken together with the carbon atoms through which the two vicinal R$_2$ are linked form cycloalkylene, or geminal R$_1$ and R$_2$ taken together with the carbon atom to which the geminal R$_1$ and R$_2$ are attached form cycloalkylene, =CHR$_1$, or carbonyl;
q is 0–3;
X is hydrogen, alkyl, alkenyl, cycloalkyl, heterocyclyl, aryl, heteroaryl, aralkyl, heteroaralkyl, hydroxy, alkoxy, aralkoxy, heteroaralkoxy, carboxy, alkoxycarbonyl, tetrazolyl, acylHNSO$_2$—, Y$^1$Y$^2$N— or Y$^3$Y$^4$NCO—;
Y$^1$ and Y$^2$ are independently hydrogen, alkyl, aryl, aralkyl or heteroaralkyl, or one of Y$^1$ and Y$^2$ is hydrogen or alkyl and the other of Y$^1$ and Y$^2$ is acyl or aroyl;
Y$^3$ and Y$^4$ are hydrogen, alkyl, aryl, aralkyl or heteroaralkyl;
Z is R$_1$O$_2$C—, CN, halo, R$_3$O$_2$SHNCO—, (R$_1$)$_2$NCO—, R$_1$O— or tetrazolyl; and
R$_3$ is hydrogen, alkyl, phenyl or benzyl, or
a pharmaceutically acceptable salt thereof.

DETAILED DESCRIPTION OF THE INVENTION

Figure 1:
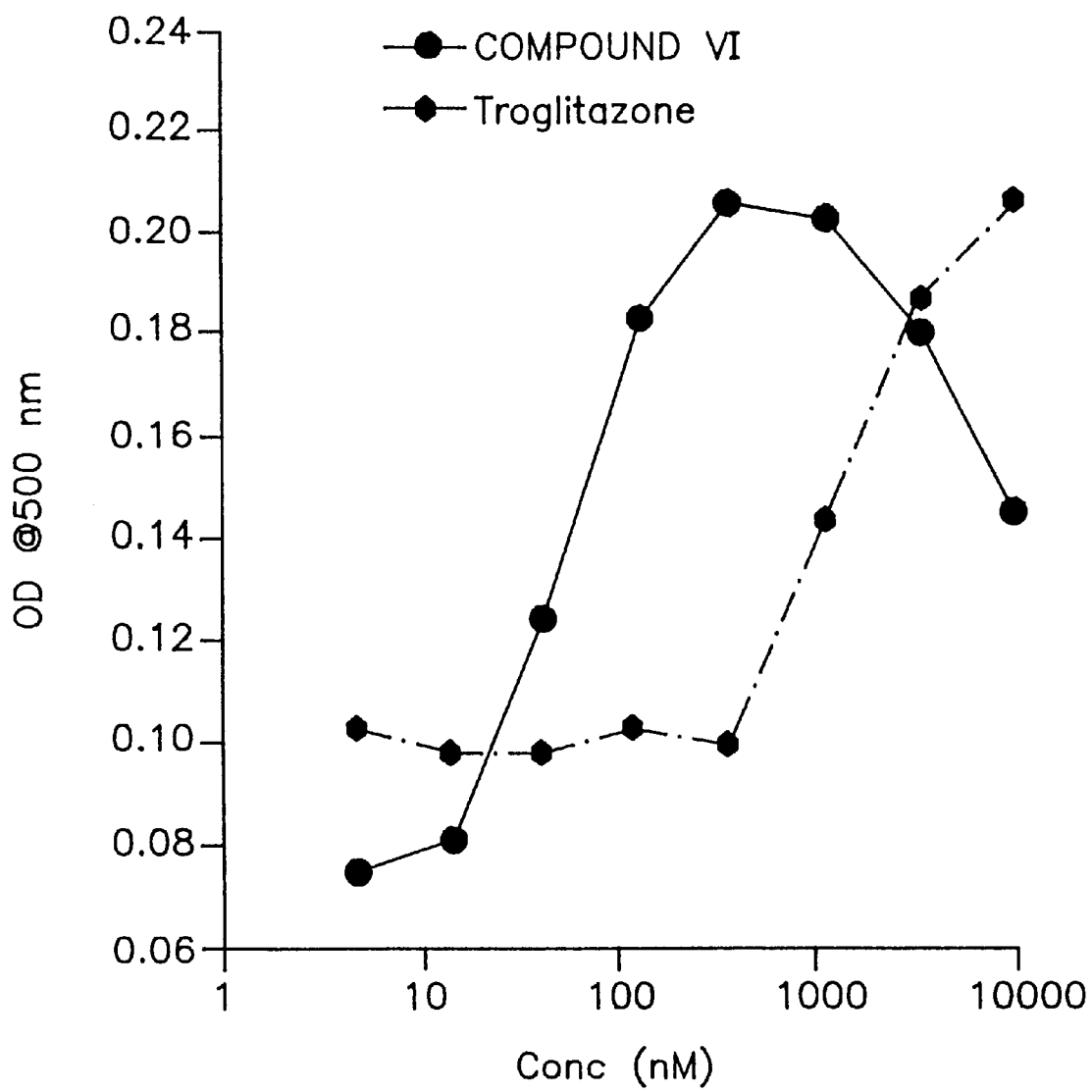
FIG. 1 represents a graph of the effect of the compound of formula VI and Troglitazone® on human preadipocytes to induce adipocyte differentiation wherein preadipocyte cell cultures were treated with the compounds. At the end of the culture, the cell cultures were stained with oil red-O dye and quantified by measuring their optical density.

As employed above and throughout the disclosure, the following terms, unless otherwise indicated, shall be understood to have the following meanings:

Definitions

In the present specification, the term "compounds for use according to the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

"Patient" includes both human and other mammals.

In the present invention the moiety

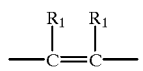

encompasses the syn and anti configurations.

"Chemical bond" means a direct bond.

"Acyl" means an H—CO— or alkyl-CO-group wherein the alkyl group is as herein described. Preferred acyls contain a lower alkyl. Exemplary acyl groups include formyl, acetyl, propanoyl, 2-methylpropanoyl, butanoyl and palmitoyl.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group is optionally substituted by one or more halo group. Exemplary alkenyl groups include ethenyl, propenyl, n-butenyl, i-butenyl, 3-methylbut-2-enyl, n-pentenyl, heptenyl, octenyl and decenyl.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl is optionally substituted with one or more "alkyl group substituents" which may be the same or different, and include halo, carboxy, alkoxycarbonyl, aralkoxycarbonyl, heteroaralkoxycarbonyl, $Y^1Y^2NCO$—, wherein $Y^1$ and $Y^2$ are independently hydrogen, alkyl, aryl, aralkyl or heteroaralkyl, or $Y^1$ and $Y^2$ taken together with the nitrogen atom to which $Y^1$ and $Y^2$ are attached form heterocyclyl. Exemplary alkyl groups include methyl, trifluoromethyl, ethyl, n-propyl, i-propyl, n-butyl, t-butyl, n-pentyl, 3-pentyl, carboxymethyl, methoxycarbonylethyl, benzyloxycarbonylmethyl, pyridylmethyloxycarbonylmethyl.

"Alkylsulfinyl" means an alkyl-SO-group wherein the alkyl group is as defined above. Preferred groups are those wherein the alkyl group is lower alkyl.

"Alkylsulfonyl" means an alkyl-$SO_2$ group wherein the alkyl group is as defined above. Preferred groups are those wherein the alkyl group is lower alkyl.

"Alkylthio" means an alkyl-S— group wherein the alkyl group is as herein described. Exemplary alkylthio groups include methylthio, ethylthio, i-propylthio and heptylthio.

"Aralkoxy" means an aralkyl-O— group wherein the aralkyl groups is as herein described. Exemplary aralkoxy groups include benzyloxy and 1- or 2-naphthalenemethoxy.

"Aralkoxycarbonyl" means an aralkyl-O—CO— group wherein the aralkyl groups is as herein described. An exemplary aralkoxycarbonyl group is benzyloxycarbonyl.

"Aralkyl" means an aryl-alkyl-group wherein the aryl and alkyl are as herein described. Preferred aralkyls contain a lower alkyl moiety. Exemplary aralkyl groups include benzyl, 2-phenethyl and naphthlenemethyl.

"Aralkylsulfonyl" means an aralkyl-$SO_2$-group wherein the aralkyl group is as herein described.

"Aralkylsulfonyl" means an aralkyl-SO-group wherein the aralkyl group is as herein described.

"Aralkylthio" means an aralkyl-S— group wherein the aralkyl group is as herein described. An exemplary aralkylthio group is benzylthio.

"Aroyl" means an aryl-CO-group wherein the aryl group is as herein described. Exemplary groups include benzoyl and 1- and 2-naphthoyl.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Exemplary aryl groups include phenyl or naphthyl, or substituted phenyl or substituted naphthyl.

"Aryldiazo" means an aryl-diazo-group wherein the aryl and diazo groups are as defined herein.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl as a variable may be bonded through any atom of the ring system thereof capable of such. The fused arylcycloalkenyl may be optionally substituted by one or more ring system substituent, wherein the "ring system substituent" is as defined herein. Exemplary fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. The fused arylcycloalkyl may be optionally substituted by one or more ring system substituent, wherein the "ring system substituent" is as defined herein. Exemplary fused arylcycloalkyl includes 1,2,3,4-tetrahydronaphthylene, and the like.

"Fused arylheterocyclyl" means a fused aryl and heterocyclyl as defined herein. Preferred fused arylheterocyclyl are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulfur atom is present respectively as a ring atom. The fused arylheterocyclyl may be optionally substituted by one or more ring system substituent, wherein the "ring system substituent" is as defined herein. The nitrogen atom of a fused arylheterocyclyl may be a basic nitrogen atom. The nitrogen or sulphur atom of the heterocyclyl portion of the fused arylheterocyclyl is also optionally oxidized to the corresponding N-oxide, S-oxide or S,S-dioxide. Exemplary fused arylheterocyclyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulphur atom is present respectively as a ring atom. The fused arylheterocyclyl may be optionally substituted by one or more ring system substituent, wherein the "ring system substituent" is as defined herein. The nitrogen atom of a fused arylheterocyclyl may be a basic nitrogen atom. The nitrogen or sulphur atom of the heterocyclyl portion of the fused arylheterocyclyl is also optionally oxidized to the corresponding N-oxide, S-oxide or S,S-dioxide. Exemplary fused arylheterocyclyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]isoquinolin-2-yl, and the like.

"Aryloxy" means an arylO-group wherein the aryl group is as defined herein. Exemplary groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-$SO_2$-group wherein the aryl group is as defined herein.

"Arylsulfinyl" means an aryl-SO-group wherein the aryl group is as defined herein.

"Arylthio" means an aryl-S-group wherein the aryl group is as herein described. Exemplary arylthio groups include phenylthio and naphthylthio.

"Carboxy" means a HO(O)C— (carboxylic acid) group.

"Compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Cycloalkoxy" means an cycloalky-O-group wherein the cycloalkyl group is as herein described. Exemplary cycloalkoxy groups include cyclopentyloxy and cyclohexyloxy.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. The cycloalkenyl is optionally substituted with one or more "ring system substituents" which may be the same or different, and are as defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. The cycloalkyl is optionally substituted with one or more "ring system substituents" which may be the same or different, and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkylene" means a bivalent, saturated carbocyclic group having about 3 to about 6 carbon atoms. Preferred cycloalkylene groups include 1,1-, 1,2-, 1,3-, or 1,4-cis or trans-cyclohexylene.

"Diazo" means a bivalent —N=N— radical.

"Halo" means fluoro, chloro, bromo, or iodo. Preferred are fluoro, chloro or bromo, and more preferred are fluoro or chloro.

"Heteroaralkyl" means a heteroaryl-alkyl-group wherein the heteroaryl and alkyl are as herein described. Preferred heteroaralkyls contain a lower alkyl moiety. Exemplary heteroaralkyl groups may contain thienylmethyl, pyridylmethyl, imidazolylmethyl and pyrazinylmethyl.

"Heteroaralkylthio" means an aralkyl-S-group wherein the aralkyl group is as herein described. An exemplary aralkylthio group is benzylthio.

"Heteroaralkoxy" means an heteroaralkylO-group wherein the heteroaralkyl group is as herein described. An exemplary heteroaralkoxy group is 4-pyridylmethyloxy.

"Heteroaroyl" means an means an heteroaryl-CO-group wherein the heteroaryl group is as herein described. Exemplary groups include thiophenoyl, nicotinoyl, pyrrol-2-ylcarbonyl and 1- and 2-naphthoyl and pyridinoyl.

"Heteroaryldiazo" means an heteroaryl-diazo-group wherein the heteroaryl and diazo groups are as defined herein.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The "heteroaryl" is optionally substituted by one or more "ring system substituents" which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be a basic nitrogen atom and is also optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidaz[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroarylcycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present respectively as a ring atom. The fused heteroarylcycloalkenyl may be optionally substituted by one or more ring system substituent, wherein the "ring system substituent" is as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Exemplary fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl as a variable may be bonded through any atom of the ring system thereof capable of such. The designation of the aza, oxa or thia as a prefix before heteroaryl portion of the fused heteroarylcycloalkyl define that at least a nitrogen, oxygen or sulfur atom is present respectively as a ring atom. The fused heteroarylcycloalkyl may be optionally substituted by one or more ring system substituent, wherein the "ring system substituent" is as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroarylheterocyclenyl define that at least a nitrogen, oxygen or sulfur atom is present respectively as a ring atom. The fused heteroarylheterocyclenyl may be optionally substituted by one or more ring system substituent, wherein the "ring system substituent" is as defined herein. The nitrogen atom of a fused heteroarylazaheterocyclenyl may be a basic nitrogen atom. The nitrogen or sulphur atom of the heteroaryl portion of the fused heteroarylheterocyclyl may also be optionally oxidized to the corresponding N-oxide. The nitrogen or sulphur atom of the heteroaryl or heterocyclyl portion of the fused heteroarylheterocyclyl may also be optionally oxidized to the corresponding N-oxide, S-oxide or S,S-dioxide. Exemplary fused heteroarylhetercyclenyl include 7,8-dihydro[1,7]naphthyridinyl, 1,2-dihydro[2,7] naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like.

"Fused heteroarylheterocyclyl" means a fused heteroaryl and heterocyclyl as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl as a variable may be bonded through any atom of the ring system thereof capable of such. The designation of the aza, oxa or thia as a prefix before the heteroaryl or heterocyclyl portion of the fused heteroaryl-heterocyclyl define that at least a nitrogen, oxygen or sulfur atom is present respectively as a ring atom. The fused heteroarylheterocyclyl may be optionally substituted by one or more ring system substituent, wherein the "ring system substituent" is as defined herein. The nitrogen atom of a fused heteroarylheterocyclyl may be a basic nitrogen atom. The nitrogen or sulphur atom of the heteroaryl portion of the fused heteroarylheterocyclyl may also be optionally oxidized to the corresponding N-oxide. The nitrogen or sulphur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclyl include 2,3-dihydro-1H pyrrol[3,4-b]quinolin-2-yl, 1,2,3,4-tetrahydrobenz[b][1,7] naphthyridin-2-yl, 1,2,3,4-tetrahydrobenz [b][1,6] naphthyridin-2-yl, 1,2,3,4-tetrahydro-9 H-pyrido[3,4-b] indol-2yl,1,2,3,4-tetrahydro-9H-pyrido[4,3-b]indol-2yl, 2,3,-dihydro-1H-pyrrolo[3,4-b]indol -2-yl, 1H-2,3,4,5-tetrahydroazepino[3,4-b]indol-2-yl, 1H-2,3,4,5-tetrahydroazepino[4,3-b]indol-3-yl, 1H -2,3,4,5-tetrahydroazepino[4,5-b]indol-2 yl, 5,6,7,8-tetrahydro[1,7] napthyridinyl, 1,2,3,4-tetrahydro[2,7]naphthyridyl, 2,3-dihydro[1,4]dioxino[2,3-b]pyridyl,2,3-dihydro[1,4]dioxino [2,3b]pyridyl, 3,4-dihydro-2H-1-oxa[4,6] diazanaphthalenyl, 4,5,6,7-tetrahydro-3H-imidazo[4,5-c] pyridyl, 6,7-dihydro[5,8]diazanaphthalenyl, 1,2,3,4-tetrahydro[1,5]napthyridinyl, 1,2,3,4-tetrahydro[1,6] napthyridinyl, 1,2,3,4-tetrahydro[1,7]napthyridinyl, 1,2,3,4-tetrahydro[1,8]napthyridinyl, 1,2,3,4-tetrahydro[2,6] napthyridinyl, and the like.

"Heteroarylsulfonyl" means an heteroaryl-$SO_2$-group wherein the heteroaryl group is as defined herein.

"Heteroarylsulfinyl" means an heteroaryl-SO-group wherein the heteroaryl group is as defined herein.

"Heteroarylthio" means an heteroaryl-S-group wherein the heteroaryl group is as herein described. Exemplary heteroaryl thio groups include pyridylthio and quinolinylthio.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of rings of the ring system include about 5 to about 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more ring system substituent, wherein the "ring system substituent" is as defined herein. The nitrogen atom of an heterocyclenyl may be a basic nitrogen atom. The nitrogen or sulphur atom of the heterocyclenyl is also optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydrofuranyl. An exemplary multicyclic oxaheterocyclenyl group is 7-oxabicyclo[2.2.1]heptenyl. Exemplary monocyclic thiaheterocycleny rings include dihydrothiophenyl and dihydrothiopyranyl.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more "ring system substituents" which may be the same or different, and are as defined herein. The nitrogen atom of an heterocyclyl may be a basic nitrogen atom. The nitrogen or sulphur atom of the heterocyclyl is also optionally oxidized to the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Ring group substituent" includes hydrogen, alkyl, cycloalkyl, heterocyclyl, aryl, heteroaryl, aralkyl, heteroaralkyl, hydroxy, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused cycloalkenyl, fused heterocyclyl, fused heterocyclenyl, arylazo, heteroarylazo, $R^aR^bN-$, $R^cR^dNCO-$ or $R^cR^dNSO_2-$. Where the ring is cycloalkyl, cycloalkenyl, heterocyclyl or heterocyclenyl, the ring group substituent also includes oxo on carbon atom(s) thereof. $R^a$ and $R^b$ are independently hydrogen, alkyl, aryl, aralkyl or heteroaralkyl, or one of $R^a$ and $R^b$ is hydrogen or alkyl and the other of $R^a$ and $R^b$ is aroyl or heteroaroyl. $R^c$ and $R^d$ are independently hydrogen, alkyl, aryl, aralkyl or heteroaralkyl.

"Tetrazolyl" means a group of formula

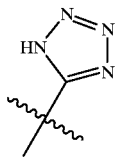

wherein the hydrogen atom thereof is optionally substituted by alkyl, carboxyalkyl or alkoxycarbonylalkyl.

"PPAR-γ ligand receptor binder" means a ligand which binds to the PPAR-γ receptor. PPAR-γ ligand receptor binders of this invention are useful as agonists or antagonists of the PPAR-γ receptor.

The term "pharmaceutically acceptable salt" refers to a relatively non-toxic, inorganic and organic acid addition salt of a compound of the present invention. A salt can be prepared in situ during the final isolation and purification of a compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts, and the like. (See, for example S. M. Berge, et at., "Pharmaceutical Salts," *J. Pharm. Sci.*, 66: 1–19 (1977) which is incorporated herein by reference.).

"Treating" means the partial or complete relieving or preventing of one or more physiological or biochemical parameters associated with PPAR-γ activity.

The term "modulate" refers to the ability of a compound to either directly (by binding to the receptor as a ligand) or indirectly (as a precursor for a ligand or an inducer which promotes production of a ligand from a precursor) induce expression of gene(s) maintained under hormone control, or to repress expression of gene(s) maintained under such control.

The term "obesity" refers generally to individuals who are at least about 20–30% over the average weight for the person's age, sex and height. Technically "obese" is defined, for males, as individuals whose body mass index is greater than 27.3 kg/m². Those skilled in the art readily recognize that the invention method is not limited to those who fall within the above criteria. Indeed, the invention method can also be advantageously practiced by individuals who fall outside of these traditional criteria, for example by those who are prone to obesity.

The phrase "amount effective to lower blood glucose levels" refers to levels of compound sufficient to provide circulating concentrations high enough to accomplish the desired effect. Such a concentration typically falls in the range of about 10 nM up to 2 μM; with concentrations in the range of about 100 nm up to about 500 nM being preferred.

Preferred Embodiments

An embodiment according to the invention is the use of quinolinyl phenyl compounds and their pharmaceutical compositions as PPAR-γ ligand receptor binders.

An embodiment according to the invention is the use of quinolinyl phenyl compounds and their pharmaceutical compositions as PPAR-γ ligand receptor agonists.

An embodiment according to the invention is the use of quinolinyl phenyl compounds and their pharmaceutical compositions as PPAR-γ receptor antagonists.

An embodiment according to the invention is directed to treating a patient suffering from a physiological disorder capable of being modulated by a compound of formula I having PPAR-γ ligand binding activity, comprising administering to the patient a pharmaceutically acceptable amount of the compound, or a pharmaceutically acceptable salt thereof. Physiological disorders capable of being modulated include, for example, cell differentiation to produce lipid accumulating cells, regulation of insulin-sensitivity and blood glucose levels, especially in relation to hypoglycemia/ hyperinsulinism (resulting, for example, from abnormal pancreatic β-cell function, insulin secreting-tumors and/or autoimmune hypoglycemia due to autoantibodies to insulin, the insulin receptor or autoantibodies that are stimulatory to pancreatic β-cells), the formation of macrophages which lead to the development of atherosclerotic plaques, and the like.

Another embodiment according to the invention is directed to a method of treating a disease state in a patient with a pharmaceutically effective amount a compound of formula I or a pharmaceutically acceptable salt thereof, wherein the disease is associated with a physiological detrimental level of insulin, glucose, free fatty acids (FFA), or triglycerides, in the blood.

An embodiment according to the invention is the use of quinolinyl phenyl compounds and their pharmaceutical compositions as anti-diabetic, anti-lipidemic, anti-hypertensive and anti-arterioslerotic agents, and in the treatment of obesity.

Another embodiment according to the invention is directed to a method of treating hyperglycemia in a patient, comprising administering to the patient a pharmaceutically effective amount of a compound of formula I, or a pharmaceutically acceptable salt thereof, effective to lower blood glucose levels. A more preferred hyperglycemia, treatable according to this invention is Type II diabetes.

Another embodiment according to the invention is directed to a method of treating of hyperinsulinism in a patient, comprising administering to the patient a therapeutically effective amount of a compound of formula I or a pharmaceutically acceptable salt thereof.

Another embodiment according to the invention is directed to a method of treating insulin resistance in a patient, comprising administering to the patient a therapeutically effective amount of a compound of formula I or a pharmaceutically acceptable salt thereof.

Another embodiment according to the invention is directed to a method of treating cardiovascular disease in a patient, comprising administering to the patient a therapeutically effective amount of a compound of formula I, or a pharmaceutically acceptable salt thereof. A more preferred cardiovascular disease, treatable according to this invention is atherosclerosis.

Another embodiment according to the invention is directed to treating of hyperlipidemia in a patient, comprising administering to the patient a therapeutically effective amount of a compound of formula I, or a pharmaceutically acceptable salt thereof.

Another embodiment according to the invention is directed to treating of hypertension in a patient, comprising administering to the patient a therapeutically effective amount of a compound of formula I, or a pharmaceutically acceptable salt thereof.

Another embodiment according to the invention is directed to treating eating disorders in a patient, comprising administering to the patient a therapeutically effective amount of a compound of formula I, or a pharmaceutically acceptable salt thereof. Eating disorders include the regulation of appetite or food intake in patients suffering from under-eating disorders such as anorexia nervosa, and over-eating disorders such as obesity and anorexia bulimia.

It is a further object of the invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

In another aspect, the present invention provides a method for treating a disease state in a patient, wherein the disease is associated with a physiological detrimental level of insulin, glucose, free fatty acids (FFA), or triclycerides, in the blood, comprising administering to the patient a therapeutically effective amount a compound of the formula I, and administering a therapeutically effective amount of an additional hypoglycemic agent.

In another aspect, the present invention provides a method for treating a disease state in a patient, wherein the disease is associated with a physiological detrimental level of insulin, glucose, free fatty acids (FFA), or triclycerides, in the blood, comprising administering to the patient a therapeutically effective amount a compound of the formula I, and administering a therapeutically effective amount of a biguanidine compound.

In another aspect, the present invention provides a method for treating a disease state in a patient, wherein the disease is associated with a physiological detrimental level of insulin, glucose, free fatty acids (FFA), or triclycerides, in the blood, comprising administering to the patient a therapeutically effective amount a compound of the formula I, and administering a therapeutically effective amount of metformin.

The invention also provides kits or single packages combining two or more active ingredients useful in treating the disease. A kit may provide (alone or in combination with a pharmaceutically acceptable diluent or carrier), the compound of formula (I) and an additional hypoglycaemic agent (alone or in combination with diluent or carrier).

There are many known hypoglycemic agents in the art, for example, insulin; biguanidines such as metformin or buformin; sulfonylureas such as acetohexamide, chloropropamide, tolazamide, tolbutamide, glyburide, glypizide or glyclazide; thiazolidinediones such as troglitazone; a-glycosidase inhibitors such as acarbose or miglatol; or $B_3$ adrenorecptor agonists such as CL-316, 243.

Since sulfonylureas are known to be capable of stimulating insulin release, but are not capable of acting on insulin resistance, and compounds of the formula I are able to act on insulin resistance, it is envisaged that a combination of these medicaments could be used as a remedy for conditions associated with both deficiency in insulin secretion and insulin-resistance.

Therefore the invention also provides a method of treating diabetes mellitus of type II in a patient comprising administering a compound of the formula I and one or more additional hypoglycemic agents selected from the group consisting of sulfonylureas, biguanidines, thiazolidinediones, $B_3$-adrenoreceptor agonists, a-glycosidase inhibitors and insulin.

The invention also provides a method of treating diabetes mellitus of type II in a patient comprising administering a compound of the formula I and a sulfonylurea selected from the group consisting of acetohexaminde, chlorpropamide, tolazamide, tolbutamide, glyburide, glypizide and glyclazide.

The invention also provides a method of treating diabetes mellitus of type II in a patient comprising administering a compound of the formula I and a biguanidine selected from the group consisting of metformin and buformin.

The invention also provides a method of treating diabetes mellitus of type II in a patient comprising administering a compound of the formula I and an a-glycosidase inhibitor selected from the group consisting acarbose and miglatol.

The invention also provides a method of treating diabetes mellitus of type II in a patient comprising administering a compound of the formula I and an thiazolidinedione, for example troglitazone.

In the above described methods, a compound of the formula I may be administered alone or in combination with one or more additional hypoglycemic agents. Combination therapy includes administration of a single pharmaceutical dosage formulation which contains a compound of the formula I and one or more additional hypoglycemic agent, as well as administration of the compound of the formula I and each additional hypoglycemic agents in its own separate pharmaceutical dosage formulation. For example, a compound of the formula I and hypoglycemic agent can be administered to the patient together in a single oral dosage composition such as a tablet or capsule, or each agent administered in separate oral dosage formulations. Where separate dosage formulations are used, the compound of the formula I and one or more additional hypoglycemic agents can be administered at essentially the same time, i.e., concurrently, or at separately staggered times, i.e., sequentially.

For example, the compound of the formula I may be administered in combination with one or more of the following additional hypoglycemic agents, for example, insulin; biguanidines such as metformin or buformin; sulfonylureas such as acetohexamide, chloropropamide, tolazamide, tolbutamide, glyburide, glypizide or glyclazide; thiazolidinediones such as troglitazone; a-glycosidase inhibitors such as acarbose or miglatol; or $B_3$ adrenorecptor agonists such as CL-316, 243.

The compound of the formula I is preferably administered with a biguanidine, in particular, metformin.

The compounds of Formula I contain at least three aromatic rings, which may be designated as shown in Formula II below, and for which their substitution pattern along the chain with respect to each other is shown also below.

(II)

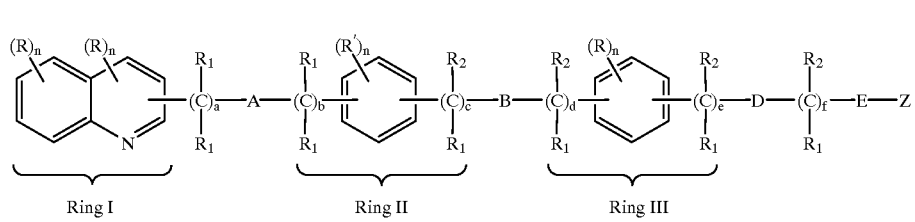

A preferred compound aspect of the compound of formula II is substitution on the quinoline ring, that is Ring I, preferably at the 2-position for extending the side chain. As this side chain progresses from the quinoline ring, the two phenyl rings, designated Ring II and Ring III is optionally substituted along the chain in the ortho, meta or para positions with respect to each other and Ring II is also optionally substituted in the ortho, meta and para positions in respect to the quinoline ring.

Another preferred compound aspect of the compound of formula II has a preferred substitution pattern for Ring II which is meta or para, that is:

IIIa

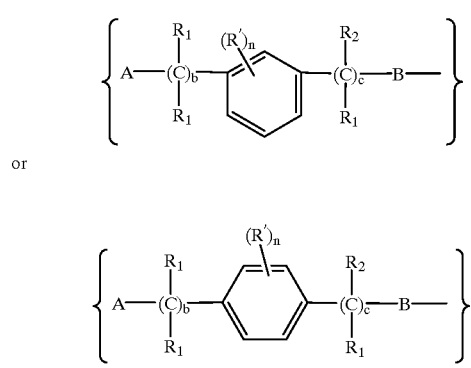

or

IIIb

Ring III is optionally substituted equally in the ortho, meta or para positions, that is:

IVa

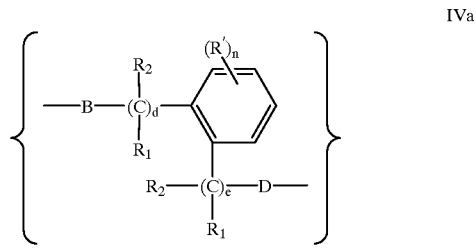

-continued

IVb

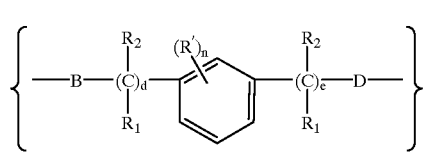

or

IVc

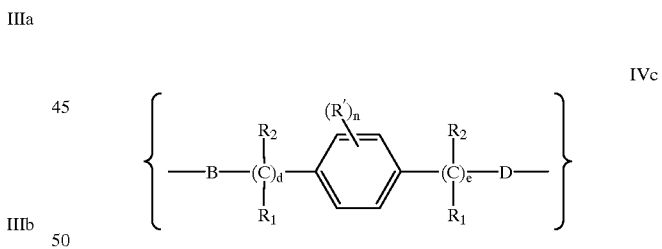

A further preferred aspect of the compound of formula II is described by formula V below:

(V)

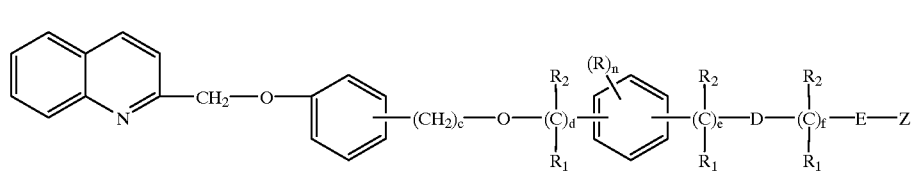

where c+d=1–3 and R, $R_1$, $R_2$, e, f, n, D, E and Z are as described above.

A further preferred aspect of the compound of formula I is a=1.

A further preferred aspect of the compound of formula I is a=0.

A further preferred aspect of the compound of formula I is b=0.

A further preferred aspect of the compound of formula I is c=0.

A further preferred aspect of the compound of formula I is d=0.

A further preferred aspect of the compound of formula I is d=1.

A further preferred aspect of the compound of formula I is a=1, A is O, and b=0.

A further preferred aspect of the compound of formula I is a=0, A is

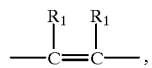

and b=0.

A further preferred aspect of the compound of formula I is where c=0, and d=1.

A further preferred aspect of the compound of formula I is where c=0, B is O, and d=1.

A further preferred aspect of the compound of formula I is where c=0, B is

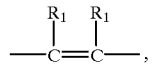

and d=0.

A further preferred aspect of the compound of formula I is where a+b=0–2.

A further preferred aspect of the compound of formula I is where a+b=1.

A further preferred aspect of the compound of formula I is where a=1.

A further preferred aspect of the compound of formula I is where c=1, d=0.

A further preferred aspect of the compound of formula I is where B is a chemical bond.

A further preferred aspect of the compound of formula I is where c=1, d=0, and B is a chemical bond.

A further preferred aspect of the compound of formula I is where e+f=0–4.

A further preferred aspect of the compound of formula I is where e+f=3.

A further preferred aspect of the compound of formula I is where e+f=1.

A further preferred aspect of the compound of formula I is where e+f=1, and D and E are chemical bonds.

A further preferred aspect of the compound of formula I is where e=0.

A further preferred aspect of the compound of formula I is where f=1, 2, or 3.

A further preferred aspect of the compound of formula I is where e=0, and D is O.

A further preferred aspect of the compound of formula I is where e=0 and D is a chemical bond.

A further preferred aspect of the compound of formula I is where e=0, D is a chemical bond, and E is a chemical bond.

A further preferred aspect of the compound of formula I is where $R_1$ is H, alkyl, or aryl.

A further preferred aspect of the compound of formula I is where R is halo, alkyl, hydrogen, alkoxy or alkoxycarbonyl.

A further preferred aspect of the compound of formula I is where A is

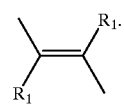

A further preferred aspect of the compound of formula I is where B is

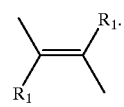

A further preferred aspect of the compound of formula I is where D is

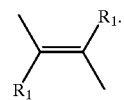

A further preferred aspect of the compound of formula I is where E is

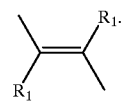

A more preferred aspect of the compound of Formula I are those where Z is —$COOR_1$, —CN, Cl, $R_3O_2SHNCO$—, or tetrazolyl.

A more preferred aspect of the compound of Formula I are those where X is hydrogen, alkyl, alkenyl, cycloalkyl, aryl, aralkyl, hydroxy, alkoxy, aralkoxy, carboxy, alkoxycarbonyl, tetrazolyl, acylHNSO$_2$—, $Y^1Y^2N$— or $Y^3Y^4NCO$—.

A more preferred aspect of the compound of Formula I are those where $Y^1$ and $Y^2$ are independently hydrogen, alkyl, or aralkyl or one of $Y^1$ and $Y^2$ is hydrogen and the other of $Y_1$ and $Y^2$ is acyl.

A more preferred aspect of the compound of Formula I are those where $Y^3$ and $Y^4$ are hydrogen.

A more preferred compound aspect of the compound of Formula V are those where Z is —$COOR_1$, —CN, $R_3O_2SHNCO$—, Cl, or tetrazolyl.

A preferred compound according to the invention is selected from the group of formulae consisting of
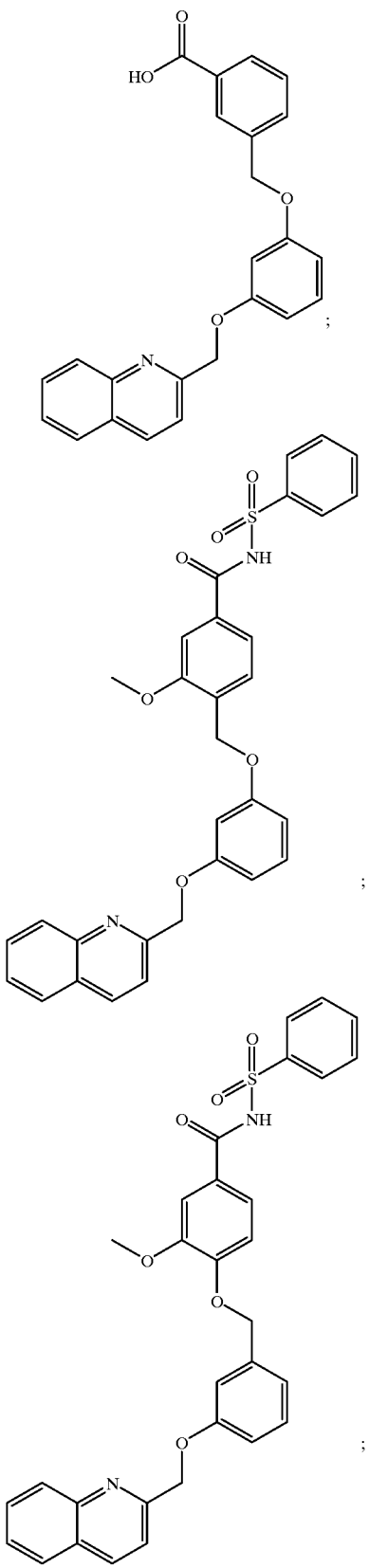
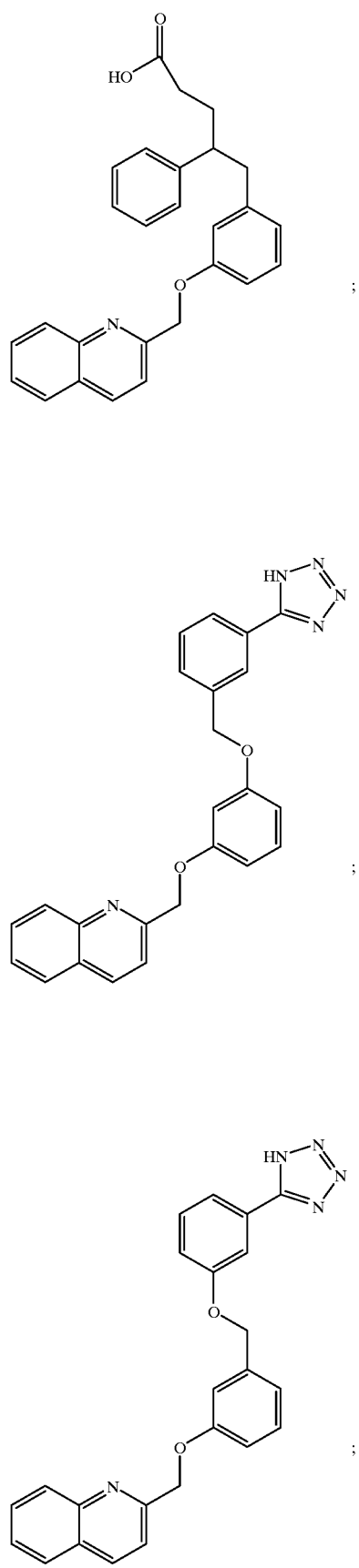

-continued

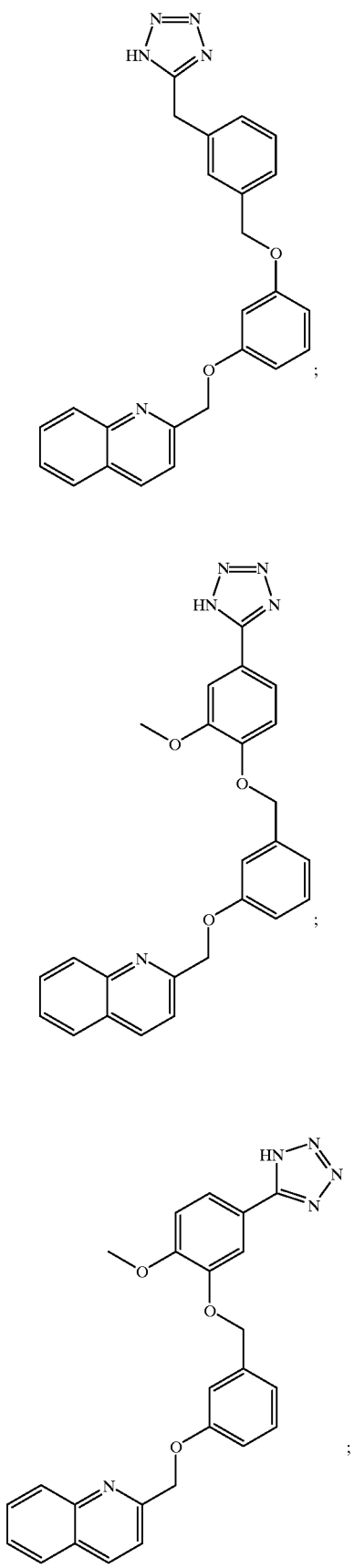
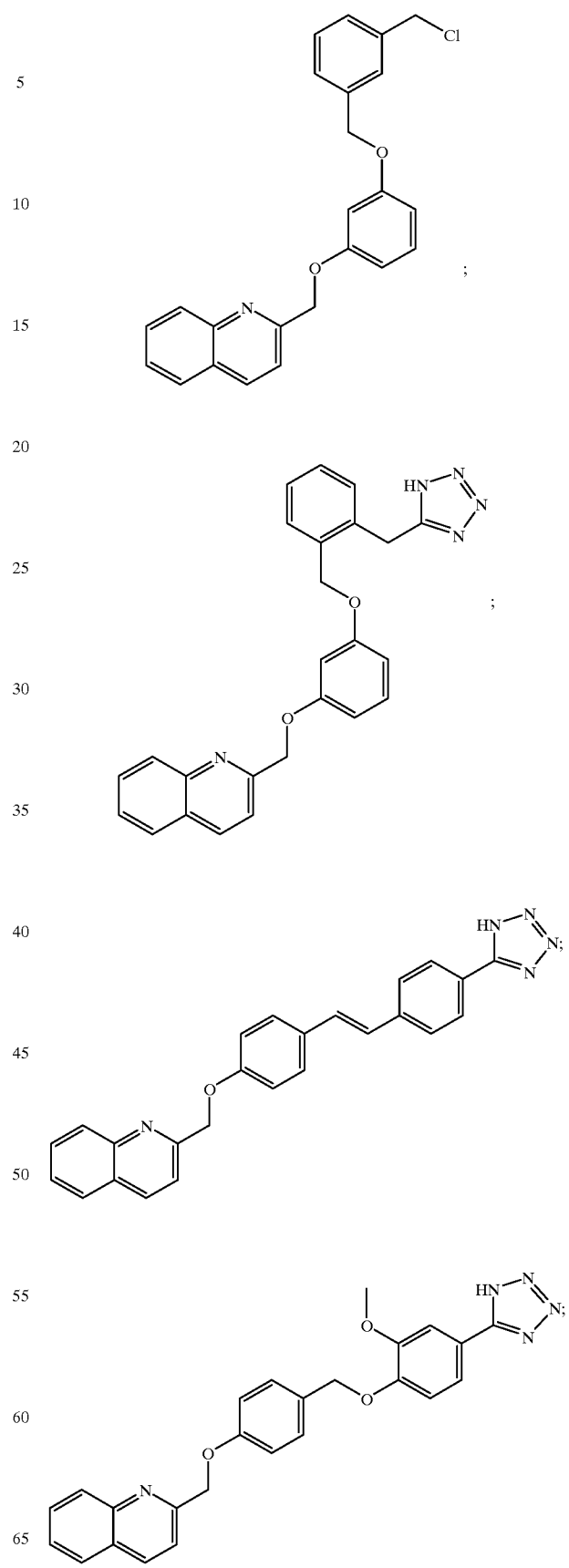

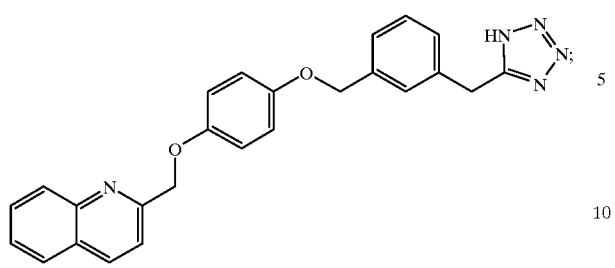
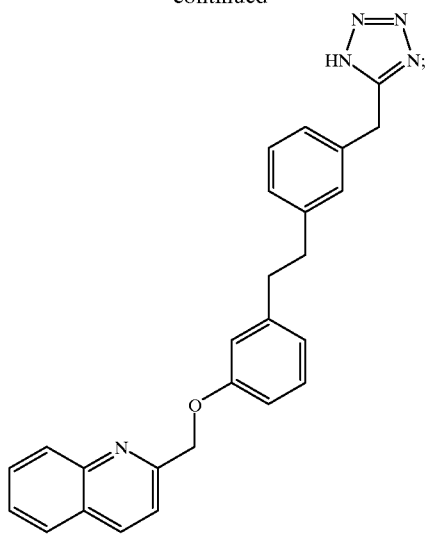
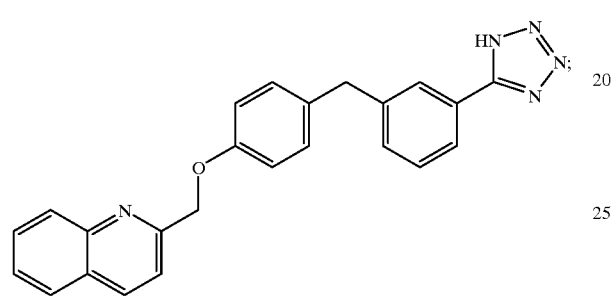
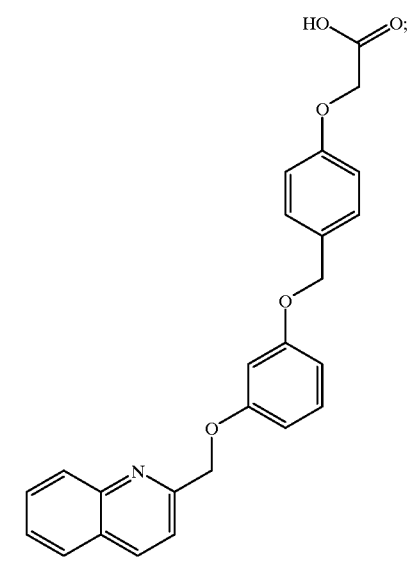
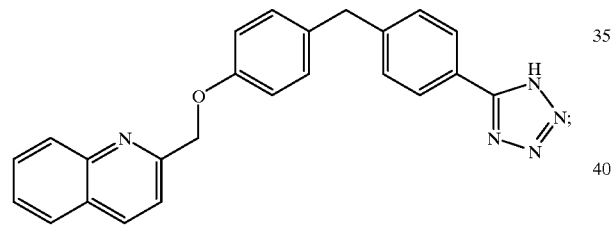
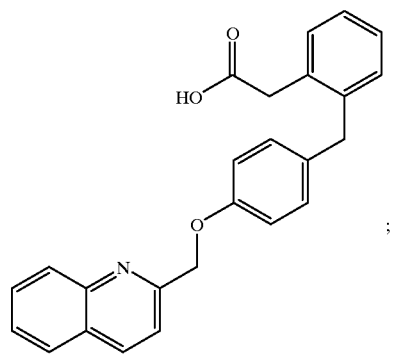
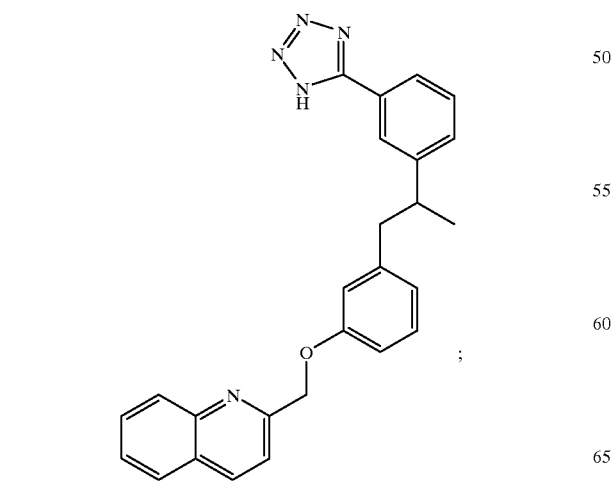

27
-continued
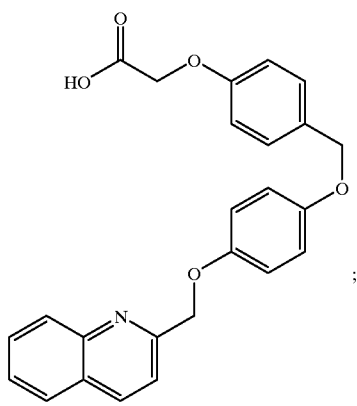
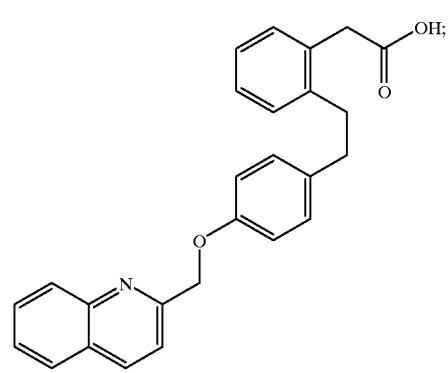
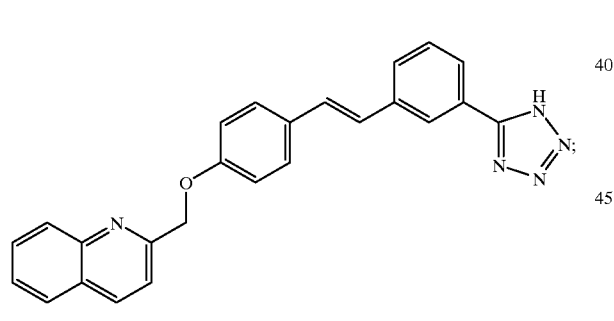
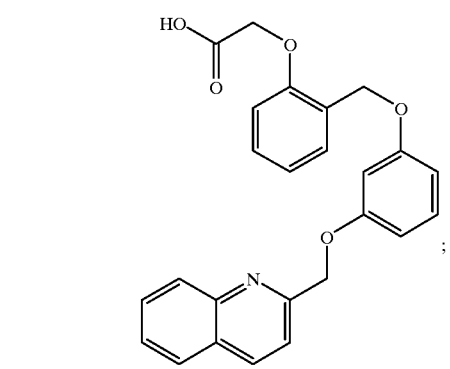
28
-continued
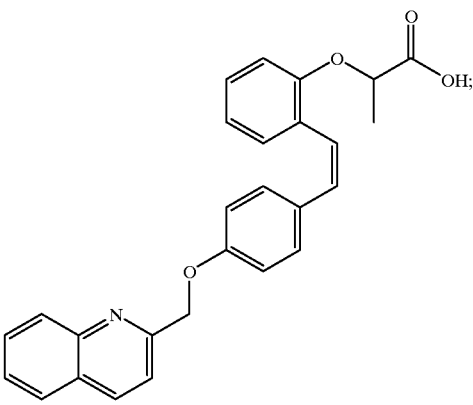
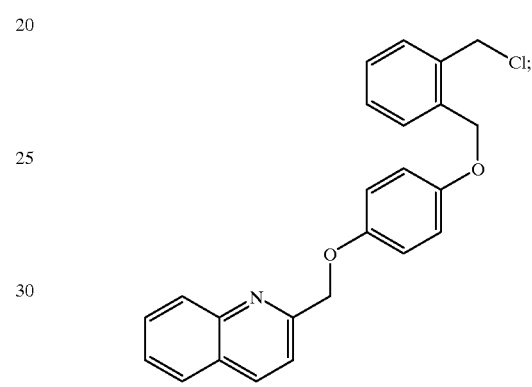
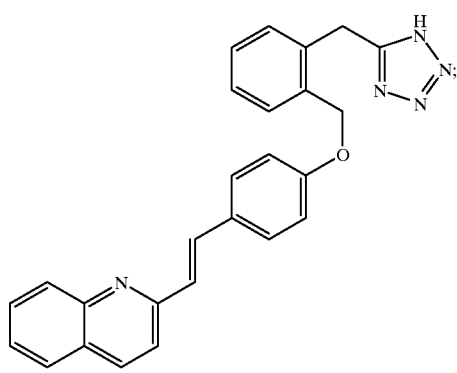
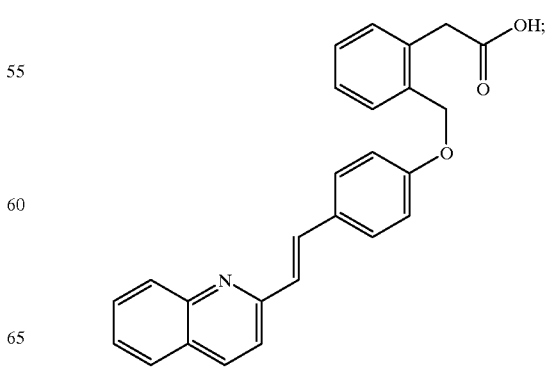

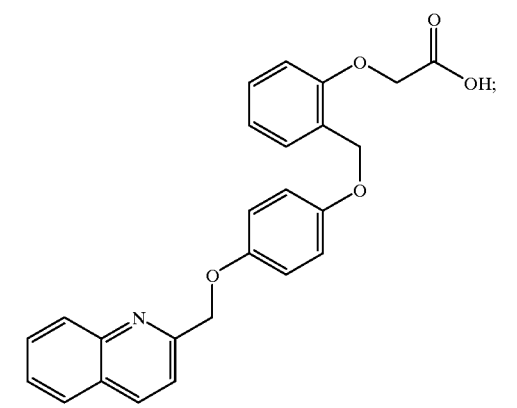
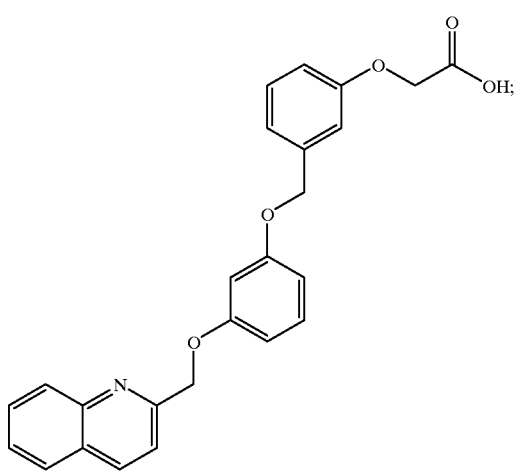
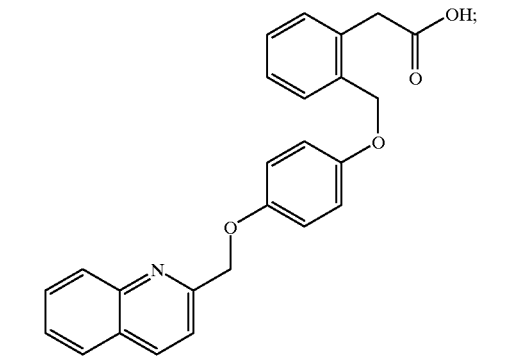
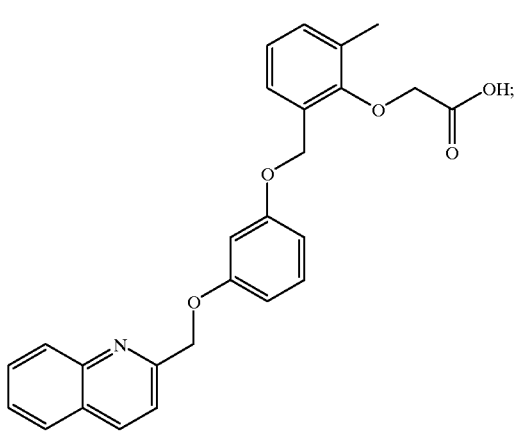
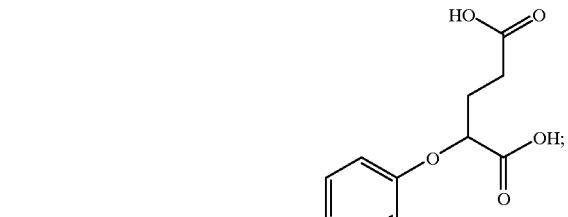
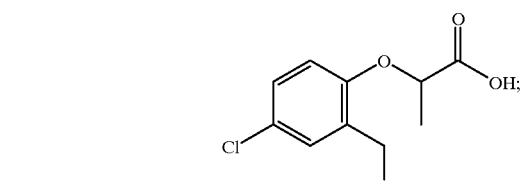
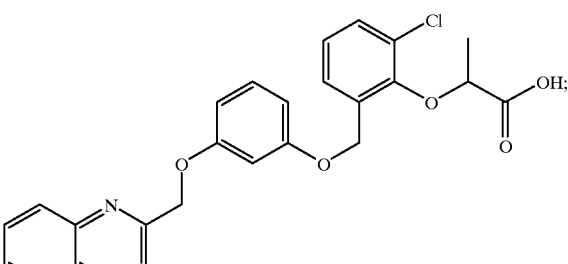

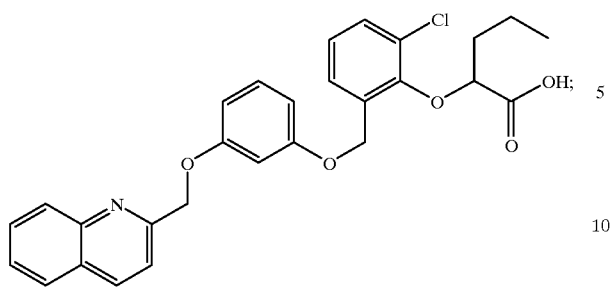
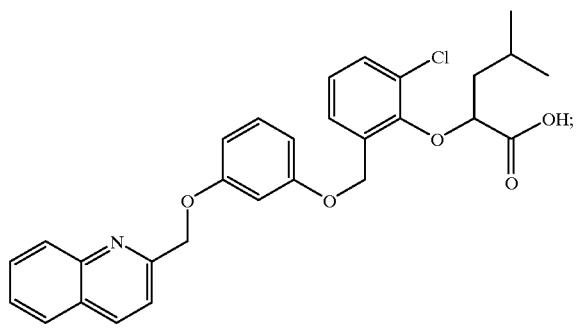
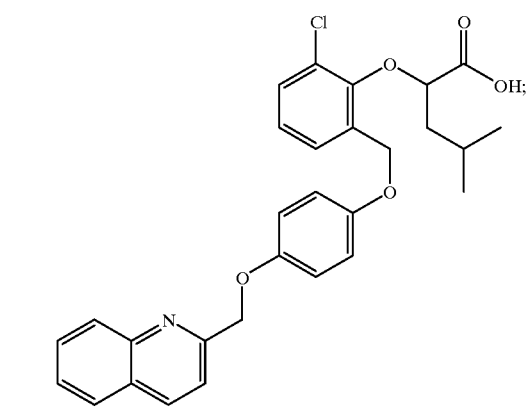
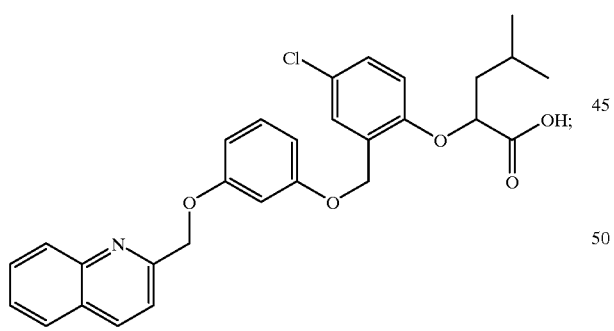
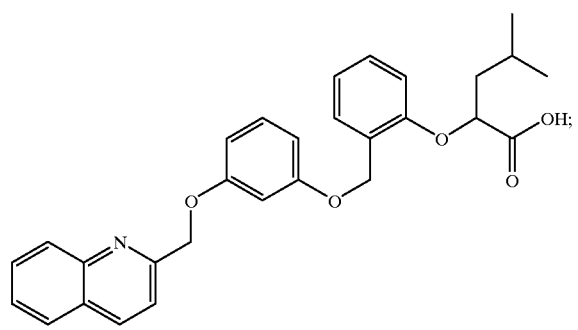
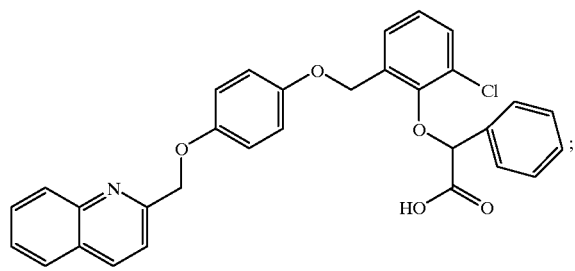
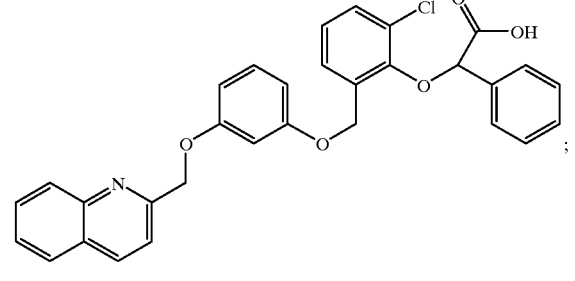
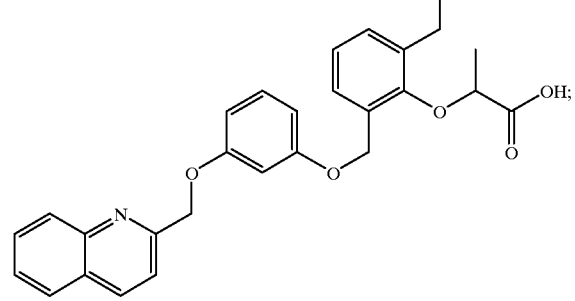
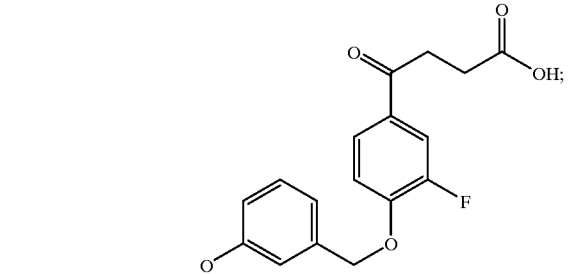
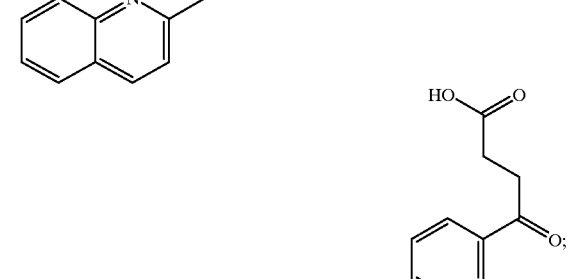
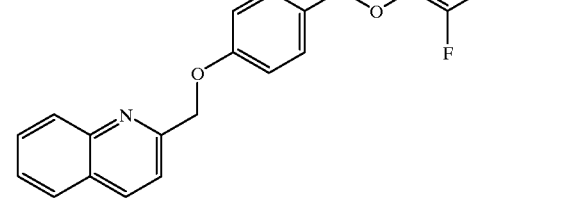

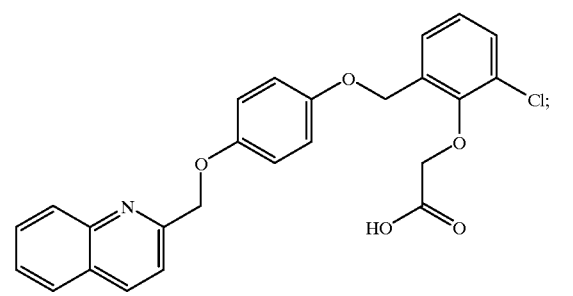
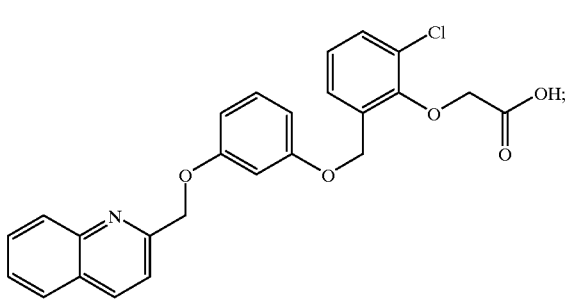
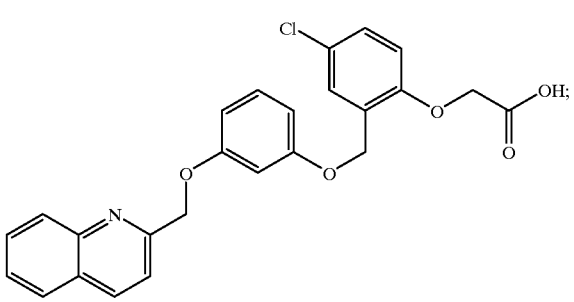
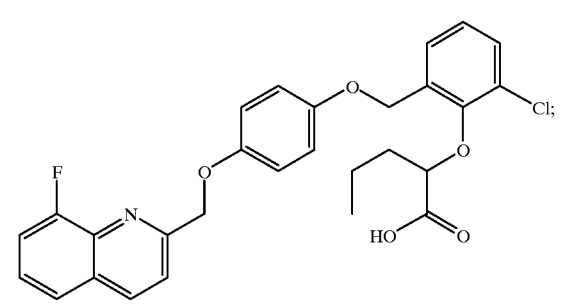
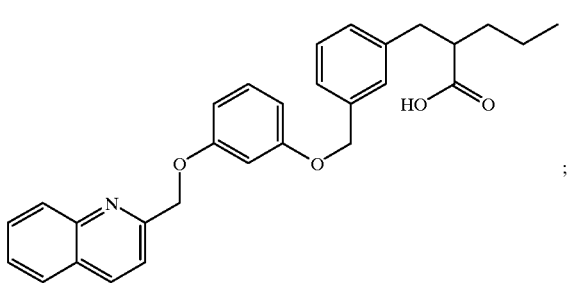
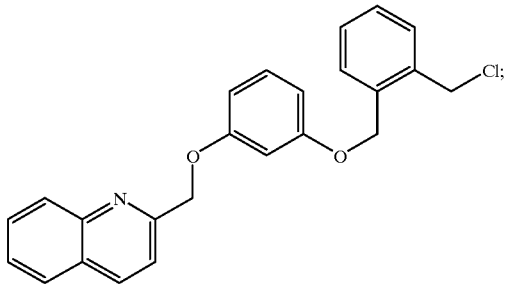
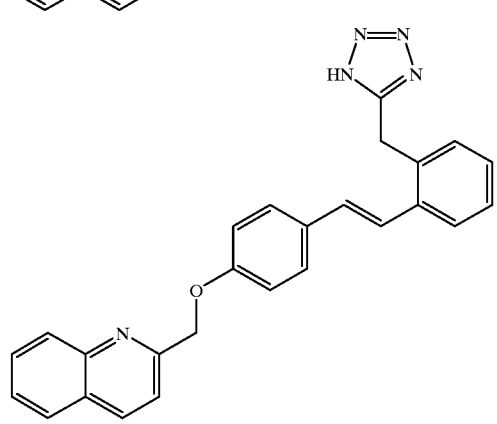
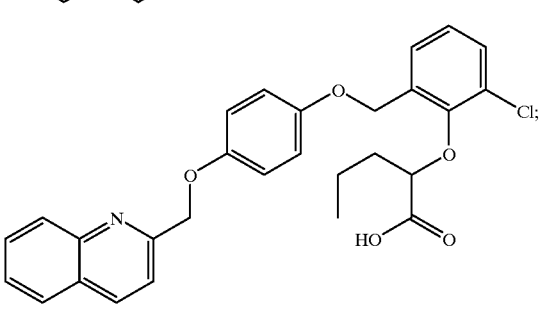
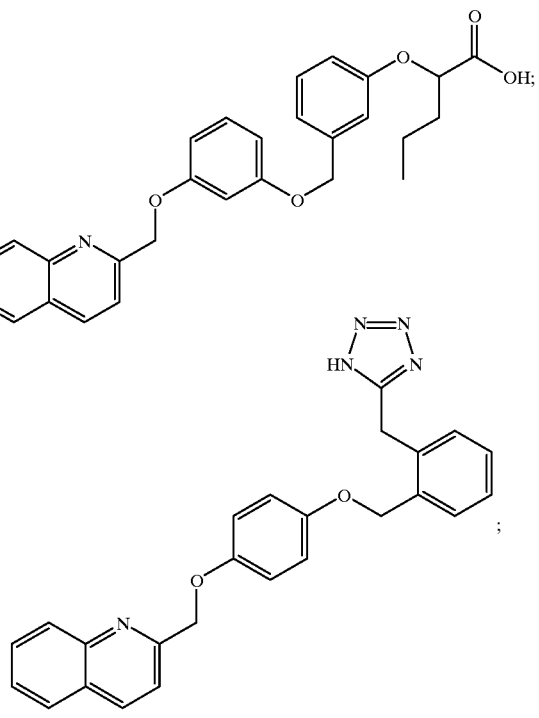
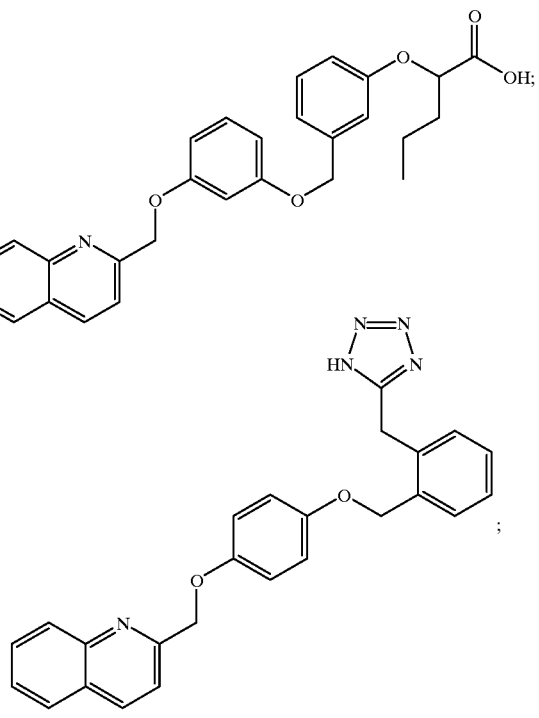

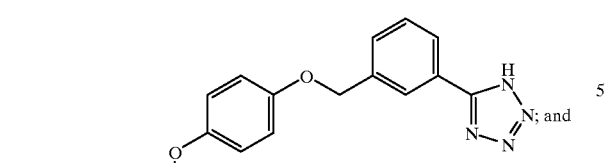
A preferred compound according to the invention is selected from the group consisting of
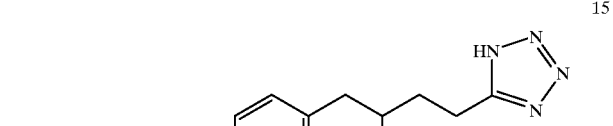
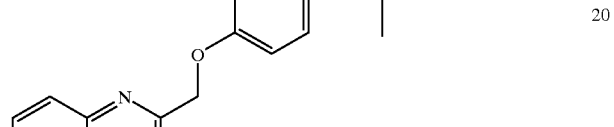
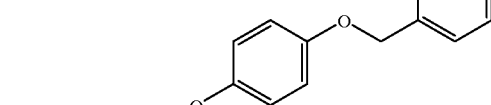
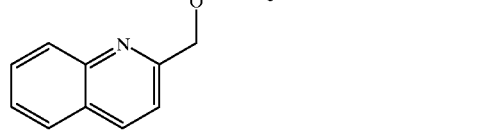
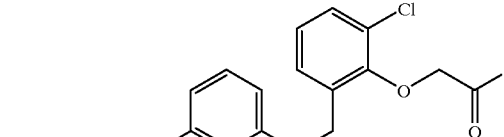
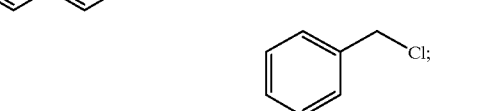
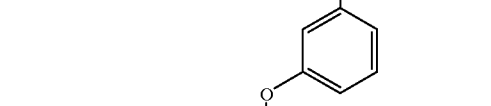

37
-continued
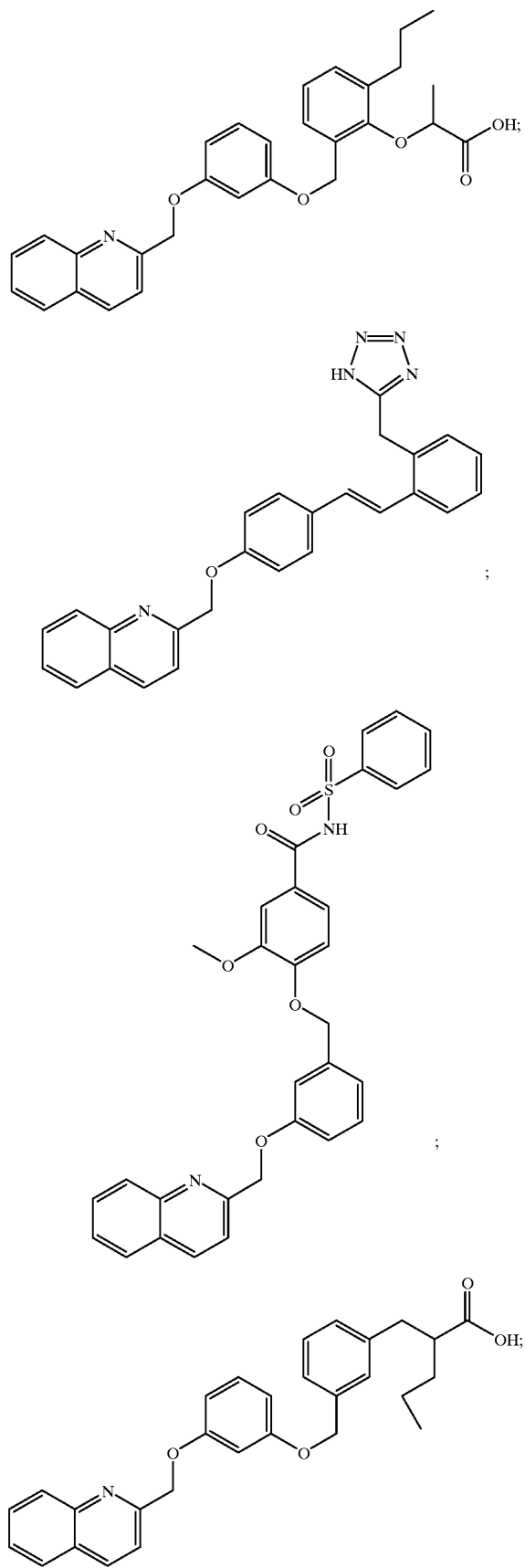
38
-continued
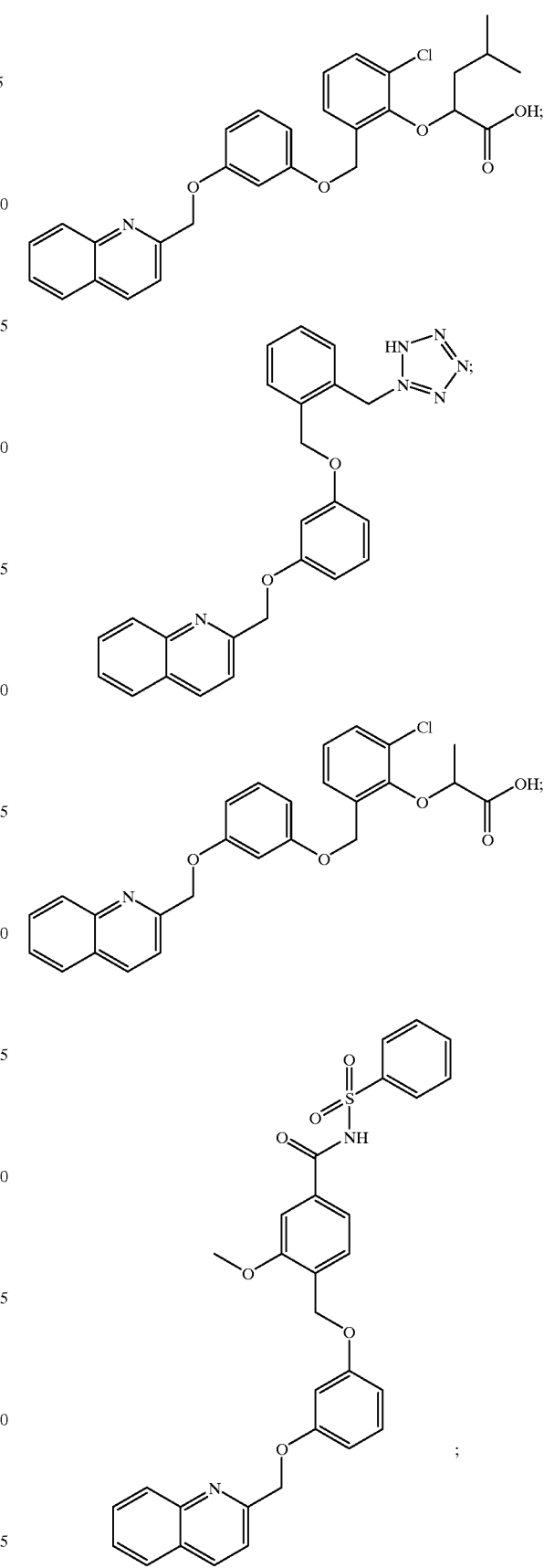

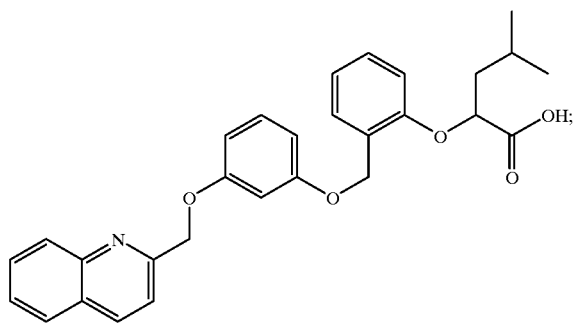
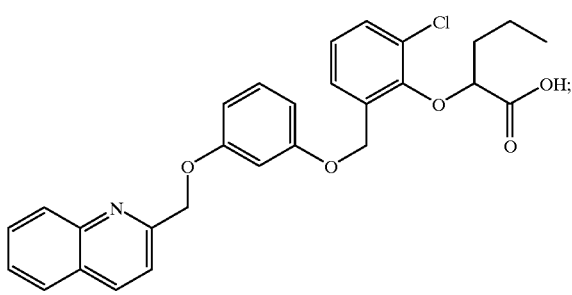
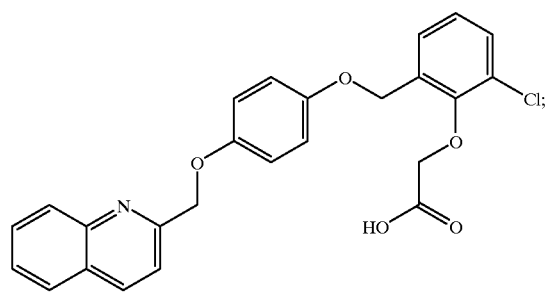
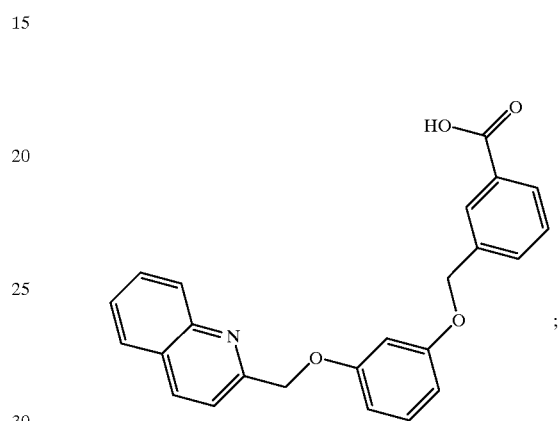
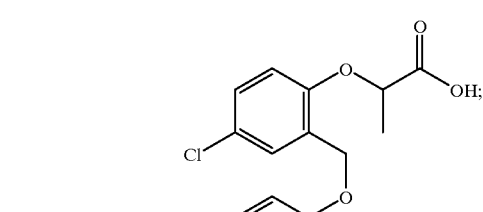
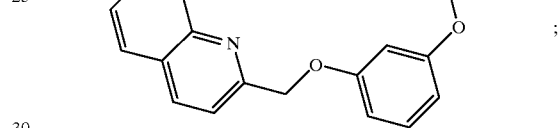
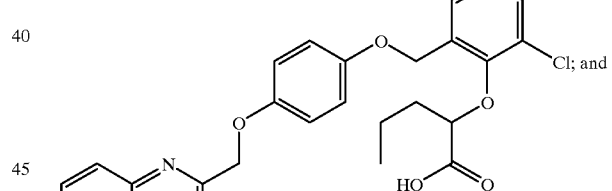
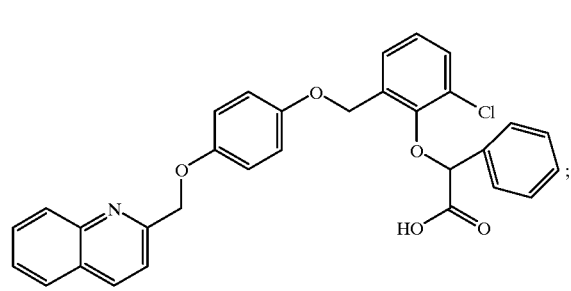
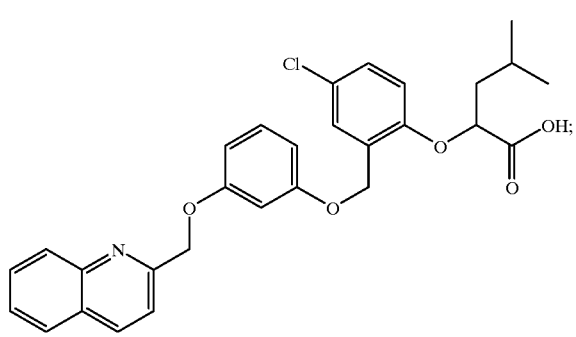
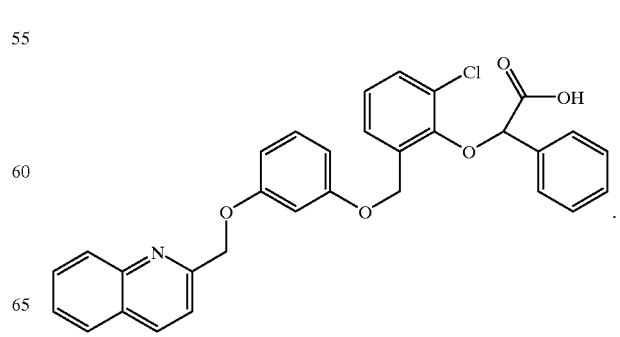

A preferred compound according to the invention is selected from the group consisting of
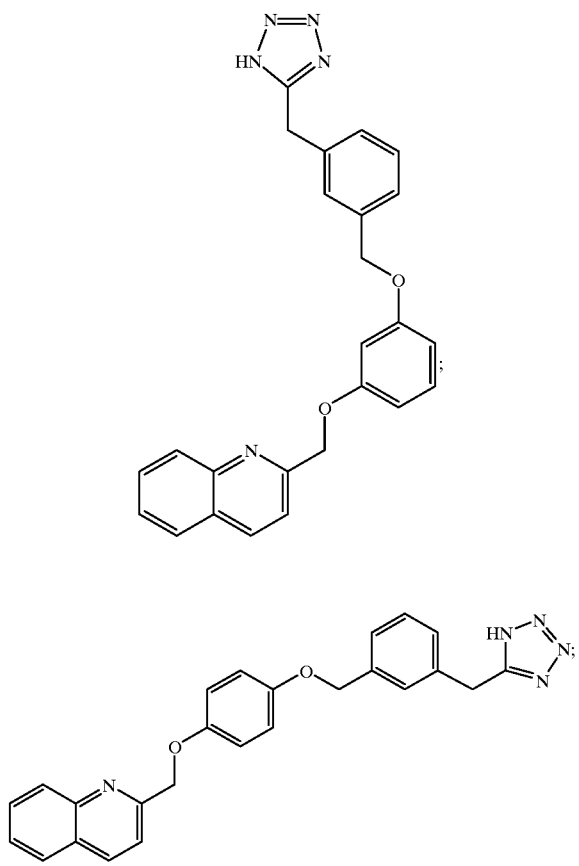
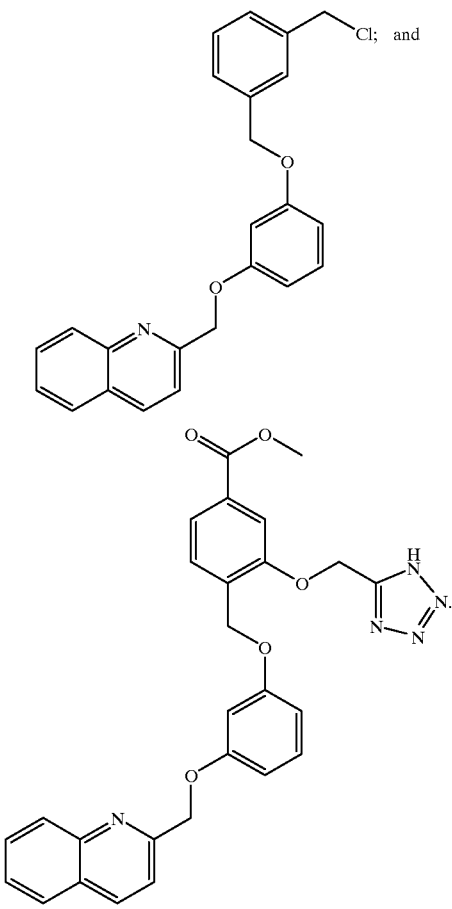
A more preferred compound has the formula:
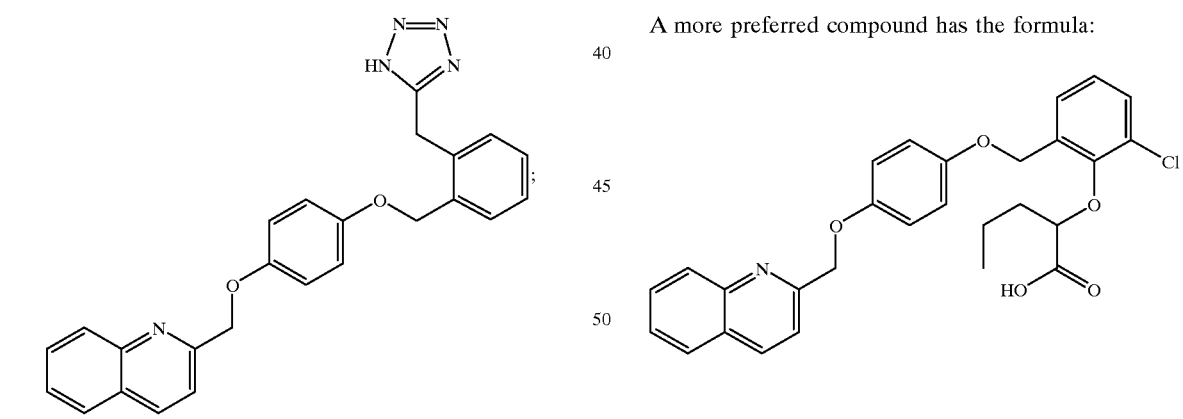
A more preferred compound has the formula VI:
(VI)
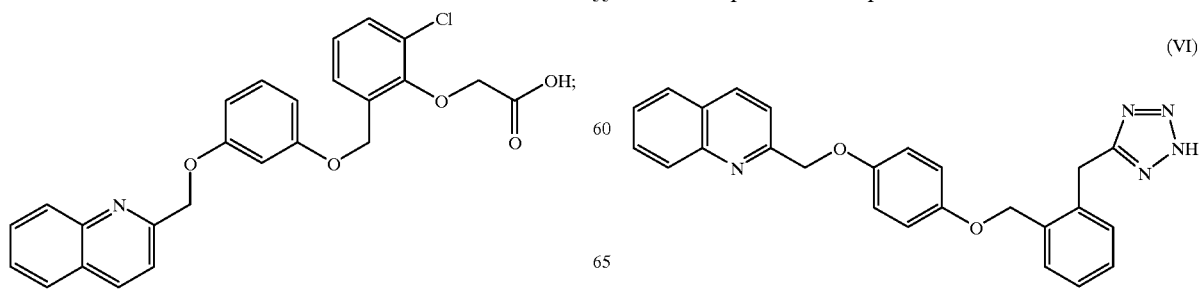

This invention also encompasses all combinations of preferred aspects of the invention noted herein.

Compounds useful according to this invention are preparable in segments as is common to a long chain molecule. Thus it is convenient to synthesize these molecules by employing condensation reactions at the A, B and D cites of the molecule. Compounds of formula I are preparable by the application or adaptation of known methods, by which is meant methods used heretofore or described in the literature. Thus, compounds of formula I are preparable by art recognized procedures from known compounds or readily preparable intermediates. Exemplary general procedures are as follows and are shown where R, R', $R_1$ and $R_2$ are all hydrogen; b, d and e are 0; a, c, and f are 1; or b, c, e and f are 0 and a and d are 1. B is O, S or $NR_1$ and Z is —CN, $COOR_1$ or tetrazolyl. Thus, in order to prepare the compound of the below formula

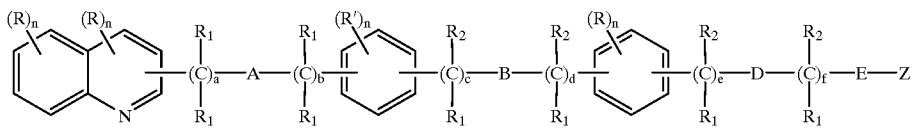

the following reactions or combinations of reactions are employable:

wherein:

R, R', $R_1$, $R_2$, a, b, c, d, e, f, n, A, and D are as defined above; B is O or S; E is a chemical bond; Z is —CN, —$COOR_1$ or tetrazol, and L is a leaving group, such as halo, tosylate, or mesylate. Where B is O or S, any base normally employed to deprotonate an alcohol or thiol may be used, such as sodium hydride, sodium hydroxide, triethylamine, sodium bicarbonate or diisopropyl/ethylamine.

Reaction temperatures are in the range of about room temperature to reflux and reaction times vary from about 2 to about 96 hours. The reaction is usually carried out in a solvent that will dissolve both reactants and is inert to both as well. Solvents include, but are not limited to, diethyl ether, tetrahydrofuran, N,N-dimethylformamide, dimethylsulfoxide, dioxane and the like.

In the case where B is SO or $SO_2$ then treatment of the thio compound with m-chlorobenzoic acid or sodium periodate results in the sulfinyl compound. Preparation of the sulfonyl compound may be accomplished by known proce-

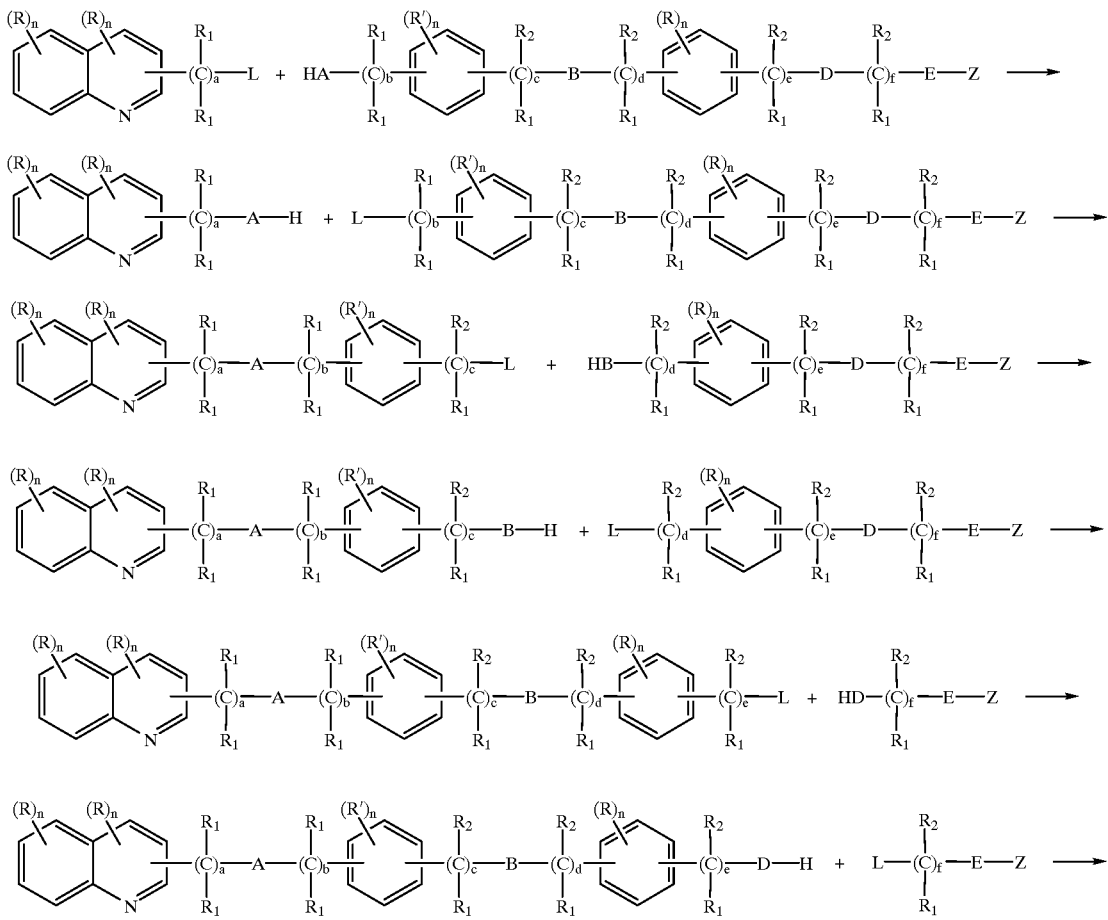

dures such as dissolving the sulfinyl compound in acetic acid and treating with 30% $H_2O_2$.

Those compounds where B is

may be prepared by the following reaction sequence:

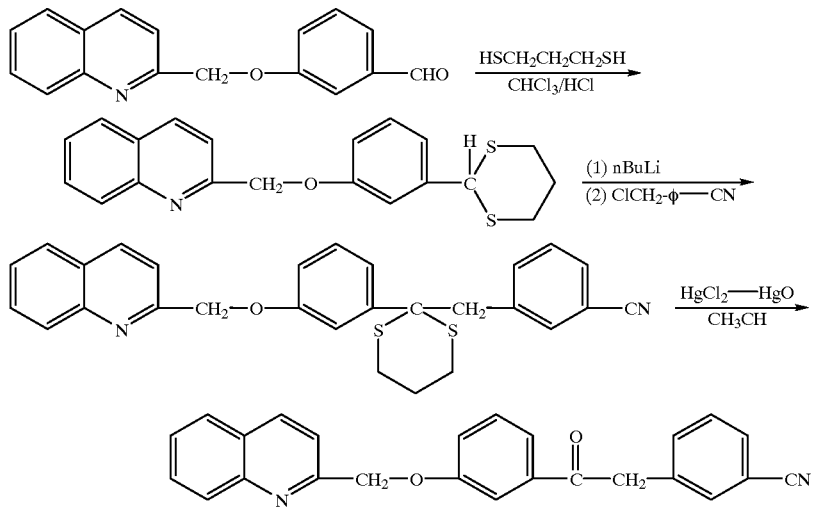

Condensation of the aldehyde with 1,3-propanedithiol results in the dithiane compound. This may be carried out in chloroform at reduced temperatures of about −20° C., while bubbling HCl gas into the reaction mixture. The dithiane compound is then treated with N-butyl lithium in nonpolar solvent at about −78° C. and then reacted with the substituted benzyl chloride. This results in addition of the Ring III to the molecule. The dithiane moiety is then treated with a mercuric chloride-mercuric oxide mixture to form the complex which is then split off leaving the desired compound.

Those compounds where B is

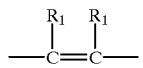

are prepared by reacting the appropriate aldehyde or ketone with a substituted Wittig reagent of the formula

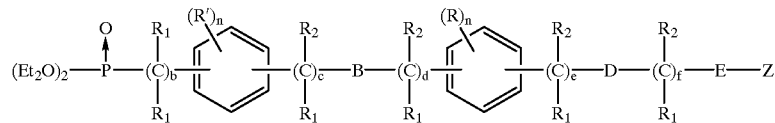

then condensation results in formation of the double bond. The Wittig reagent is prepared by known art recognized procedure such as reaction of triphenyl phosphine or diethylphosphone, with a suitable substituted alkyl/aryl bromide followed by treatment with a strong organometallic base such as n-BuLi or NaOH results in the desired ylide. Conventional Wittig reaction conditions may be used in accordance with standard practice, for examples see Best-mann and Vostrowsky, Top. Curr. Chem. 109, 85–164 (1983), and Pommer and Thieme, Top. Curr. Chem. 109, 165–188 (1983).

There is no particular restriction on the nature of the solvent to be employed, provided that it has no adverse effect on the reaction or on the reagents involved.

Of course this Wittig condensation may also take place when the Wittig reagent is formed on Ring I position of the molecule which is then condensed with the aldehyde from the Ring II portion.

Those compounds where A is a chemical bond may be prepared by known coupling methods, for example, the reaction of an appropriate alkyl halide with an appropriate organometallic reagent such as a lithium organocopper reagent (See Posner, Org. React. 22, 235–400 (1975), Normant, Synthesis 63–80 (1972), Posner, "An introduction to Synthesis Using Organocopper Reagents" pp68–81, Wiley, New York, 1980); coupling of an appropriate lithium organocopper reagent, or Grignard reagent, with a suitable ester of sulfuric or sulfonic acid (see "An introduction to Synthesis Using Organocopper Reagents" pp68–81, Wiley, New York, 1980, Kharasch and Reinmuth "Grignard Reactions of Non Metallic Substances", pp1277–1286, Prentice-Hall, Englewood Cliffs, N.J., 1954); or other known reactions for forming alkyl bonds (See March "Advanced Organic Chemistry" pp 1149, Third Edition, Wiley, NY, 1985).

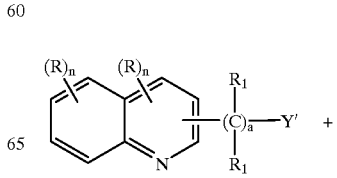

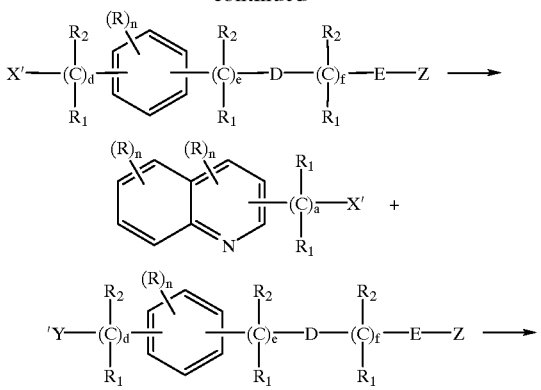

where X' is halide, an ester of a sulfuric acid, or a sulfonic ester, Y' is a lithium organocopper reagent or Grignard reagent.

There is no particular restriction on the nature of the nature of the reagent or solvent to be employed, provided that it has no adverse effect on the reaction or on the reagents involved.

Alternatively, compounds where A is a chemical bond may be prepared by reduction of appropriate compounds where A is

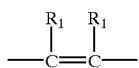

with a suitable reducing agent, for example $H_2/Pd/C$.

There is no particular restriction on the solvent or nature of the reducing agent to be used in this reaction, and any solvent and reducing agent conventionally used in reactions of this type may equally be used here, provided that it has no adverse effect on other parts of the molecule. An Example of a suitable reducing agent is $H_2/Pd/C$. Other reducing reagents are known in the art, for example, see: Mitsui and Kasahara, in Zabicky, "The Chemistry of Alkenes", vol. 2, pp. 175–214, Interscience, NY, 1970; and Rylander "Catalytic Hydrogenation over Platinum Metals", pp. 59–120, Academic Press, NY 1967.

Those compounds where B is

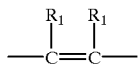

are prepared by reacting the appropriate aldehyde or ketone with a substituted Wittig reagent of the formula

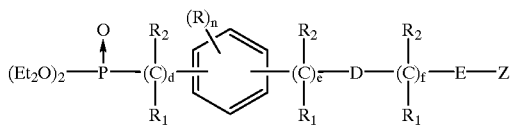

then condensation results in formation of the double bond. The Wittig reagent is prepared by known art recognized procedure such as reaction of triphenyl phosphine or diethylphosphone, with a suitable substituted alkyl/aryl bromide followed by treatment with a strong organometallic base such as n-BuLi or NaOH results in the desired ylide. Conventional Wittig reaction conditions may be used in accordance with standard practice, for examples see Bestmann and Vostrowsky, Top. Curr. Chem. 109, 85–164 (1983), and Pommer and Thieme, Top. Curr. Chem. 109, 165–188 (1983).

There is no particular restriction on the nature of the solvent to be employed, provided that it has no adverse effect on the reaction or on the reagents involved.

Of course this Wittig condensation may also take place when the Wittig reagent is formed on Ring II position of the molecule which is then condensed with the aldehyde from the Ring III portion.

Those compounds where B is a chemical bond may be prepared by known coupling methods, for example, the reaction of an appropriate alkyl halide with an appropriate organometallic reagent such as a lithium organocopper reagent (See Posner, Org. React. 22, 235–400 (1975), Normant, Synthesis 63–80 (1972), Posner, "An introduction to Synthesis Using Organocopper Reagents" pp68–81, Wiley, New York, 1980); coupling of an appropriate lithium organocopper reagent, or Grignard reagent, with a suitable ester of sulfuric or sulfonic acid (see "An introduction to Synthesis Using Organocopper Reagents" pp68–81, Wiley, New York, 1980, Kharasch and Reinmuth "Grignard Reactions of Non Metallic Substances", pp1277–1286, Prentice-Hall, Englewood Cliffs, N.J., 1954); or other known reactions for forming alkyl bonds (See March "Advanced Organic Chemistry" pp 1149, Third Edition, Wiley, NY, 1985).

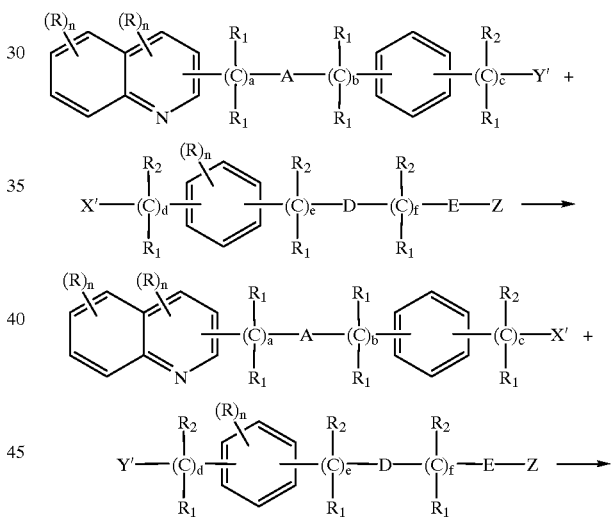

where X' is halide, an ester of a sulfuric acid, or a sulfonic ester, Y' is a lithium organocopper reagent or Grignard reagent.

There is no particular restriction on the nature of the nature of the reagent or solvent to be employed, provided that it has no adverse effect on the reaction or on the reagents involved.

Alternatively, compounds where B is a chemical bond may be prepared by reduction of appropriate compounds where B is

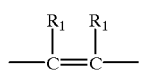

with a suitable reducing agent, for example $H_2/Pd/C$.

There is no particular restriction on the solvent or nature of the reducing agent to be used in this reaction, and any solvent and reducing agent conventionally used in reactions of this type may equally be used here, provided that it has no adverse effect on other parts of the molecule. An Example of a suitable reducing agent is H$_2$/Pd/C. Other reducing reagents are known in the art, for example, see: Mitsui and Kasahara, in Zabicky, "The Chemistry of Alkenes", vol. 2, pp. 175–214, Interscience, NY, 1970; and Rylander "Catalytic Hydrogenation over Platinum Metals", pp. 59–120, Academic Press, NY 1967.

There is no particular restriction on the nature of the solvent to be employed, provided that it has no adverse effect on the reaction or on the reagents involved.

The tetrazole may be formed from the nitrite at various stages of the synthesis by treatment with hydrazoic acid formed in situ from sodium azide and an acid.

When B is

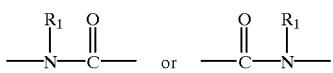

then condensation of the acid halide with the appropriate aniline will give the desired compound as shown below in the following scheme.

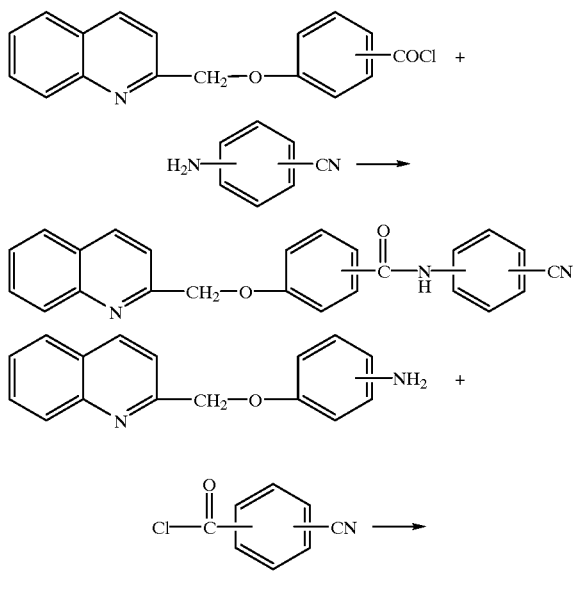

Those compounds where D and/or E are

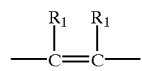

are prepared by reacting the appropriate aldehyde or ketone with a substituted Wittig reagent of the formula

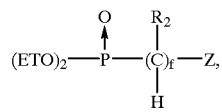

where Z is cyano or carbalkoxy. Reaction conditions would be similar to those for A and B above.

Those compounds where D and/or E are a chemical bond may also be synthesized by coupling methods similar to those for A and B above.

Compounds useful according to the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

According to a further feature of the present invention, compounds useful according to the invention may be prepared by interconversion of other compounds of the invention.

A compound of the invention including a group containing one or more nitrogen ring atoms, preferably imine (=N—), may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

The products of this invention may be obtained as racemic mixtures of their dextro and levorotatory isomers since at least one asymmetric carbon atom may be present. When two asymmetric carbon atoms are present the product may exist as a mixtures of diastereomers based on syn and anti configurations. These diastereomers may be separated by fractional crystallization. Each diastereomer may then be resolved into dextro and levorotatory optical isomers by conventional methods.

It will also be apparent to those skilled in the art that certain compounds of formula I may exhibit geometrical isomerism. Geometrical isomers include the cis and trans forms of compounds of the invention having an alkenyl moiety. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

Resolution may best be carried out in the intermediate stage where it is convenient to combine the racemic compound with an optically active compound by salt formation, ester formation, or amide formation to form two diastereomeric products. If an acid is added to an optically active base, then two diastereomeric salts are produced which possesses different properties and different solubilities and can be separated by fractional crystallization. When the salts have been completely separated by repeated crystallization, the base is split off by acid hydrolysis and enantiomerically purified acids are obtained.

Compounds useful according to the invention are useful in the form of the free base or acid or in the form of a pharmaceutically acceptable salt thereof. All forms are within the scope of the invention.

Where a compound useful according to the invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial pharmaceutical effects of these compounds in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts useful within the scope of the invention are those derived from the following acids: mineral acids such as hydrochloric acid, trifluoroacetic acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, trifluoroacetate, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

The acid addition salts of the compounds useful according to the invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds useful according to the invention may be regenerated from the acid addition salts by the application or adaptation of known methods. For example, parent compounds useful according to the invention can be regenerated from their acid addition salts by treatment with an alkali, e.g. aqueous sodium bicarbonate solution or aqueous ammonia solution.

Where the compound useful according to the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial pharmaceutical effects on the activity of the compounds of the present invention in the free acid are not vitiated by side effects ascribable to the cations. Pharmaceutically acceptable salts useful according to the invention, include for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, diethylamine, N-benzylphenethylamine, piperazine, tris(hydroxymethyl)aminomethane, tetramethylammonium hydroxide, and the like.

Metal salts of compounds useful according to the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds useful according to the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds useful according to the invention can be regenerated from the salts by the application or adaptation of known methods. For example, parent compounds useful according to the invention can be regenerated from their base addition salts by treatment with an acid, e.g. hydrochloric acid.

Salt forms useful according to the invention also include compounds having a quarternarized nitrogen. The quarternarized salts are formed by methods such as by alkylation of a $sp^3$ or $sp^2$ hybridized nitrogen in the compounds.

As will be self-evident to those skilled in the art, some of the compounds useful according to the invention do not form stable salts. However, acid addition salts are most likely to be formed by compounds useful according to the invention having a nitrogen-containing heteroaryl group and/or wherein the compounds contain an amino group as a substituent. Preferable acid addition salts of the compounds useful according to the invention are those wherein there is not an acid labile group.

As well as being useful in themselves as active compounds, the salts of the compounds useful according to the invention are useful for the purposes of purification of the compounds, for example by exploitation of the solubility differences between the salts and the parent compounds, side products and/or starting materials by techniques well known to those skilled in the art.

Various substituents on the compounds useful according to the invention, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The starting materials and intermediates are prepared by the application or adaptation of known methods, for example methods as described in the Reference Examples or their obvious chemical equivalents.

The present invention is further exemplified but not limited by the following examples which illustrate the preparation of the compounds according to the invention.

EXAMPLE 1

3-(2-QUINOLINYLMETHYLOXY)BENZYL ALCOHOL

A mixture of 12.8 g (0.06 mol) of 2-quinolinylmethyl chloride HCl, 7.5 g (0.06 mol) of 3-hydroxybenzyl alcohol, and 18 g of potassium carbonate in 50 ml of DMF is heated at 70° C. overnight. The reaction mixture is poured into water, and the precipitated product is collected, filtered and dried to give 3-(2-quinolinylmethyloxy)benzyl alcohol.

EXAMPLE 2

When 2-quinolinylmethyl chloride of Example 1 above is replaced by the quinoline compounds of Table I below then the corresponding product is obtained.

TABLE I 2-chloromethylquinoline
2-bromomethylquinoline
2-(1-chloroethyl)quinoline
2-(2-chloroethyl)quinoline
2-bromoethylquinoline
3-chloromethylquinoline
4-chloromethylquinoline
2-(β-chloroethyl)quinoline
2-(β-chloropropyl)quinoline
2-(β-chloro-β-phenethyl)quinoline
2-chloromethyl-4-methylquinoline
2-chloromethyl-6-methylquinoline
2-chloromethyl-8-methylquinoline
2-chloromethyl-6-methoxyquinoline TABLE I-continued 2-chloromethyl-6-nitroquinoline
2-chloromethyl-6,8-dimethylquinoline

EXAMPLE 3

When 3-hydroxybenzyl alcohol of Example 1 above is replaced by the compounds of Table II below then the corresponding product is obtained.

TABLE II 1,2-benzenediol
1,3-benzenediol
1,4-benzenediol
2-mercaptophenol
3-mercaptophenol
4-mercaptophenol
1,3-dimercaptobenzene
1,4-dimercaptobenzene
3-hydroxybenzyl alcohol
3-hydroxyethylphenol
4-hydroxybenzyl alcohol
4-hydroxyethylphenol
2-methylresorsinol
5-methylresorsinol
5-methoxyresorsinol
5-methyl-1,4-dihydroxybenzene
3-(N-acetylamino)phenol
3-(N-acetylamino)benzyl alcohol
2-hydroxy-α-methylbenzyl alcohol
2-hydroxy-α-ethylbenzyl alcohol
2-hydroxy-α-propylbenzyl alcohol
3-hydroxy-α-methylbenzyl alcohol
3-hydroxy-α-ethylbenzyl alcohol
3-hydroxy-α-propylbenzyl alcohol
4-hydroxy-α-methylbenzyl alcohol
4-hydroxy-α-ethylbenzyl alcohol
4-hydroxy-α-propylbenzyl alcohol

EXAMPLE 4

When the compounds of Table I, Example 2 are reacted with the compounds of Table II, Example 3 under the conditions of Example 1 then the corresponding products are obtained.

EXAMPLE 5

3-(2-QUINOLINYLMETHYLOXY)BENZYL CHLORIDE

To a stirred solution of 14.5 g of 3-(2-quinolinylmethyloxy)benzyl alcohol in 150 ml of CHCl$_3$ is added dropwise 7.5 ml of thionyl chloride during 10 min. The reaction mixture is stirred for 4 hours at room temperature, and then washed with NaHCO$_3$ solution. The organic solution is separated, dried, and evaporated to give 3-(2-quinolinylmethyloxy)benzyl chloride which is used without further purification in the next step.

EXAMPLE 6

When the compounds prepared by Examples 2–4 are used in place of 3-(2-quinolinylmethyloxy)benzyl alcohol in Example 5, then the corresponding chloride is prepared.

EXAMPLE 7

3-[3-(2-QUINOLINYLMETHYLOXY) BENZYLOXY]BENZONITRILE

A solution of 0.65 g (5.4 mmol) 3-hydroxybenzonitrile, 1.5 g (5.3 mmol) of 3-(2-quinolinylmethyloxy)benzyl chloride, and 0.75 g (5.4 mmol) of potassium carbonate in 15 ml of DMF is heated at 60° C. overnight. The reaction mixture is poured into water. The precipitated product is collected on a filter and purified by dry column chromatography to give 3-[3-(2-quinolinylmethyloxy)benzyloxy] benzonitrile. (MP 86–87° C.)

EXAMPLE 8

When 3-hydroxybenzonitrile of Example 7 above is replaced by the compounds of Table III below then the corresponding product is obtained.

TABLE III 2-hydroxybenzonitrile
3-hydroxybenzonitrile
4-hydroxybenzonitrile
2-cyanomethylphenol
3-cyanomethylphenol
4-cyanomethylphenol
2-cyanoethylphenol
3-cyanoethylphenol
4-cyanoethylphenol
2-cyanopropylphenol
3-cyanopropylphenol
4-cyanopropylphenol
3-cyanobutylphenol
4-cyanobutylphenol
2-methyl-3-hydroxybenzonitrile
4-methyl-3-hydroxybenzonitrile
5-methyl-3-hydroxybenzonitrile
2-methyl-4-hydroxybenzonitrile
3-methyl-4-hydroxybenzonitrile
5-methyl-4-hydroxybenzonitrile
4-methoxy-3-hydroxybenzonitrile
3-methoxy-4-hydroxybenzonitrile
2-methoxy-4-hydroxybenzonitrile
2-methoxy-4-hydroxybenzonitrile
4-carbomethoxy-3-hydroxybenzonitrile
5-carbomethoxy-3-hydroxybenzonitrile
3-carbomethoxy-4-hydroxybenzonitrile
2,5-dimethyl-4-hydroxybenzonitrile
3-methyl-4-cyanomethylphenol
2-methyl-4-cyanomethylphenol
2-methyl-3-cyanomethylphenol
4-methyl-3-cyanomethylphenol
5-methyl-3-cyanomethylphenol
2-mercaptobenzonitrile
3-mercaptobenzonitrile
4-mercaptobenzonitrile
3-mercaptobenzylnitrile
4-mercaptobenzylnitrile
4-methyl-3-mercaptobenzonitrile
2-cyanomethyl-1-hydroxymethylbenzene
3-cyanomethyl-1-hydroxymethylbenzene
4-cyanomethyl-1-hydroxymethylbenzene
2-hydroxymethylbenzonitrile
3-hydroxymethylbenzonitrile
4-hydroxymethylbenzonitrile
3-(N-acetylamino)benzonitrile
4-(N-acetylamino)benzonitrile

EXAMPLE 9

When the compounds of Example 6 are used in place of 3-(2quinolinylmethyloxy)benzyl chloride in Examples 7 and 8 then the corresponding nitriles are obtained.

EXAMPLE 10

5-[3-(3-(2-QUINOLINYLMETHYLOXY) BENZYLOXY)PHENYL]TETRAZOLE

A mixture of 1.2 g (3.28 mmol) of 3-[3-(2-quinolinylmethyloxy)benzyloxy]benzonitrile, 1.89 g (16.4 mmol) of pyridine hydrochloride, and 1.06 g (16.4 mmol) of sodium azide in 10 ml of DMF is heated at 100° C. for 4 days. The reaction mixture is poured into water. The crude product collected on a filter and recrystallized from ethyl acetate to give 5-[3-(3-(2-quinolinylmethyloxy)benzyloxy) phenyl]tetrazole. (M.P. 169–172° C.)

EXAMPLE 11

When 4-hydroxybenzyl alcohol is used in place of 3-hydroxybenzyl alcohol in Example 1 and 4-hydroxybenzonitrile is used in place of 3-hydroxybenzonitrile in Example 7 then the product obtained is 5-[4-(4-(2-quinolinylmethyloxy)benzyloxy) phenyl]tetrazole. (M.P. 210–213° C.)

EXAMPLE 12

When 4-cyanomethylphenol is used in place of 4-hydroxybenzonitrile in Example 11 then the product obtained is 5-[4(4-(2-quinolinylmethyloxy)benzyloxy) benzyl]tetrazole. (M.P. 179–181° C.)

EXAMPLE 13

When the nitrile compounds of Example 9 are used in place of 3-[3-(2-quinolinylmethyloxy)benzyloxy] benzonitrile in Example 10 the corresponding tetrazole product is obtained. Representative examples of compounds obtained by this invention are shown in Table IV below.

TABLE IV

5-[3-(4-(2-quinolinylmethyloxy)benzyloxy)phenyl]tetrazole
5-[2-(4-(2-quinolinylmethyloxy)benzyloxy)phenyl]tetrazole
5-[4-(3-(2-quinolinylmethyloxy)benzyloxy)phenyl]tetrazole
5-[4-(2-(2-quinolinylmethyloxy)benzyloxy)phenyl]tetrazole
5-[2-(3-(2-quinolinylmethyloxy)benzyloxy)phenyl]tetrazole
5-[3-(3-(2-quinolinylmethyloxy)benzyloxy)benzyl]tetrazole
5-[4-(3-(2-quinolinylmethyloxy)benzyloxy)benzyl]tetrazole
5-[3-(4-(2-quinolinylmethyloxy)benzyloxy)benzyl]tetrazole
5-[2-(3-(2-quinolinylmethyloxy)benzyloxy)benzyl]tetrazole
5-[4-(2-(2-quinolinylmethyloxy)benzyloxy)benzyl]tetrazole
5-[2-(4-(2-quinolinylmethyloxy)benzyloxy)benzyl]tetrazole
5-[2-(3-(4-(2-quinolinylmethyloxy)benzyloxy)phenyl)propyl]tetrazole
5-[2-(3-(4-(2-quinolinylmethyloxy)benzyloxy)phenyl)butyl]tetrazole
5-[3-(3-(4-(2-quinolinylmethyloxy)benzyloxy)phenyl)butyl]tetrazole
5-[3-(3-(2-quinolinylmethylthio)benzyloxy)phenyl]tetrazole
5-[3-(3-(2-quinolinylmethylthio)benzylthio)phenyl]tetrazole
5-[3-(3-(2-quinolinylmethyloxy)benzylthio)phenyl]tetrazole
5-[4-(3-(2-quinolinylmethyloxy)benzyloxy)-3-methoxyphenyl]tetrazole
5-[3-(3-(2-quinolinylmethyloxy)benzyloxy)-4-methoxyphenyl]tetrazole
5-[4-(2-(2-quinolinylmethyloxy)benzyloxy)-3-methoxyphenyl]tetrazole
5-[3-(4-(2-quinolinylmethyloxy)benzyloxy)-4-methoxyphenyl]tetrazole
5-[4-(3-(2-quinolinylmethyloxy)benzyloxy)-2-methoxyphenyl]tetrazole
5-[4-(3-(2-quinolinylmethyloxy)benzyloxy)-3-carbomethoxyphenyl] tetrazole
5-[4-(3-(2-quinolinylmethyloxyjbenzyloxy)-3-methoxybenzyl]tetrazole
5-[4-(4-(2-quinolinylmethyloxy)benzyloxy)-3-methoxybenzyl]tetrazole
5-[4-(4-(2-quinolinylmethyloxy)benzyloxy)-3-carbomethoxybenzyl] tetrazole
5-[4-(3-(2-quinolinylmethyloxy)benzyloxy)-3-carbomethoxybenzyl] tetrazole
5-[4-(3-(2-quinolinylmethyloxy)benzylthio)phenyl]tetrazole
5-[3-(4-(2-quinolinylmethyloxy)benzylthio)phenyl]tetrazole
5-[4-(3-(2-quinolinylmethyloxy)-N-acetyl-benzylamino)phenyl]tetrazole
5-[4-(4-(2-quinolinylmethyloxy)-N-acetyl-benzylamino)phenyl]tetrazole

EXAMPLE 14

METHYL 3-METHOXY-4-[3-(2-QUINOLINYLMETHYLOXY)BENZYLOXY]-BENZOATE

A mixture of 3 g of 3-(2-quinolinylmethyloxy) benzyl chloride, 1.93 g of methyl 4-hydroxy-3-methoxy benzoate, and 1.5 g of potassium carbonate in 30 ml of DMF is heated at 50° C. overnight. The reaction mixture is poured into water, the solid product collected on a filter and purified by dry column chromatography to give methyl 3-methoxy-4-(3-(2quinolinylmethyloxy)benzyloxy)-benzoate. (M.P. 100–101° C.)

EXAMPLE 15

3-METHOXY-4-[3-(2-QUINOLINYLMETHYLOXY)BENZYLOXY]-BENZOIC ACID

A mixture of 2.6 g of methyl 3-methoxy-4-[3-(2-quinolinylmethyloxy)benzyloxy]benzoate and 0.6 g of NaOH in 15 ml of THF and 2 ml of H₂O are heated at 60° C. overnight. The reaction mixture is diluted with 20 ml of H₂O and acidified to pH 4. The product is collected on a filter and dried to give 3-methoxy-4-(3-(2-quinolinylmethyloxy)benzyloxy)benzoic acid. (M.P. 188–190° C.)

EXAMPLE 16

When methyl 4-hydroxy-3-methoxybenzoate is replaced in the procedure of Example 14 with the compounds of Table V, below, then the corresponding products are obtained. Representative examples of compounds prepared by this invention are shown in Table VI.

TABLE V methyl 2-hydroxybenzoate
methyl 3-hydroxybenzoate
methyl 4-hydroxybenzoate
methyl 4-hydroxy-3-methoxybenzoate
methyl 3-hydroxy-4-methoxybenzoate
methyl 4-hydroxy-2-methoxybenzoate
methyl 3-hydroxy-4-methoxybenzoate
ethyl 4-hydroxy-3-ethoxybenzoate
methyl 4-hydroxy-3-methylbenzoate
methyl 3-hydroxy-4-methylbenzoate
methyl 4-hydroxy-2-methylbenzoate
methyl 3-hydroxy-4-methylbenzoate
methyl 4-hydroxy-2,6-dimethylbenzoate
methyl 4-hydroxy-2,5-dimethylbenzoate
methyl 2-hydroxyphenylacetate
methyl 3-hydroxyphenylacetate
methyl 4-hydroxyphenylacetate
methyl 4-hydroxyphenylpropionate
methyl 4-hydroxyphenylbutyrate
methyl 4-hydroxyphenyl-3-methylbutyrate
methyl 4-hydroxy-3-methylphenylacetate
methyl 3-hydroxy-4-methylphenytacetate
methyl 4-hydroxy-3-methoxyphenylacetate
methyl 3-hydroxy-4-methoxyphenylacetate
methyl 2-hydroxymethylbenzoate
methyl 3-hydroxymethylbenzoate
methyl 4-hydroxymethylbenzoate
methyl 2-hydroxymethylphenylacetate
methyl 3-hydroxymethylphenylacetate
methyl 4-hydroxymethylphenylacetate
3-mercaptobenzoate
4-mercaptobenzoate
3-mercaptomethylbenzoate
3-(N-acetylamino)benzoate
4-(N-acetylamino)benzoate
4-(N-benzylamino)benzoate

TABLE VI 4-(3-(2-quinolinylmethyloxy)benzyloxy)benzoic acid
4-(4-(2-quinolinylmethyloxy)benzyloxy)benzoic acid

TABLE VI-continued 3-(4-(2-quinolinylmethyloxy)benzyloxy)benzoic acid
3-(3-(2-quinolinylmethyloxy)benzyloxy)benzoic acid
2-(4-(2-quinolinylmethyloxy)benzyloxy)benzoic acid 4-(3-(2-quinolinylmethyloxy)benzyloxy)phenylacetic acid 4-(3-(2-quinolinylmethyloxy)phenoxy)benzoic acid
4-(3-(2-quinolinylmethyloxy)benzyloxymethyl)benzoic acid
3-methyl-4-(3-(2-quinolinylmethyloxy)benzyloxy)benzoic acid
4-methyl-3-(3-(2-quinolinylmethyloxy)benzyloxy)benzoic acid
2-methyl-4-(3-(2-quinolinylmethyloxy)benzyloxy)benzoic acid
3-methoxy-4-(3-(2-quinolinylmethyloxy)benzyloxy)benzoic acid
4-methoxy-3-(3-(2-quinolinylmethyloxy)benzyloxy)benzoic acid
2,6-dimethyl-4-(3-(2-quinolinylmethyloxy)benzyloxybenzoic acid
4-(3-(2-quinolinylmethyloxy)benzylthio)benzoic acid 4-(3-(2-quinolinylmethyloxy)benzylamino)benzoic acid

EXAMPLE 17

3-METHOXY-4-(3-(2-QUINOLINYLMETHYLOXY)PHENOXYMETHYL)BENZOYL-N-BENZENESULFONAMIDE

A reaction mixture of 0.73 g of 3-methoxy-4-(3-(2quinolinyl-methyloxy)phenoxy)benzoic acid, 0.28 g of benzenesulfonamide, 0.28 g of 4-dimethylpyridine, and 0.44 g of 1-(3-dimethylamino-propyl)-3-ethylcarbodimide hydrochloride in 50 ml of CH₂Cl₂ is stirred at room temperature overnight. The solvent is removed and the residue is extracted into ethyl acetate. The organic solution is washed with water, and evaporated. The product is purified by dry column chromatography to give 3-methoxy-4-(3-(2quinolinylmethyloxy) phenoxymethyl)benzoyl-N-benzenesulfonamide. (M.P. 156–158° C.)

EXAMPLE 18

When 3-methoxy-4-(3-(2-quinolinylmethyloxy) phenoxymethyl)benzoic acid of Example 17 is replaced by the acids of this invention such as those of Example 16, Table VI and Example 25, Table IX then the corresponding benzenesulfonamide compound is prepared.

When benzenesulfonamide is replaced in the above Examples by a sulfonamide of the formula NH₂SO₂R₃ or an amine of the formula HN(R₁)₂, then the corresponding product is obtained.

EXAMPLE 19

METHYL 3-(3-(2-QUINOLINYLMETHYLOXY)PHENOXYMETHYL)BENZOATE

A mixture of 3-(2-quinolinylmethyloxy)phenol (2.51 g, 0.01 mol), 1.85 g (0.01 mol) of methyl 3-chloromethyl benzoate, and 1.5 g of potassium carbonate in 30 ml of DMS is heated at 50° C. overnight. The reaction mixture is poured into water, extracted with ethyl acetate and the organic solution separated, dried and evaporated to dryness. Recrystallization from ethyl acetate gives methyl 3-(3-(2-quinolinylmethyloxy)phenoxymethyl)benzoate. (M.P. 93–94° C.)

EXAMPLE 20

A mixture of 1.6 g of methyl 3-(3-(2-quinolinylmethyloxy)phenoxymethyl)benzoate and 0.5 g of NaOH in 20 ml of THF and 5 ml of H₂O is heated at 50° C. overnight. The reaction mixture is acidified to pH 4 by 1N HCl solution, filtered and dried to give 3-(3-(2-quinolinylmethyloxy)phenoxymethyl)benzoic acid. (M.P. 149–151° C.)

EXAMPLE 21

When the procedures of Examples 19 and 20 are followed and methyl 3-chloromethylbenzoate is replaced by methyl 4-chloromethylbenzoate, then the product prepared is 4-(3-(2-quinolinylmethyloxy)phenoxymethyl)benzoic acid. (M.P. 190–191° C.)

EXAMPLE 22

When the procedures of Examples 19 and 20 are followed and methyl 3-chloromethylbenzoate is replaced by methyl 3-methoxy-4-chloromethylbenzoate then the product prepared is 3-methoxy-4-(3-(2-quinolinylmethyloxy)phenoxymethyl)benzoic acid. (M.P. 208–210° C.)

EXAMPLE 23

When the procedure of Example 19 is followed and the compounds of Table VII below are used in place of methyl-3-chloromethyl-benzoate then the corresponding product is obtained.

TABLE VII ethyl 2-chloromethylbenzoate
ethyl 3-chloromethylbenzoate
ethyl 4-chloromethylbenzoate
ethyl 3-chloromethylbenzoate
methyl 4-chloromethylbenzoate
methyl 2-methyl-5-chloromethylbenzoate
methyl 2-methyl-3-chloromethylbenzoate
methyl 3-methyl-5-chloromethylbenzoate
methyl 4-methyl-5-chloromethylbenzoate
methyl 2-methyl-4-chloromethylbenzoate
methyl 3-methyl-4-chloromethylbenzoate
methyl 2-methoxy-5-chloromethylbenzoate
methyl 2-methoxy-3-chloromethylbenzoate
methyl 2-methoxy-4-chloromethylbenzoate
methyl 3-methoxy-4-chloromethylbenzoate
methyl 3-chloromethylphenylacetate
methyl 4-chloromethylphenylacetate
methyl 3-chloromethylphenylpropionate
methyl 4-chloromethylphenylpropionate
methyl 3-chloromethylphenylbutyrate
methyl 4-chloromethylphenylbutyrate
methyl 3-chloromethylphenylisopropionate
methyl 4-chloromethylphenylisopropionate
methyl 3-chloromethylphenylisopropionate
methyl 4-chloromethylphenylisobutyrate

EXAMPLE 24

When the procedure of Example 19 is followed and the compound of Table VIII below are used in place of 3-(2quinolinyl-methyloxy)phenol then the corresponding product is obtained.

TABLE VIII 3-(2-quinolinylmethyloxy)phenol
4-(2-quinolinylmethyloxy)phenol
3-(2-quinolinylmethylthio)phenol
4-(2-quinolinylmethylthio)phenol
5-methyl-3-(2-quinolinylmethyloxy) phenol
2-methyl-3-(2-quinolinylmethyloxy)phenol
5-methoxy-3-(2-quinolinylmethyloxy)phenol
2-methyl-4-(2-quinolinylmethyloxy)phenol
2-methoxy-4-(2-quinolinylmethyloxy)phenol
3-methoxy-4-(2-quinolinylmethyloxy)phenol
3-methyl-4-(2-quinolinylmethyloxy)phenol
3-(2-quinolinylmethyloxy)phenyl mercaptan
4-(quinolinylmethyloxy)phenyl mercaptan
3-(2-quinolinylmethylthio)phenyl mercaptan

TABLE VIII-continued 4-(2-quinolinylmethylthio)phenyl mercaptan
N-benzyl-3-(2-quinolinylmethyloxy)phenylamine
N-methyl-3-(2-quinolinylmethyloxy)phenylamine
N-acetyl-3-(2-quinolinylmethyloxy)phenylamine
N-acetyl-4-(2-quinolinylmethyloxy)phenylamine

EXAMPLE 25

When the procedures of Examples 19 and 20 are followed using the compounds of Table VII, Example 23 and Table VIII, Example 24, then the corresponding product is obtained. Representative examples of compounds prepared by this invention are shown in Table IX.

TABLE IX 3-(4-(2-quinolinylmethyloxy)phenoxymethyl)benzoic acid
4-(4-(2-quinolinylmethyloxy)phenoxymethyl)benzoic acid
2-(3-(2-quinolinylmethyloxy)phenoxymethyl)benzoic acid
2-(4-(2-quinolinylmethyloxy)phenoxymethyl)benzoic acid
2-methyl-3-(3-(2-quinolinylmethyloxy)phenoxymethyl)benzoic acid
2-ethyl-3-(3-(2-quinolinylmethyloxy)phenoxymethyl)benzoic acid
2-methoxy-3-(3-(2-quinolinylmethyloxy)phenoxymethyl)benzoic acid
3-methyl-4-(3-(2-quinolinylmethyloxy)phenoxymethyl)benzoic acid
2-methyl-4-(3-(2-quinolinylmethyloxy)phenoxymethyl)benzoic acid
2-methoxy-4-(3-(2-quinolinylmethyloxy)phenoxymethyl)benzoic acid
3-(3-(2-quinolinylmethyloxy)-5-methylphenoxymethyl)benzoic acid
3-(3-(2-quinolinylmethyloxy)-5-methoxyphenoxymethyl)benzoic .acid
3-(4-(2-quinolinylmethyloxy)-3-methylphenoxymethyl)benzoic acid
3-(4-(2-quinolinylmethyloxy)-2-methylphenoxymethyl)benzoic acid
2-methyl-3-(3-(2-quinolinylmethyloxy)-2-methylphenoxymethyl)benzoic acid
3-(3-(2-quinolinylmethylthio)phenoxymethyl)benzoic acid
4-(4-(2-quinolinylmethylthio)phenoxymethyl)benzoic acid
3-(3-(2-quinolinylmethyloxy)phenoxymethyl)phenylacetic acid
3-(3-(2-quinolinylmethyloxy)phenoxymethyl)phenylpropionic acid
3-(3-(2-quinolinylmethyloxy)phenylthiomethyl)benzoic acid
4-(3-(2-quinolinylmethyloxy)phenylthiomethyl)benzoic acid
3-(4-(2-quinolinylmethyloxy)phenylthiomethyl)benzoic acid
3-(3-(2-quinolinylmethyloxy)phenyl-N-acetylamino-methyl)benzoic acid
4-(4-(2-quinolinylmethyloxy)phenyl-N-acetylaminomethyl)benzoic acid

EXAMPLE 26

4-(3-(2-QUINOLINYLMETHYLOXY) PHENOXYMETHYL)BENZONITRILE

A solution of 7.24 g (19.92 mmol) of sodium 3-(2quinolinylmethyloxy)phenoxide pentahydrate and 4.68 g (23.90 mmol) of p-cyanobenzyl bromide in 34 ml of dry DMF is stirred at 75° C. under nitrogen for 2 days. The reaction mixture is cooled to room temperature, then poured into 400 ml of 3:1 $H_2O/Et_2O$, shaken; and the phases separated. The aqueous layer is extracted and washed with 1:1 brine/$H_2O$ and brine. The ether solution is dried over 1:1 $Na_2SO_4MgSO_4$, filtered and concentrated. The crude product is recrystallized from 70% EtOAc/hexane to obtain 4-(3-(2quinolinylmethyloxy)phenoxy-methyl)benzonitrile. (M.P. 112.5° C.)

EXAMPLE 27

5-(4-(3-(2-QUINOLINYLMETHYLOXY) PHENOXYMETHYL)PHENYL)TETRAZOLE

A slurry of 2.0 g (5.48 mol) of 4-(3-(2-quinolinylmethyloxy)phenoxymethyl)benzonitrile, 1.78 g (27.4 mmol) of sodium azide, and 3.16 g (27.4 mmol) of pyridinium hydrochloride in 12 ml of dry DMF is stirred under nitrogen at 100° C. for 20 hrs. The reaction mixture is then cooled to room temperature and concentrated. The residue is taken up on 100 ml of 1N aqueous NaOH and the solution extracted with ether. The aqueous layer is acidified to pH 6 with 1N aqueous HCl, and the precipitate collected, triturated with water, filtered and lyophilized to obtain 5-(4-(3-(2quinolinylmethyloxy)phenoxy-methyl)phenyl) tetrazole. (M.P. 91° C. dec.)

EXAMPLE 28

When the procedures of Examples 26 and 27 are followed and p-cyanobenzyl bromide is replaced by o-cyanobenzyl bromide, m-cyanobenzyl bromide, o-(cyanomethyl)benzyl bromide, m(cyanomethyl)benzyl bromide, p-(cyanomethyl)-benzyl bromide, then the products prepared are:
5-(2-(3-(2-quinolinylmethyloxy)phenoxymethyl)phenyl) tetrazole (M.P. 166–170° C.);
5(3-(3-(2-quinolinylmethyloxy)phenoxymethyl)phenyl) tetrazole (M.P. 115° C. dec.);
5-(2-(3-(2-quinolinylmethyloxy)phenoxymethyl)benzyl) tetrazole (M.P. 145.5–147C.);
5-3-(3-(2-quinolinylmethyloxy)phenoxymethyl)benzyl) tetrazole (M.P. 161–164° C.); and
5-(4-(3-(2-quinolinylmethyloxy)phenoxymethyl)benzyl) tetrazole (M.P. 149–152° C.).

EXAMPLE 29

When the procedure of Example 26 is followed and compounds of Table X below are used in place of p-cyanobenzyl bromide then the corresponding product is obtained.

TABLE X 2-methyl-4-cyanobenzyl bromide
3-methyl-4-cyanobenzyl bromide
3-methoxy-2-cyanobenzyl bromide
2-methyl-3-cyanobenzyl bromide
3-cyano-4-methylbenzyl bromide
4-methoxy-2-cyanobenzyl bromide
3-cyano-5-methylbenzyl bromide
2-methyl-5-cyanobenzyl bromide
2-methoxy-5-cyanobenzyl bromide
2-methoxy-4-cyanobenzyl bromide
2-methoxy-3-cyanobenzyl bromide
2,6-dimethyl-4-cyanobenzyl bromide
3-methoxy-4-cyanobenzyl bromide
2-methyl-6-cyanobenzyl bromide
o-cyanobenzyl bromide
m-cyanobenzyl bromide
p-cyanobenzyl bromide
2-cyanomethylbenzyl bromide
3-cyanomethylbenzyl bromide
4-cyanomethylbenzyl bromide
3-(1'-cyanoethyl)benzyl bromide
3-(2'-cyanoethyl)benzyl bromide
4-(1'-cyanoethyl)benzyl bromide
4-(2'-cyanoethyl)benzyl bromide
3-(1'-cyanopropyl)benzyl bromide
3-(2'-cyanopropyl)benzyl bromide
3-(3'-cyanopropyl)benzyl bromide
4-(1'-cyanopropyl)benzyl bromide
4-(2'-cyanopropyl)benzyl bromide
4-(3'-cyanopropyl)benzyl bromide
3-(1'-cyanobutyl)benzyl bromide
3-(2'-cyanobutyl)benzyl bromide
3-(3'-cyanobutyl)benzyl bromide
3-(4'-cyanobutyl)benzyl bromide
4-(1'-cyanobutyl)benzyl bromide
4-(2'-cyanobutyl)benzyl bromide
4-(3'-cyanobutyl)benzyl bromide
4-(4'-cyanobutyl)benzyl bromide
3-(2'-methyl-1'-cyanobutyl)benzyl bromide TABLE X-continued 3-(3'-methyl-1'-cyanobutyl)benzyl bromide
4-(2'-methyl-1'-cyanobutyl)benzyl bromide
4-(3'-methyl-1'-cyanobutyl)benzyl bromide

EXAMPLE 30

When the procedure of Example 26 is followed and the sodium or other appropriate salt of the alcohol or mercaptan of Table VIII, Example 24 is used is place of sodium 3-(2-quinolinylmethyloxy)-phenoxide then the corresponding product is obtained.

EXAMPLE 31

When the procedures of Examples 26 and 27 are followed using the compounds of Table X, Example 29 and the appropriate alcohol, thio or amino salt formed in Example 30, then the corresponding products are obtained. Representative examples of compounds prepared by this invention are shown in Table XI.

TABLE XI 5-(4-(4-(2-quinolinylmethyloxy)phenoxymethyl)phenyl)tetrazole
5-(3-(4-(2-quinolinylmethyloxy)phenoxymethyl)phenyl)tetrazole
5-(3-(2-(2-quinolinylmethyloxy)phenoxymethyl)phenyl)tetrazole
5-(2-(4-(2-quinolinylmethyloxy)phenoxymethyl)phenyl)tetrazole
5-(4-(2-(2-quinolinylmethyloxy)phenoxymethyl)phenyl)tetrazole
5-(2-(2-(2-quinolinylmethyloxy)phenoxymethyl)phenyl)tetrazole
5-(3-(3-(2-quinolinylmethyloxy)phenoxymethyl)phenyl)tetrazole
5-(4-(3-(2-quinolinylmethyloxy)-5-methoxyphenoxymethyl)phenyl) tetrazole
5-(4-(3-(2-quinolinylmethyloxy)-5-methylphenoxymethyl)phenyl) tetrazole
5-(3-(4-(2-quinolinylmethyloxy)-2-methylphenoxymethyl)phenyl) tetrazole
5-(3-(4-(2-quinolinylmethyloxy)-2-methoxyphenoxymethyl)phenyl) tetrazole
5-(4-(3-(2-quinolinylmethyloxy)-2-methylphenoxymethyl)phenyl) tetrazole
5-(4-(4-(2-quinolinylmethyloxy)-2-methylphenoxymethyl)phenyl) tetrazole
5-(4-(4-(2-quinolinylmethyloxy)-3-methylphenoxymethyl)phenyl) tetrazole
5-(4-(3-(2-quinolinylmethylthio)phenoxymethyl)phenyl)tetrazole
5-(3-(3-(2-quinolinylmethylthio)phenoxymethyl)phenyl)tetrazole
5-(2-(3-(2-quinolinylmethylthio)phenoxymethyl)phenyl)tetrazole
5-(2-(4-(2-quinolinylmethyloxy)phenoxymethyl)benzyl)tetrazole
5-(4-(4-(2-quinolinylmethyloxy)phenoxymethyl)benzyl)tetrazole
5-(3-(4-(2-quinolinylmethyloxy)phenoxymethyl)benzyl)tetrazole
5-(4-(3-(2-quinolinylmethyloxy)phenoxymethyl)phenethyl)tetrazole
5-(3-(2-(4-(2-quinolynylmethyloxy)phenoxymethyl)phenyl)propyl) tetrazole
5-(4-(3-(2-(2-quinolynylmethyloxy)phenoxymethyl)phenyl)butyl)tetrazole
5-(2-(4-(3-(2-quinolynylmethyloxy)phenoxymethyl)phenyl)propyl) tetrazole
5-(3-(4-(3-(2-quinolinylmethyloxy)phenoxymethyl)phenyl)butyl)tetrazole
5-(4-(4-(3-(2-quinolinylmethyloxy)phenoxymethyl)phenyl)-3-methylbutyl) tetrazole
5-(4-(3-(2-quinolinylmethyloxy)phenylthiomethyl)phenyl)tetrazole
5-(4-(3-(2-quinolinylmethylthio)phenylthiomethyl)phenyl)tetrazole
5-(4-(3-(2-quinolinylmethyloxy)phenoxymethyl)-3-methylphenyl)tetrazole
5-(4-(3-(2-quinolinylmethyloxy)phenoxymethyl)-2-methylphenyl)tetrazole
5-(4-(3-(2-quinolinylmethyloxy)phenoxymethyl)-2-methoxyphenyl) tetrazole
5-(4-(3-(2-quinolinylmethyloxy)phenoxymethyl)-3-methoxyphenyl) tetrazole
5-(2-(4-(2-quinolinylmethyloxy)phenoxymethyl)-3-methylphenyl)tetrazole
5-(3-(4-(2-quinolinylmethyloxy)phenoxymethyl)-4-methoxyphenyl) tetrazole
5-(3-(3-(2-quinolinylmethyloxy)phenoxymethyl)-4-methoxyphenyl) tetrazole TABLE XI-continued 5-(4-(3-(2-quinolinylmethyloxy)-5-methylphenoxymethyl)-2-methoxyphenyl)tetrazole
5-(4-(3-(2-quinolynylmethyloxy)-N-acetylphenylaminomethyl)phenyl)tetrazole
5-(4-(3-(2-quinolynylmethylthio)-N-acetylphenylaminomethyl)phenyl)tetrazole

EXAMPLE 32

5-(3-(4-(2-QUINOLINYLMETHYLOXY)
PHENOXYMETHYL)PHENOXYMETHYL)
TETRAZOLE

A. α-(3-hydroxymethylphenoxy)acetonitrile

A mixture of 3-hydroxymethyl phenol (0.081 mol), bromoacetonitrile (0.081 mol) and anhydrous potassium carbonate (0.081 mol) in acetone (160 ml) and dimethylformamide (20 ml) are heated at reflux for 48 hrs. The reaction mixture is filtered and evaporated. The residue is diluted with ethyl acetate (150 ml), washed with 10% aqueous sodium hydroxide solution (3×100 ml) and then with brine (3×100 ml). The ethyl acetate solution is dried (magnesium sulfate) and chromatographed using a silica gel column (ca. 100 g) and eluted with 1:1 petroleum ether:ethylacetate (2 l). The resultant oil is used directly in the next step.

B. α-(3-chloromethylphenoxy)acetonitrile

α-(3-Hydroxymethylphenoxy)acetonitrile (0.055 mol) in diethylether (150 ml) is stirred with thionyl chloride (0.060 mol) and a few drops of dimethylformamide at 40° C. for 1 hr. the solution is washed with water and brine, then evaporated to give α-(3-chloromethylphenoxy)acetonitrile as a yellow oil which is used directly in the next step.

C. α-(3-(4-(2-quinolinylmethyloxy)phenoxymethyl)phenoxy)acetonitrile

A mixture of α-(3-chloromethylphenoxy)acetonitrile (0.025 mol) sodium 4-(2-quinolinylmethyloxy)phenoxide (0.025 mol) and anhydrous potassium carbonate (0.125 mol) in dimethylsulfoxide (50 ml) is stirred at ambient temperature for 18 hrs. The reaction is diluted with water (600 ml) and extracted with ethyl acetate (3×150 ml). The ethyl acetate solution is washed with water (3×100 ml) and brine (100 ml) then dried and evaporated to give α-(3-(4-(2-quinolinylmethyloxy)phenoxymethyl)phenoxy)acetonitrile. (M.P. 110–114° C.)

D. 5-(3-(4-(2-quinolinylmethyloxy)phenoxymethyl)phenoxymethyl)tetrazole

α-(3-(4-(2-quinolinylmethyloxy)phenoxymethyl)phenoxy)acetonitrile (8.12 mmol), sodium azide (24.4 mmol) and ammonium chloride (24.4 mmol) in dimethylformamide (10 ml) are heated at 115–120° C. for 6 hrs. After cooling, the reaction mixture is diluted with ethyl acetate (150 ml), washed with water (6×100 ml) then dried and evaporated. The residue is chromatographed on a column of silica gel (360 g) and eluted with a gradient of isopropanol in methylene chloride to give 5-(3-(4-(2-quinolinylmethyloxy)phenoxymethyl)phenoxymethyl)tetrazole. (M.P. 131–32° C.)

EXAMPLE 33

When sodium 4-(2-quinolinylmethyloxy)phenoxide of Example 32, Step C, is replaced with sodium 3-(2-quinolinylmethyloxy)phenoxide, the product prepared is 5-(3-(3-(2-quinolinylmethyloxy)phenoxymethyl)phenoxymethyl)tetrazole. (M.P. 135–137° C.)

EXAMPLE 34

When α-(3-hydroxymethylphenoxy)acetonitrile of Example 32, Step B. is replaced with α-(4-hydroxymethylphenoxy)acetonitrile then the product prepared is 5-(4-(3-(2quinolinylmethyloxy)phenoxymethyl)phenoxymethyl)tetrazole. (M.P. 154–156° C.)

EXAMPLE 35

When α-(3-hydroxymethylphenoxy)acetonitrile of Example 32, Step B. is replaced with α-(2-hydroxymethylphenoxy)acetonitrile or α-((2-hydroxymethyl-5-carbomethoxy)phenoxy)acetonitrile then the products prepared are 5-(2-(3-(2quinolinylmethyloxy)phenoxymethyl)phenoxymethyl)tetrazole (M.P. 118–120° C.) or 5-(2-(3-(2-quinolinylmethyloxy)-phenoxymethyl)-5-carbomethoxy-phenoxymethyl)tetrazole. (M.P. 159–162° C.)

EXAMPLE 36

When bromoacetonitrile of Example 32, Step A is replaced by the nitriles of Table XII below then the corresponding product is prepared:

TABLE XII bromoacetonitrile
α-bromo-α-methylacetonitrile
α-bromo-β-ethylacetonitrile
α-bromopropionitrile
β-bromopropionitrile
β-bromo-β-methylpropionitrile-bromobutyronitrile
β-bromobutyronitrile
α-bromobutyronitrile

EXAMPLE 37

When 3-hydroxymethylphenol of Example 32, Step A is replaced by the compounds of Table XIIIa below, then the corresponding products are prepared.

TABLE XIIIa 2-hydroxymethylphenol
3-hydroxymethylphenol
4-hydroxymethylphenol
3-mercaptobenzylalcohol
4-mercaptobenzylalcohol
3-hydroxymethyl-N-acetylamidine
4-hydroxymethyl-N-acetylamidine
4-hydroxymethylamidine
4-methyl-2-hydroxymethylphenol
2-methyl-5-hydroxymethylphenol
4-methyl-3-hydroxymethylphenol
5-methyl-3-hydroxymethylphenol
3-methyl-4-hydroxymethylphenol
2-methyl-4-hydroxymethylphenol
3-methyl-5-hydroxymethylphenol
4-methoxy-3-hydroxymethylphenol
3-methoxy-4-hydroxymethylphenol
2-methoxy-4-hydroxymethylphenol
5-methoxy-3-hydroxymethylphenol
3-methoxy-5-hydroxymethylphenol
2-methoxy-5-hydroxymethylphenol
2-(1'-hydroxyethyl)phenol
3-(1'-hydroxyethyl)phenol
4-(1'-hydroxyethyl)phenol
2-(2'-hydroxyethyl)phenol
3-(2'-hydroxyethyl)phenol
4-(2'-hydroxyethyl)phenol
2-(3'-hydroxypropyl)phenol
3-(3'-hydroxypropyl)phenol

TABLE XIIIa-continued 4-(3'-hydroxypropyl)phenol
2-(2'-hydroxypropyl)phenol
3-(2'-hydroxypropyl)phenol
4-(2'-hydroxypropyl)phenol
2-(1'-hydroxypropyl)phenol
3-(1'-hydroxypropyl)phenol
4-(1'-hydroxypropyl)phenol
3-(4'-hydroxybutyl)phenyl
4-(4'-hydroxybutyl)phenyl

EXAMPLE 38

Following the procedures of Examples 32 to 34, when sodium 4-(2-quinolinylmethyloxy)phenoxide of Example 32, Step C, is replaced by the metal hydroxy, thio or amino salts of the compounds of Table VIII, Example 24, then the corresponding product is prepared. Representative examples of compounds prepared by this invention are shown in Table XIIIb.

TABLE XIIIb 5-(4-(4-(2-quinolinylmethyloxy)phenoxymethyl)phenoxymethyl)tetrazole
5-(4-(2-(2-quinolinylmethyloxy)phenoxymethyl)phenoxymethyl)tetrazole
5-(3-(2-(2-quinolinylmethyloxy)phenoxymethyl)phenoxymethyl)tetrazole
5-(2-(4-(2-quinolinylmethyloxy)phenoxymethyl)phenoxymethyl)tetrazole
5-(2-(3-(2-quinolinylmethyloxy)phenoxymethyl)phenoxymethyl)tetrazole
5-(2-(2-(2-quinolinylme.thyloxy)phenoxymethyl)phenoxymethyl)tetrazole
5-(3-(4-(2-quinolinylmethyloxy)phenoxymethyl)-2-methoxyphenoxymethyl)tetrazole
5-(3-(4-(2-quinolinylmethyloxy)phenoxymethyl)-3-methoxyphenoxymethyl)tetrazole
5-(4-(3-(2-quinolinylmethyloxy)phenoxymethyl)-2-methoxyphenoxymethyl)tetrazole
5-(4-(3-(2-quinolinylmethyloxy)phenoxymethyl)-3-methoxyphenoxymethyl)tetrazole
5-(4-(3-(2-quinolinylmethyloxy)phenoxymethyl)-3-methylphenoxymethyl)tetrazole
5-(4-(4-(2-quinolinylmethyloxy)phenoxymethyl)-2-methoxyphenoxymethyl)tetrazole
5-(4-(4-(2-quinolinylmethyloxy)phenoxymethyl)-3-methoxyphenoxymethyl)tetrazole
5-(4-(4-(2-quinolinylmethyloxy)phenoxymethyl)-3-methylphenoxymethyl)tetrazole
5-(4-(4-(2-quinolinylmethyloxy)phenoxymethyl)-2-methylphenoxymethyl)tetrazole
5-(4-(4-(2-quinolinylmethyloxy)-2-methylphenoxymethyl) phenoxymethyl)tetrazole
5-(4-(4-(2-quinolinylmethyloxy)-3-methylphenoxymethyl)phenoxymethyl)tetrazole
5-(4-(4-(2-quinolinylmethyloxy)-3-methoxyphenoxymethyl)phenoxymethyl)tetrazole
5-(3-(3-(2-quinolinylmethyloxy)-4-methoxyphenoxymethyl)phenoxymethyl)tetrazole
5-(3-(3-(2-quinolinylmethyloxy)-4-methylphenoxymethyl)phenoxymethyl)tetrazole
5-(4-(4-(2-quinolinylmethyloxy)-2-methylphenoxymethyl)-3-methylphenoxymethyl)tetrazole
5-(4-(4-(2-quinolinylmethyloxy)-3-methylphenoxymethyl)-2-methylphenoxymethyl)tetrazole
5-(2-(3-(4-(2-quinolinylmethyloxy)phenoxymethyl)phenoxy)ethyl)tetrazole
5-(3-(3-(4-(2-quinolinylmethyloxy)phenoxymethyl)phenoxy)propyl)tetrazole
5-(2-(3-(4-(2-quinolinylmethyloxy)phenoxymethyl)phenoxy)propyl)tetrazole
5-(3-(3-(4-(2-quinolinylmethyloxy)phenoxymethyl)phenoxy)butyl)tetrazole
5-(4-(4-(2-quinolinylmethyloxy)phenylthiomethyl)phenoxymethyl)tetrazole
5-(4-(4-(2-quinolinylmethyloxy)phenylthiomethyl)phenylmethyl)tetrazole
5-(4-(4-(2-quinolinylmethylthio)phenoxymethyl)phenoxymethyl)tetrazole
5-(4-(4-(2-quinolinylmethyloxy)phenoxymethyl)phenyl-N-acetylaminomethyl)tetrazole
5-(3-(4-(4-(2-quinolinylmethyloxy)phenoxymethyl)phenylthio)butyl)tetrazole

TABLE XIIIb-continued 5-(3-(3-(4-(2-quinolinylmethyloxy)phenoxy-1'-ethyl)phenoxymethyl) tetrazole
5-(3-(3-(4-(2-quinolinylmethyloxy)phenoxy-2'-propyl)phenoxymethyl) tetrazole
5-(3-(3-(4-(2-quinolinylmethyloxy)phenoxy-3'-butyl)phenoxymethyl) tetrazole

EXAMPLE 39

3-(3-(2-QUINOLINYLMETHYLOXY) BENZYLOXY)BENZALDEHYDE

When 3-hydroxybenzonitrile in Example 7 is replaced by 3-hydroxybenzaldehyde then the product prepared is 3-[3-(2-quinolinylmethyloxy)benzyloxy)benzaldehyde.

EXAMPLE 40

When 3-hydroxybenzaldehyde of Example 39 is replaced by the compounds of Table XIV below, then the corresponding product is obtained.

TABLE XIV 2-hydroxybenzaldehyde
3-hydroxybenzaldehyde
4-hydroxybenzaldehyde
2-methyl-3-hydroxybenzaldehyde
5-methyl-3-hydroxybenzaldehyde
2-methyl-4-hydroxybenzaldehyde
3-methyl-4-hydroxybenzaldehyde
5-methoxy-3-hydroxybenzaldehyde
4-methoxy-3-hydroxybenzaldehyde
2-methoxy-3-hydroxybenzaldehyde
5-carbomethoxy-3-hydroxybenzaldehyde
3-hydroxyphenylacetaldehyde
4-hydroxyphenylacetaldehyde
3-hydroxyphenylpropionaldehyde
4-hydroxyphenylpropionaldehyde
3-hydroxyphenylisopropionaldehyde
4-hydroxyphenylisopropionaldehyde
3-hydroxyphenoxyacetaldehyde
4-hydroxyphenylthiopropionaldehyde

EXAMPLE 41

When 3-(2-quinolinylmethyloxy)benzyl chloride of Example 39 is replaced by the compounds prepared by Examples 2–6 and 3-hydroxybenzaldehyde of Example 39 is replaced by the compounds of Table XIV, Example 40, then the corresponding products are obtained.

EXAMPLE 42

3-(3-(2-QUINOLINYLMETHYLOXY) BENZYLOXY)CINNAMYLNITRILE

Sodium hydride (60% oil dispersion, 1.2 g) and diethyl cyanomethylphosphonate (5 ml) are combined and stirred in THF (50 ml) for 5 minutes. This is then added to a THF solution of 3-(3-(2-quinolinylmethyloxy)benzyloxy) benzaldehyde (9.59 g). The reaction mixture is stirred for an additional 30 minutes and poured into ice water. The crude product is filtered and chromatographed through a silica gel dry column using chloroform as the eluant to give 3-(3-(2-quinolinylmethyloxy)benzyloxy)cinnamylnitrile.

EXAMPLE 43

When 3-(3-(2-quinolinylmethyloxy)benzyloxy) benzaldehyde of Example 42 is replaced by the compounds of Example 41,the corresponding product is prepared.

When diethylcyanomethylphosphonate in the above Example is replaced by diethylcyanoethylphosphate, diethylcyanopropylphospate or diethylcyanoisopropylphosphate then the corresponding products are obtained.

EXAMPLE 44

5-(3-(3-(2-QUINOLINYLMETHYLOXY) BENZYLOXY)STYRYLTETRAZOLE HYDROCHLORIDE

A mixture of 3-(3-(2-quinolinylmethyloxy)benzyloxy) cinnamylnitrile (0.03 mol), anhydrous aluminum chloride (0.03 mol) and sodium azide (0.09 mol) in THF (30 ml) is stirred and refluxed for 18 hours. Hydrochloric acid (18% HCl 15 ml) is added and thereafter the reaction mixture is poured into ice water. The precipitate is collected and then recrystalized from methanol-ethyl acetate to obtain pure 5-(3-(3-(2quinolinylmethyloxy)benzyloxy)styryl)tetrazole hydrochloride.

The free base is obtained by treatment of the salt with one equivalent of sodium hydroxide solution followed by removal of sodium chloride and water.

EXAMPLE 45

When 3-(3-(2-quinolinylmethyloxy)benzyloxy) cinnamylnitrile of Example 44 is replaced by the compounds formed in Example 43, then the corresponding product is prepared. Representative compounds prepared by this invention are described in Table XV.

TABLE XV 5-(4-(3-(2-quinolinylmethyloxy)phenoxy)styryl)tetrazole
5-(4-(3-(2-quinolinylmethyloxy)benzyloxy)styryl)tetrazole
5-(3-(4-(2-quinolinylmethyloxy)benzyloxy)styryl)tetrazole
5-(4-(4-(2-quinolinylmethyloxy)benzyloxy)styryl)tetrazole
5-(4-(3-(2-quinolinylmethyloxy)-4-methylbenzyloxy)styryl)tetrazole
5-(4-(3-(2-quinolinylmethyloxy)benzyloxy)3-methylstyryl)tetrazole
5-(3-(3-(2-quinolinylmethylthio)benzyloxy)styryl) tetrazole
5-(3-(4-(2-quinolinylmethylthio)phenoxy)styryl)tetrazole
5-(3-(4-(2-quinolinylmethyloxy)benzylthio)styryl)tetrazole
5-(3-(4-(3-(2-quinolinylmethyloxy)benzyloxy)phenoxy)-2-propen-1-yl) tetrazole

EXAMPLE 46

3-METHYLCARBOETHOXY-5-(4-(3-(2-QUINOLINYLMETHYLOXY) PHENOXYMETHYL)PHENYL)TETRAZOLE

To a solution of 0.2 g sodium in 30 ml ethanol is first added 1 g of 5-(4-(3-(2-quinolinylmethyloxy) phenoxymethyl)phenyl)tetrazole and then after 30 minutes 0.6 g of ethylbromoacetate and stirring is continued at 80° C. for 16 hours. The solvent is then removed, diluted with water, filtered, washed with ether and dried to give the desired compound, also referred to as ethyl 5-(4-(3-(2-quinolinylmethyloxy)phenoxymethyl)phenyl)tetrazol-3-yl acetate.

When ethylbromoacetate in the above procedure is replaced with N,N-diethyl-α-bromoacetamide, N,N-diethylaminoethyl bromide or N-acetylaminoethyl bromide or N-acetyl-α-bromoacetamide, then the corresponding products are obtained.

EXAMPLE 47

5-(4-(3-(2-QUINOLINYLMETHYLOXY) PHENOXYMETHYL)PHENYL)TETRAZOL-3-YL)ACETIC ACID

A mixture of 1 g of ethyl [5-(4-(3-(2-quinolinylmethyloxy)phenoxymethyl)phenyl)tetrazol-3-yl]acetate in 5 ml ethanol and 40 ml of 1N NaOH is stirred at 70° C. for 4 hours. This is cooled, diluted with water, acidified with acetic acid, filtered, washed with water, and then ethyl acetate to give 5-(4-(3-(2-quinolinylmethyloxy) phenoxymethyl)phenyl)tetrazol-3-yl acetic acid.

In a similar manner, the substituted tetrazoles of this invention may be prepared.

EXAMPLE 48

4-(4-(2-QUINOLINYLMETHYLSULFONYL) PHENOXYMETHYL)BENZOIC ACID

A. 4-(4-(2-quinolinylmethylthio)phenoxymethyl)benzoic acid (4 mmol) in dichloroethene (50 ml) is stirred with m-chloroperbenzoic acid (4 mmol) and solid potassium hydrogen carbonate (1.0 g). The reaction is assayed by TLC and upon consumption of the starting thio compound, the mixture is filtered, washed with dilute aqueous sodium bisulfite, dried and evaporated to give 4-(4-(2-quinolinylmethylsulfinyl)-phenoxymethyl)benzoic acid.

B. To 3 mmol of the sulfinyl compound from Step A in acetic acid (40 mmol) is added 30% hydrogen peroxide (2 ml). The mixture is stirred at ambient temperature and assayed by TLC. Upon disappearance of the sulfinyl starting compound, the reaction mixture is diluted with dichloromethane, washed with dilute aqueous sodium bisulfite and water, dried and evaporated to give 4-(4-(2-quinolinylmethylsulfonyl)phenoxymethyl)benzoic acid.

In a similar manner, the sulfinyl and sulfonyl compounds of this invention may be prepared.

EXAMPLE 49

5-(3-METHYL-4-(4-(4-(2-QUINOLINYLMETHYLOXY)BENZYLOXY)-PHENYL)BUTYL)TETRAZOLE

A. 4-benzyloxy-α-methyl-cinnamic acid ethyl ester

To a solution of sodium hydride (60% oil dispersion, 3.1 g) and diethyl 2-phosphonopropionate (15.5 g) in tetrahydrofuran (50 ml) is added dropwise a tetrahydrofuran solution of 4-benzyloxy-benzaldehyde (10.6 g). After stirring at room temperature for 2 hours, the reaction mixture is poured into ice water. The insoluble solid is collected, and used directly in the next step.

B. 4-benzyloxy-α-methyl-cinnamic alcohol

Under argon and with stirring, a tetrahydrofuran solution of 4-benzyloxy-α-methyl-cinnamic acid ethyl ester (11.9 g) is added dropwise to a cooled tetrahydrofuran solution of lithium aluminum hydride (2.5 g). The reaction mixture is allowed to stir for 18 hours and afterward, the excess reagent is destroyed in a conventional manner. The residue which results from the evaporation of the solvent is partitioned in a water/ethyl acetate mixture and from the organic layer, the desired product is obtained. This is used directly in the next step.

C. 4-benzyloxy-α-methyl-cinnamyl aldehyde

Manganese dioxide (15 g total) is added portionwise to a dichloromethane solution (100 ml) of 4-benzyloxymethylcinnamic alcohol with stirring over a period of one week. After two filtrations, the filtrate is evaporated to yield a gum. Upon treatment with cold hexane, the crude product results which is used directly in the next step.

D. 5-(p-benzyloxyphenyl)-4-methyl-2,4-pentadienenitrile

To a solution of sodium hydride (60% oil dispersion, 1.5 g) and diethyl cyanomethylphosphonate (5.4 g) in tetrahydrofuran (50 ml) is added dropwise a tetrahydrofuran solution of 4-benzyloxy-α-methyl-cinnamyl aldehyde (4.8 g). After stirring at room temperature for 2 hours, the reaction mixture is poured into ice water. The insoluble material is collected and used directly in the next step.

E. 5-(p-hydroxyphenyl-4-methylvaleronitrile 5-(p-Benzyloxyphenyl)-4-methyl-2,4-pentadienenitrile (4.3 g) dissolved in ethanol is hydrogenated (0.8 g of 5% palladium over charcoal as catalyst) around 30 psi overnight. After filtering off the catalyst, the solvent is evaporated to give an oil which is used directly in the next step.

F. 4-methyl-5-(4-(4-(2-quinolinyloxymethyl)benzyloxy) phenyl)valeronitrile

A reaction mixture of 5-hydroxyphenyl-4-methyl-valeronitrile (2.9 g), 4-(2-quinolinylmethyloxy)benzyl chloride hydrochloride (6.3 g) and anhydrous potassium carbonate (30 g) in dimethylformamide (60 ml) is stirred and heated (110° C.) for 5 hours. Afterward, the solvent is removed under vacuum and the residue is partitioned in a mixture of chloroform/water. The organic layer is evaporated and the resultant oil is purified on a silica gel dry column (chloroform as eluant) to give product which may used directly in the next step.

G. 5-(3-methyl-4-(4-(4-(2-quinolinylmethyloxy)-benzyloxy)phenyl)butyl)tetrazole

A mixture of 4-methyl-5(4-(4-(2-quinolinylmethyloxy)benzyloxy)phenyl)valeronitrile (1.5 g.), sodium azide (3 g), ammonium chloride (1.9 g) in dimethylformamide (20 ml) is stirred and heated at 135° C. for 18 hours. After cooling, the reaction mixture is poured into ice water and the insoluble material is taken up by chloroform. The residue from the evaporation of chloroform is purified by silica gel dry column (5% methanol chloroform as eluant) to yield 5-(3-methyl-4-(4-(4-(2-quinolinylmethyloxy)benzyloxy)-phenyl)butyl)tetrazole.

EXAMPLE 50

When 2-chloromethylquinoline of Example 49, Part F is replaced by the quinoline compounds of Examples 5 and 6, then the corresponding product is obtained. When the products are treated according to the procedures of Steps F and G, then the corresponding tetrazole products are obtained.

EXAMPLE 51

When diethyl 2-phosponopropionate of Example 49, Step A is replaced by the Wittig reagents of Table XVI below then the corresponding products are obtained.

TABLE XVI diethyl 2-phosphonoacetate
diethyl 2-phosphonopropionate
diethyl 3-phosphonopropionate
diethyl 4-phosphonobutyrate
diethyl 3-phosphonobutyrate
diethyl 2-phosphonobutyrate
diethyl 5-phosphonopentanoate
diethyl 4-phosphonopentanoate
diethyl 3-phosphonopentanoate
diethyl 4-phosbono-3-methylbutyrate
diethyl 4-phosphono-2,3-dimethylbutyrate
diethyl 5-phosphono-4-methylpentanoate
diethyl 5-phosphono-3,4-dimethylpentanoate
diethyl 4-phosphono-3,3-dimethylbutyrate
diethyl 4-phosphono-3-phenylbutyrate
diethyl 4-phosphono-3-benzylbutyrate
diethyl 3-phosphono-2,2-dimethylpropionate TABLE XVI-continued diethyl 4-phosphono-2-propylbutyrate
diethyl 4-phosphono-3-propylbutyrate
diethyl 3-phosphonomethylhexanoate
diethyl 4-phosphonoheptanoate

EXAMPLE 52

When diethylcyanomethylphosphonate of Example 49, Step D is replaced by the Wittig reagents of Table XVII below then the corresponding products are obtained.

TABLE XVII diethyl 2-phosphonoacetonitrile
diethyl 3-phosphonopropionitrile
diethyl 2-phosphonopropionitrile
diethyl 4-phosphonobutyronitrile
diethyl 3-phosphonobutyronitrile
diethyl 2-phosphonobutyronitrile
diethyl 5-phosphonopentanonitrile
diethyl 4-phosphonopentanonitrile
diethyl 3-phosphonopentanonitrile
diethyl 2-phosphonopentanonitrile
diethyl 4-phosphono-5-phenylpentanonitrile
diethyl 4-phosphono-3-phenylbutyronitrile
diethyl 4-phosphono-5-cyclopropylpentanonitrile
diethyl 4-phosphonohexanonitrile
diethyl 4-phosphonoheptanonitrile
diethyl 4-phosphono-5-carbethokypentanonitrile
diethyl 4-phosphono-3-methylenebutyronitrile
diethyl 4-phosphono-3-ethylidenebutyronitrile
diethyl 1-phosphonomethyl-1-cyanoethylcyclopropane
diethyl 1-phosphonomethyl-1-cyanomethylcyclobutane
diethyl 1-phosphonomethyl-2-cyanomethylcyclobutane
diethyl 1-phosphonomethyl-2-cyanomethylcyclopentane

EXAMPLE 53

When diethyl 2-phosphonopropionate of Example 49, Step A is replaced by the Wittig reagents of Table XVII, Example 52, then the corresponding products are obtained. When these products are treated according to the procedure of Example 50, then the corresponding product is obtained.

EXAMPLE 54

When 4-hydroxy-3-methoxybenzoate of Example 14 is replaced with 3-hydroxymethylphenol, then the product prepared is 3(3-(2-quinolinylmethyloxy)benzyloxy)benzyl alcohol.

EXAMPLE 55

When 4-hydroxy-3-methoxybenzoate of Example 14 is replaced with the compounds of Table XVIII below and 3-(2-quinolinylmethyloxy)benzyl chloride is replaced by the compounds of Example 6, then the corresponding products are prepared.

TABLE XVIII 1,2-dihydroxybenzene
1,3-dihydroxybenzene
1,4-dihydroxybenzene
2-mercaptophenol
3-mercaptophenol
4-mtercaptophenol
1,3-dimercaptobenzene
3-hydroxymethylphenol

TABLE XVIII-continued 3-hydroxyethylphenol
3-mercaptomethylphenol
4-hydroxymethylphenol
4-hydroxyethylphenol
2-methylresorsinol
5-methylresorsinol
5-methyl-1,4-dihydroxybenzene

EXAMPLE 56

5-(3-CHLOROPROPYL)TETRAZOLE

A mixture of 3.5 g of 4-chlorobutyronitrile, 2.3 g of sodium azide and 1.9 g of ammonium chloride in 50 ml of dimethyl-formamide is stirred at 140° C. for 20 hours. The reaction mixture is poured onto ice, basified with 1N sodium hydroxide and extracted twice with ethyl acetate. The aqueous fraction is acidified with acetic acid and extracted with ethylacetate. Evaporation of the ethyl acetate gives 5-(3-chloropropyl)-tetrazole which is used directly in the next step.

EXAMPLE 57

When 4-chlorobutyronitrile of Example 56 above is replaced by the nitrides of Table XIX below then the corresponding tetrazole product is obtained.

TABLE XIX chloroacetonitrile
bromoacetonitrile
3-chloropropionitrile
4-chlorobutyronitrile
5-chloropentanonitrile
6-chlorohexanonitrile
2-chloropropionitrile
2-methyl-3-chloropropionitrile
2-chlorobutyronitrile
3-chlorobutyronitrile
4-methyl-5-chloropentanonitrile
2-methyl-3-chloropropionitrile
3-benzyl-4-chlorobutyronitrile
3-carbethoxymethyl-4-chlorobutyronitrile
3-methoxymethyl-4-chlorobutyronitrile
2,3-dimethyl-4-chloropentanonitrile
3,3-dimethyl-4-chloropentanonitrile
spiro-(3,3-cyclopropane)-4-chlorobutyronitrile
1-chloromethyl-2-cyanomethylcyclobutane
1-chloromethyl-2-cyanomethylcyclohexane
3-cyclopropylmethyl-4-chlorobutyronitrile
3-dimethylaminomethyl-4-chlorobutyronitrile
3-methylene-4-chlorobutyronitrile
3-propylidene-4-chlorobutyronitrile

EXAMPLE 58

5-(4-(3-(3-(2-QUINOLINYLMETHYLOXY)BENZYLOXY)PHENYL)BUTYL)-TETRAZOLE

A mixture of (0.014 mol) 3-(3-(2-quinolinylmethyloxy)benzyloxy)benzyl alcohol (0.14 mol) 5-(3-chloropropyl)tetrazole and 2 g (0.036 mol) KOH in 5 ml water and 50 ml ethanol is heated over a steam bath for a period of 3 hours. Reaction mixture is concentrated to dryness and slurried into water and extracted with methylene chloride. The methylene chloride extract is washed with water, dried over $MgSO_4$ and concentrated under reduced pressure to obtain solid which is passed through a silica gel column using hexane/ethyl acetate as eluent. Evaporation of eluent gives 5-(4-(3-(3-(2-quinolinylmethyloxy)benzyloxy)phenyl)butyl)tetrazole.

EXAMPLE 59

When 3-(3-(2-quinolinylmethyloxy)benzyloxy)benzyl alcohol of Example 58 is replaced by the compounds prepared by Examples 54 and 55 and 5-(3-chloropropyl) tetrazole is replaced by the compounds prepared by Example 57, then the corresponding product is obtained.

TABLE XX 5-(4-(4-(3-(2-quinolinylmethyloxy)benzyloxy)phenyl)butyl)tetrazole
5-(3-(4-(3-(2-quinolinylmethyloxy)benzyloxy)phenyl)butyl)tetrazole
5-(3-(4-(4-(2-quinolinylmethyloxy)benzyloxy)phenyl)butyl)tetrazole
5-(2-(3-(3-(2-quinolinylmethyloxy)benzyloxy)phenyl)propyl)tetrazole
5-(3-(3-(3-(2-quinolinylmethylthio)benzyloxy)phenyl)butyl)tetrazole
5-(3-(3-(3-(2-quinolinylmethyloxy)benzyloxy)phenyl)butyl)tetrazole
5-(3-(3-(3-(2-quinolinylmethyloxy)benzylthio)phenyl)butyl)tetrazole
5-(4-(3-(2-quinolinylmethyloxy)benzyloxy)phenyl)butyl)tetrazole
5-(3-(3-(3-(2-quinolinylmethyloxy)phenoxy)phenyl)butyl)tetrazole

EXAMPLE 60

When 3-hydroxybenzonitrile in Example 7 is replaced by 3-hydroxybenzaldehyde then the product prepared is 3-(2quinolinylmethyloxy)benzaldehyde.

EXAMPLE 61

When 3-hydroxybenzaldehyde in Example 60 is replaced by the compounds of Table XIV, Example 40 and 3-(2-quinolinylmethyloxy)benzyl chloride is replaced by the chlorides prepared in Examples 5 and 6, then the corresponding product is prepared.

EXAMPLE 62

5-(4-(3-(2-QUINOLINYLMETHYLOXY)BENZOYLMETHYL)PHENYL)TETRAZOLE

A. 2-(3-(2-quinolinylmethyloxy(phenyl)-1,3-dithiane

A 1M solution of 3-(2-quinolinylmethyloxy) benzaldehyde (0.01 mol) in chloroform is combined with an equimolar amount of 1,3 propane-dithiol at −20° C. Dry HCl gas is slowly passed through the solution for 5–10 minutes. The reaction mixture is then allowed to come to room temperature. After 3 hours, the reaction mixture is worked up by successively washing with water, 10% aqueous KOH and water and drying over K2CO3. Evaporation of the solvent furnishes the desired product which is purified by column chromatography to give product which is used directly in the next step.

B. 2-(3-(2-quinolinylmethyloxy)phenyl-2-(p-cyanobenzyl)-1,3-dithiane

To a 0.2M THF solution of the 2-(3-(2quinolinyl-methyloxy)phenyl)-1,3-dithiane (0.01 mol) under is added a 5% excess of N-butyl lithium in N-hexane (2.5M) at a rate if 3–5 ml/min at −78° C. After 3 hours, 4-cyanobenzylchloride (0.01 mol in 20 ml of THF) is added dropwise over a period of 10 minutes. Let stir 3 hours at −78° C. and then allow the reaction mixture to come to 0° C. slowly. The mixture is poured into 3 volumes of water, extracted with chloroform furnishing an organic solution which is washed twice with water, 7% aqueous KOH and again with water. The organic layer is dried over K2CO3 and is concentrated. The crude product is purified by column chromatography to give the desired product which is used directly in the next step.

C. 4-(3-(2-quinolinylmethyloxy)benzoylmethyl)
benzonitrile

To a solution of 2-(3-(2-quinolinylmethyloxy)-1,3-dithiane (1.0 mmol) in 80% aqueous acetonitrile (10 ml) is added mercuric chloride (2.2 mmol) as a solution in the same solvent mixture. Mercuric oxide (1.1 mmol) is then added to buffer the reaction mixture near pH=7. The dithiane-mercuric chloride complex separates as a white precipitate. The reaction mixture is refluxed under nitrogen for 5 hours, then cooled and filtered through Super Gel. The filter cake is washed thoroughly with 1:1 hexane-dichloromethane. The organic phase is washed with 5 M aqueous ammonium acetate, water and brine. The organic phase is then dried with MgSO$_4$, and is concentrated to give the crude product which is purified by column chromatography to give 4-(3-(2-quinolinylmethyloxy)benzoylmethyl)benzonitrile.

D. 5-(4-(3-(2-quinolinylmethyloxy)benzoylmethyl)-phenyl)tetrazole

A heterogenous mixture of 4-(3-(2-quinolinylmethyloxy)benzoylmethyl)benzonitrile (1.35 mmol). NaN$_3$ (6.77 mmol), pyridinium hydrochloride (6.77 mmol) in DMF (3 ml) is heated at 100° C. for 3 hours under nitrogen. The reaction mixture is poured into water and the product is collected on a filter. Recrystallization from EtOAc-DMF gives 5-(4-(3-(2-quinolinylmethyloxy)benzoylmethyl)phenyl)tetrazole.

EXAMPLE 63

When 3-(2-quinolinylmethyloxy)benzaldehyde in Example 62, Step A is replaced by the aldehydes of Example 61, and 4-cyanobenzyl chloride of Example 62, Step B is replaced by the compounds of Table X, Example 29 or Table VII, Example 23, then the corresponding products are obtained. Representative compounds prepared by this invention are shown in Table XXI.

TABLE XXI 5-(4-(4-(2-quinolinylmethyloxy)benzoylmethyl)phenyl)tetrazole
5-(4-(3-(2-quinolinylmethyloxy)benzoylmethyl)benzyl)tetrazole
5-(3-(4-(3-(2-quinolinylmethyloxy)benzomethyl)phenyl)propyl)tetrazole
5-(3-(3-(2-quinolinylmethylthio)benzoylmethyl)phenyl)tetrazole
5-(4-(3-(2-quinolinylmethyloxy)benzoylethyl)benzyl)tetrazole

EXAMPLE 64

5-(3-(3-(2-QUINOLINYLMETHYLOXY)
BENZOYLAMINO)PHENYL)TETRAZOLE

A. 3-(2-quinolinylmethyloxy)benzoic acid

A mixture of 28.16 g (0.132 mol) of 2-quinolinylmethyl chloride HCl, 18 g (0.132 mol) of 3-hydroxybenzoic acid and 39.6 g of potassium carbonate in 110 ml of DMF is heated at 70° C. overnight. The reaction mixture is poured into water, and the precipitated product is collected, filtered and dried to give 3-(2quinolinylmethyloxy)benzoic acid.

B. 3-(2-quinolinylmethyloxy)benzoic acid chloride

A mixture of 15.6 g (0.1 mol) of 3-(2-quinolinylmethyloxy)benzoic acid and 11.9 g (0.1 mol) of thionyl chloride is refluxed for 4 hours. The reaction mixture is then evaporated to dryness at room temperature and used directly in the next step.

C. 3-(3-(2-quinolinylmethyloxy)benzoylamino)benzonitrile

A solution of 3-aminobenzonitrile (10 mmol) in 50 ml of chloroform and triethylamine (11 mmol) is added to a solution of 10 mmol of 3-(2-quinolinylmethyloxy)benzoic acid chloride in 20 ml of chloroform over a period of 10 minutes. The reaction is stirred at room temperature for 2 hours and is poured into water and then extracted into chloroform. The organic solution is dried and evaporated to give 3-(3-(2-quinolinylmethyloxy)benzoylamino)benzonitrile.

D. 5-(3-(3-(2-quinolinylmethyloxy)benzoylamino)phenyl)tetrazole

A mixture of 10 mmol of 3-(3-(2-quinolinylmethyloxy)benzoylamino)benzonitrile, 50 mmol of sodium azide, and 50 mmol of pyridine HCl in 30 ml of DMF is heated at 100° C. for 2 days. The reaction mixture is poured into water, and the product is collected on a filter. Recrystallization from ethyl acetate and DMF gives 5-(3-(3-(2-quinolinylmethyloxy)benzoylamino)phenyl)tetrazole.

In a similar manner, the compounds of this invention where B is

may be made.

EXAMPLE 65

5-(3-(3-(2-QUINOLINYLMETHYLOXY)-ANILINOCARBONYL)PHENYL)TETRAZOLE

When the procedure of Example 64 is followed and 3-(2-quinolinylmethyloxy)aniline is used in place of 3-aminobenzonitrile and 3-cyanobenzoic acid is used in place of 3-(2-quinolinylmethyloxy) benzoic acid, then the product prepared is 5-(3-(3-(2-quinolinylmethyloxy)anilinocarbonyl)phenyl)tetrazole.

In a similar manner, the compounds of this invention where B is

may be made.

Synthesis of a Compound of Formula (VI)

A compound of formula (VI) is prepared in a multi-step synthesis illustrated in the below scheme. The key starting material is quinaldine. In the first stage it is chlorinated to form 2-chloromethylquinoline which, without isolation, is reacted with hydroquinone to form the intermediate 4-(quinolin-2-yl-methoxy)phenol (VIII). This intermediate is then treated with α,α'-dichloro-o-xylene to form 2-[4-quinolin-2-yl-methoxy)phenoxymethyl]benzyl chloride, which is converted in situ to 2-[4-quinolin-2-yl-methoxy)phenoxymethyl]phenylacetonitrile (IX), the penultimate precursor to (VI).

(IX) is converted to (VI) crude, in a reaction with sodium azide and ammonium chloride which transforms the nitrite group into the tetrazole ring. The purification of the final product is accomplished by recrystallization of the crude material from methanol to afford pure (VI).

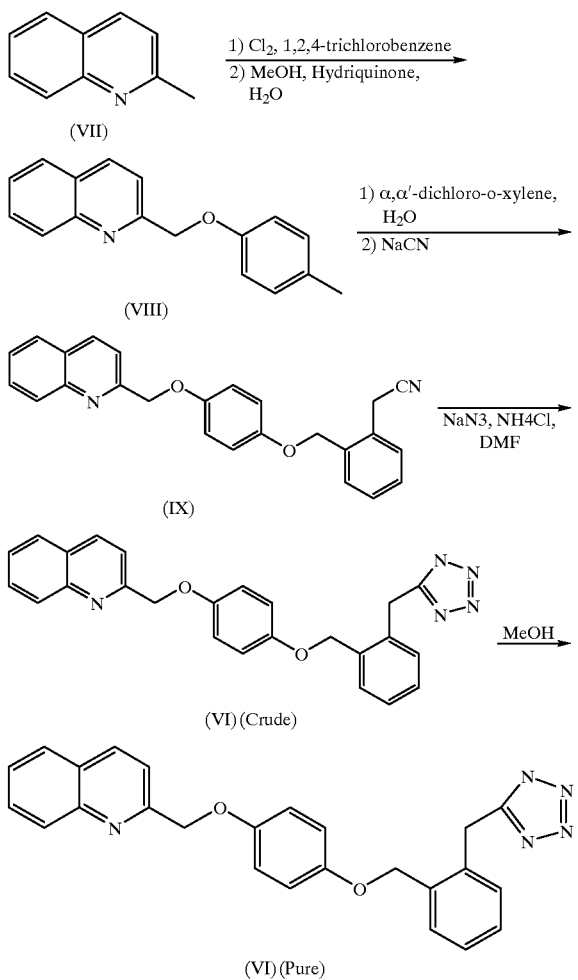

The methods described above are used to prepare the following compounds of this invention.

5-[2-(4-(2-quinolinylmethoxy)phenoxymethyl)benzyl]tetrazole (M.P. 108–111° C.)
CALC: C, 59.87; H, 5.96; N, 13.96.
FOUND: C, 59.67, 60.01; H, 5.62, 5.63; N, 13,73, 13.77.
5-[4-Methoxy-3-(3-(2-quinolinylmethoxy)phenoxymethyl)phenyl]tetrazole (M.P. 184–87° C.)
CALC: C, 67.63; H, 4.88; N, 15.78.
FOUND: C, 67.18; H, 5.13; N, 15.40.
5-[3-(4-(2-quinolinylmethyloxy)phenoxymethyl)phenyl]tetrazole (M.P. 176–177° C.)
CALC: C, 69.63; H, 4.75; N, 16.92.
FOUND: C, 69.58, 69.64; H, 5.00, 4.98; N, 16.66, 16.63.
5-[3-Methoxy-4-(4-(2-quinolinylmethyloxy)benzyloxy)phenyl]tetrazole (M.P. 195–97° C.)
CALC: C, 67.63; H, 4.88; N, 15.77.
FOUND: C, 67.27; H, 4.89; N, 15.41.
5-[4-(3-(2-quinolinylmethyloxy)phenoxymethyl)-3methoxyphenyl]tetrazole (M.P. 189–91° C.)
CALC: C, 66.95; H, 4.95; N, 15.61.
FOUND: C, 66.48; H, 5.14; N, 14.93.
5-[3-(4-(2-quinolinylmethyloxy)phenoxymethyl)benzyl]tetrazole (M.P. 139–44° C.)
CALC: C, 70.53; H, 5.03; N, 16.45.
FOUND: C, 70.33, 70.54; H, 5.25, 5.36; N, 16.38, 16.41.
5-[4-(4-(2-quinolinylmethyloxy)phenoxymethyl)benzyl]tetrazole (M.P. 167–71° C.)
CALC: C, 67.33; H, 5.31; N, 15.70.
FOUND: C, 67.54, 67.67,; H, 5.33, 5.33; N, 15.48, 15.52.
5-[4-Methoxy-3-(4-(2-quinolinylmethyloxy)phenylmethyloxy)phenyl]tetrazole (M.P. 210–13° C.)
CALC: C, 68.33; H, 4.82; N, 4.90.
FOUND: C, 68.32; H, 4.90; N, 14.79.
4-[3-(2-Quinolinylmethyloxy)phenoxymethyl]phenoxyacetic acid (M.P. 164 (dec))
CALC: C, 69.27; H, 5.35; N, 3.23.
FOUND: C, 69.53, 69.65; H, 5.11, 5.05; N, 3.21, 3.12.
5-[2-(4-(2-Quinolinylmethyloxy)phenoxymethyl)phenoxymethyl]tetrazole (M.P. 183–85° C.)
CALC: C, 65.63; H, 5.08; N, 15.31.
FOUND: C, 65.77, 65.52; H, 4.99, 5.03; N, 14.92, 15.03.
4-[4-(2-Quinolinylmethyloxy)phenoxymethyl]phenoxyacetic acid (176° C. (dec))
CALC: C, 71.50; H, 5.16; N, 3.34.
FOUND: C, 71.10, 71.17; H, 5.27, 5.33; N, 3.37, 3.34.
4-[3-(2-Quinolinylmethyloxy)phenoxymethyl]phenylacetic acid (M.P. 158–60° C.)
CALC: C, 75.17; H, 5.30; N, 3.51.
FOUND: C, 74.89; H, 5.36; N, 3.37.
2-[3-(3-(2-Quinolinylmethyloxy)phenoxymethyl)phenoxy]pentanoic acid (M.P. 133–35° C.)
CALC: C, 73.51; H, 5.95; N, 3.06.
FOUND: C, 73.35, 73.60; H, 5.95, 5.98; N, 3.08, 3.05.
2-[3-(2-Quinolinylmethyloxy)phenoxymethyl]phenoxyacetic acid (M.P. 169–172° C.)
CALC: C, 72.28; H, 5.10; N, 3.37.
FOUND: C, 69.34, 69.69; H, 5.10, 5.13; N, 3.00, 3.08.
CALC: C, 69.27; H, 5.35; N, 3.23 (as Hydrate).
2-[4-(2-Quinolinylmethyloxy)phenoxymethyl]cinnamic acid (M.P. 175–178° C.)
CALC: C, 75.90; H, 5.14; N, 3.40.
FOUND: C, 73.92; H, 5.20; N, 3.01.
CALC: C, 74.27; H, 5.27; N, 3.33 (as Hydrate).
6-Acetyl-2-propyl-3-[3-(2-quinolinylmethyloxy)-benzyloxy]phenoxyacetic acid (M.P. 153–58° C.)
CALC: C, 72.13; H, 5.85; N, 2.90.
FOUND: C, 71.68, 72.08; H, 5.88, 5.83; N, 2.65, 2.70.
2-[2-(4-(7-Chloroquinolin-2-ylmethyloxy)-phenoxymethyl)phenoxy]propionic acid (M.P. 169–173° C.)
CALC: C, 67.32; H, 4.78; N, 3.02; Cl, 7.64.
FOUND: C, 65.18; H, 4.90; N, 2.84; Cl, 8.33.
CALC: C, 65.41; H, 4.96; N, 2.93; Cl, 7.42 (as HYDRATE).
2-[4-(2-Quinolinylmethyloxy)phenoxymethyl]phenylacetic acid (M.P. 181–83° C.)
CALC: C, 75.17; H, 5.30; N, 3.51.
FOUND: C, 75.12, 74.96; H, 5.50, 5.49; N, 3.16, 3.16.
3-[3-(2-Quinolinylmethyloxy)phenoxymethyl]phenoxyacetic acid (M.P. 146–51° C.)
CALC: C, 72.28; H, 5.10; N, 3.37.
FOUND: C, 71.82, 71.80; H, 5.24, 5.23; N, 2.98, 3.00.
CALC: C, 71.50; H, 5.16; N, 3.34 (as HYDRATE).
2-[4-(2-Quinolinylmethyloxy)phenoxymethyl]phenoxyacetic acid (M.P. 153–57° C.)
CALC: C, 72.28; H, 5.10; N, 3.37.
FOUND: C, 72.30, 71.72; H, 5.39, 5.30; N, 2.94, 2.89.
5-[2-(4-(7-Chloroquinolin-2-ylmethyloxy)-phenoxymethyl)benzyl]tetrazole (M.P. 159–63° C.)
CALC: C, 65.57; H, 4.40; N, 15.29.
FOUND: C, 64.16; H, 4.72; N, 14.98.
CALC: C, 64.30; H, 4.53; N, 14.99 (as HYDRATE).

2-Carbomethoxy-5-[3-(2-quinolinylmethyloxy)-phenoxymethyl]phenoxyacetic acid (M.P. 187–89° C.)
    CALC: C, 68.49; H, 4.90; N, 2.95.
    FOUND: C, 66.71; H, 4.96; N, 2.70.
    CALC: C, 66.59; H, 5.07; N, 2.87 (as HYDRATE).
2-[3-(2-Quinolinylmethyloxy)phenoxymethyl]-6-methylphenoxyacetic acid (M.P. 149–53° C.)
    CALC; C, 72.71; H, 5.40; N, 3.26.
    FOUND: C, 71.23; H, 5.46; N, 3.08.
    CALC: C, 71.22; H, 5.51; N, 3.19 (as HYDRATE).
2-[3-(3-(2-Quinolinylmethyloxy)phenoxymethyl)phenoxy]glutaric acid (M.P. 129–30° C.)
    CALC: C, 69.00; H, 5.17; N, 2.87.
    FOUND: C, 58.19; H, 4.93; N, 2.23.
    CALC: C, 58.23; H, 5.17; N, 2.43 (as HYDRATE).
2-[3-(2-Quinolinylmethyloxy)phenoxymethyl]benzylmalonic acid (M.P. 164–65° C.)
    CALC: C, 70.89; H, 4.08; N, 3.06.
    FOUND: C, 70.51,70.61; H, 5.03, 5.24; N, 3.03, 2.90.
2-[2-(3-(2-Quinolinylmethyloxy)phenoxymethyl)phenoxy]pentanoic acid (M.P. 118–20° C.)
    CALC: C, 73.51; H, 5.95; N, 3.06.
    FOUND: C, 73.26; H, 6.07; N, 2.79.
2-[4-(2-Quinolinylmethyloxy)phenoxymethyl]-6-methylphenoxy acetic acid (M.P. –151–53° C.)
    CALC: C, 72.71; H, 5.40; N, 3.26.
    FOUND: C, 71.41; H, 5.58; N, 3.03.
    CALC: C, 71.22; H, 5.51; N, 3.19 (as HYDRATE).
2-[2-(4-(2-Quinolinylmethyloxy)phenoxymethyl)phenoxy]pentanoic acid (M.P. 85–92° C.)
    CALC: C, 73.5 1; H, 5.95; N, 3.06.
    FOUND: C, 71.73, 71.79; H, 5.96, 5.91; N, 3.06, 2.83.
    CALC: C, 72.09; H, 6.05; N, 3.00 (as HYDRATE).
2-Carbomethoxy-5-[4-(2-quinolinylmethytoxy)-phenoxymethyl]phenoxyacetic acid (M.P. 149–51° C.)
    CALC: C, 68.49; H, 4.90; N, 2.95.
    FOUND: C, 68.00, 68.08; H, 4.98, 5.04; N, 2.90, 2.90.
2-[2-(4-(2-Quinolinylmethyloxy)phenoxymethylphenoxy]propionic acid (M.P. 161–64° C.)
    CALC: C, 72.71; H, 5.40; N, 3.26.
    FOUND: C, 70.96, 71.10; H, 5.51, 5.58; N, 3.08, 3.10.
    CALC: C, 71.22; H, 5.52; N, 3.19 (as HYDRATE).
2-[2-(3-(2-Quinolinylmethyloxy)phenoxymethyl)phenoxy]glutaric acid (M.P. 83° C. dec)
    CALC: C, 68.98; H, 5.17; N, 2.87.
    FOUND: C, 64.10, 63.75; H, 4.89, 4.92; N, 2.64, 2.69.
    CALC: C, 63.74; H, 5.63; N, 2.65(as HYDRATE).
2-(3-[2-Quinolinylmethyloxy]benzyloxy)phenoxyacetic acid (M.P. 153–55° C.)
    CALC: C, 72.28; H, 5.10; N, 3.37.
    FOUND: C, 71.75; H, 5.14; N, 3.38.
    CALC: C, 71.50; H, 5.16; N, 3.34 (as HYDRATE).
2-(2-[4-(2-Quinolinylmethyloxy)phenoxymethyl]-4chlorophenoxy)propionic acid (M.P. 196–99° C.)
    CALC: C, 67.32; H, 4.78; N, 3.02.
    FOUND: C, 67.40, 67.43; H, 4.89, 4.94; N, 3.01, 3.13.
2-(2-[3-(2-Quinolinylmethyloxy)phenoxymethyl]-4chlorophenoxy)propionic acid (M.P. 169–71° C.)
    CALC: C, 67.32; H, 4,78; N, 3.02.
    FOUND: C, 65.47; H, 5.31; N, 2.78.
    CALC: C, 65.41; H, 4.96; N, 2.93 (as HYDRATE).
2-(2-[3-(2-Quinolinylmethyloxy)phenoxymethyl]-4chlorophenoxy)pentanoic acid (M.P. 144–45° C.)
    CALC: C, 68.36; H, 5.33; N, 2.85.
    FOUND: C, 67.74, 67.86; H, 5.39, 5.47; N, 2.91, 2.84.
    CALC: C, 67.74; H, 5.38; N, 2.82 (as HYDRATE).
2-(2-[4-(2-Quinolinylmethyloxy)phenoxymethyl]-4-chlorophenoxy)pentanoic acid (M.P. 155–56° C.
    CALC: C, 68.36; H, 5.33; N, 2.85.
    FOUND: C, 65.96; H, 5.59; N, 2.66.
    CALC: C, 65.95; H, 5.53; N, 2.75 (as HYDRATE).
2-(2-[4-(2-Quinolinylmethyloxy)phenoxymethyl]-4-chlorophenoxy)pentanoic acid (M.P. 155–56° C.
    CALC: C, 68.36; H, 5.33; N, 2.85.
    FOUND: C, 66.15; H, 5.58; N, 2.68.
    CALC: C, 65.95; H, 5.53; N, 2.75 (as HYDRATE).
2-(2-[4-(2-Quinolinylmethyloxy)phenoxymethyl]-6-chlorophenoxy)pentanoic acid (M.P. 161–62° C.
    CALC: C, 68.36; H, 5.33; N, 2.85.
    FOUND: C, 68.15; H, 5.36; N, 2.72
2-(2-[3-(2-Quinolinylmethyloxy)phenoxymethyl]-6-chlorophenoxy)pentanoic acid (M.P. 169–70° C.)
    CALC: C, 68.36; H, 5.33; N, 2.85.
    FOUND: C, 68.10; H, 5.39; N, 2.72.
2-(2-[3-(2-Quinolinylmethyloxy)phenoxymethyl]-6-chlorophenoxy)-4-methylpentanoic acid (M.P. 164–66° C.)
    CALC: C, 68.84; H, 5.58; N, 2.77.
    FOUND: C, 68.84; H, 5.70; N, 2.69.
2-(2-[4-(2-Quinolinylmethyloxy)phenoxymethyl]-6-chlorophenoxy)-4-methylpentanoic acid (M.P. 167–69° C.)
    CALC: C, 68.84; H, 5.58; N, 2.77.
    FOUND: C, 68.78; H, 5.67; N, 2.68.
5-[3-(3-(2-quinolinylmethyloxy)benzyloxy)-4-methoxyphenyl]tetrazole (M.P. 204–07° C.)
    CALC: C, 67.63; H, 4.88; N, 15.78.
    FOUND: C, 67.11; H, 5.15; N, 15.86.
N-[3-Methoxy-4-(3-(2-quinolinylmethyloxy)benzyloxy)benzoyl)benzene sulfonamide hydrochloride (M.P. dec.88)
    CALC: C, 62.99; H, 4.60; N, 4.74.
    FOUND: C, 63.88; H, 5.13; N, 4.80.
5-Carboxy-2-(3-(2-quinolinylmethyloxy)phenoxymethyl)phenoxy acetic acid (M.P. 226–28° C.)
    CALC: C, 61.90; H, 5.18; N, 2.77.
    FOUND: C, 61.62; H, 5.11; N, 2.67.
5-[3-Methoxy-4-(3-(2-quinolinylmethyloxy)benzyloxy)phenyl]tetrazole (M.P. 204–05° C.)
    CALC: C, 67.67; H, 5.14; N, 15.87.
    FOUND: C, 67.63; H, 4.88; N, 15.78.
5-(4-(3-(2-Quinolinylmethyloxy)benzyloxy)phenyl)tetrazole (M.P. 233–36° C.)
    CALC: C, 69.58; H, 4.73; N, 16.91.
    FOUND: C, 69.59; H, 4.89; N, 16.91.

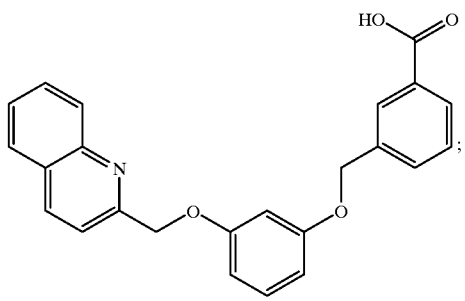

MP 149–151° C.

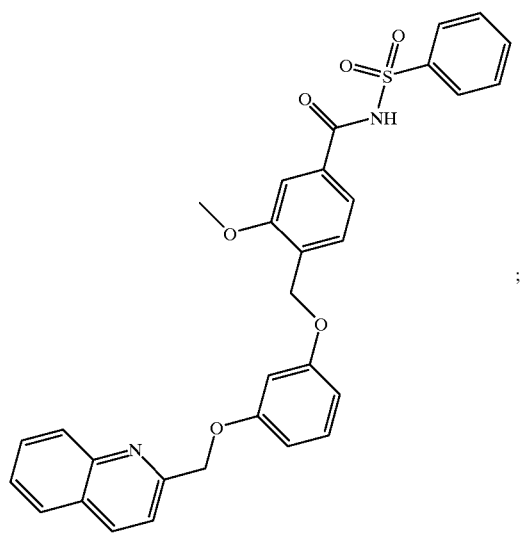
MP 156–158° C.
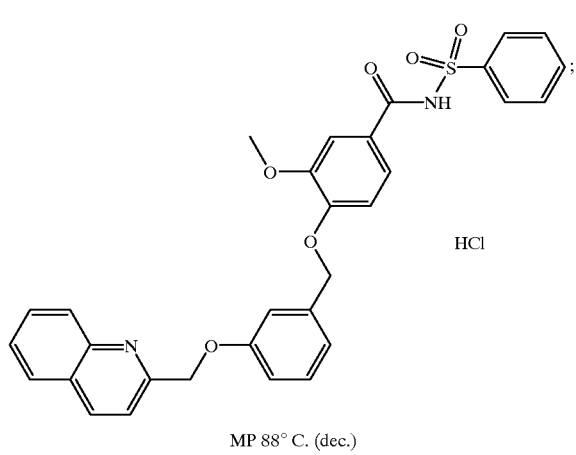
HCl
MP 88° C. (dec.)
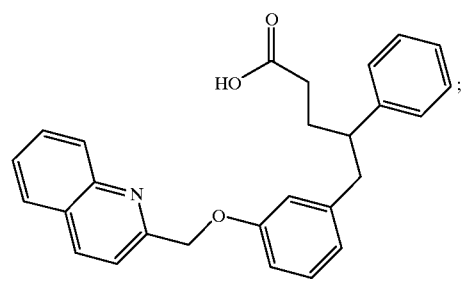
MP 112–116° C.
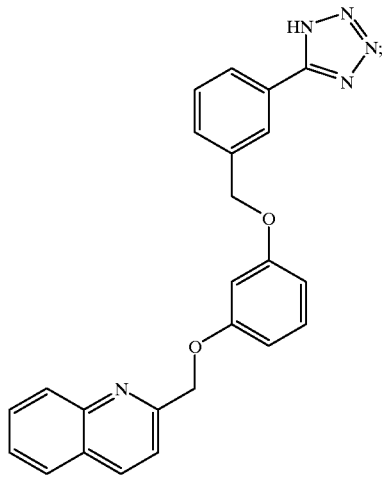
M.P. 115° C. (dec.)
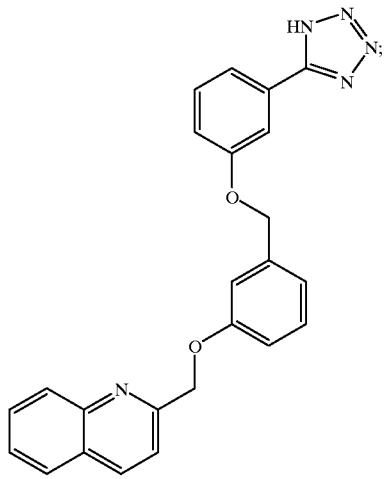
M.P. 169–72° C.
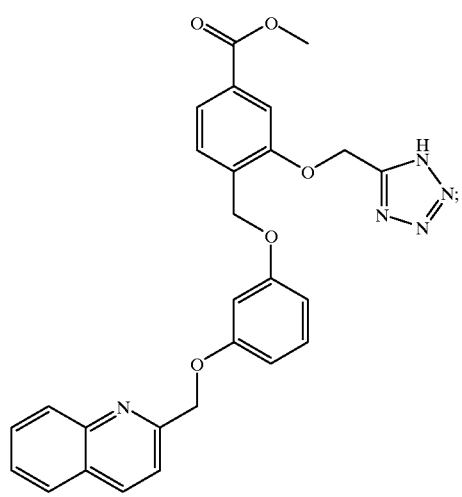
M.P. 159–62° C.

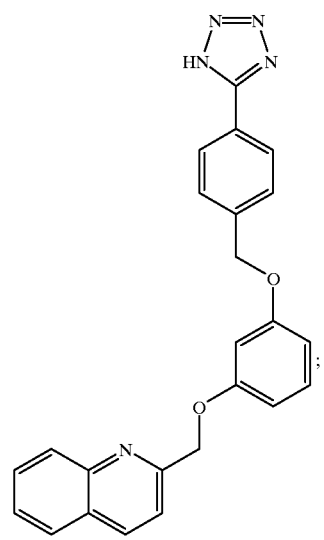
M.P. 91° C.
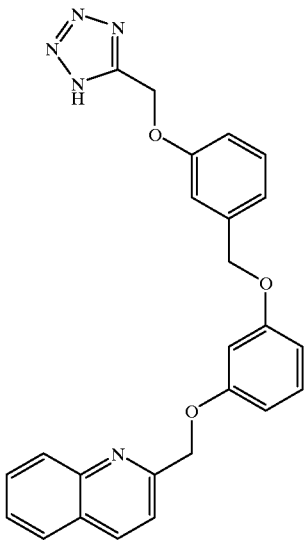
M.P. 135–37° C.
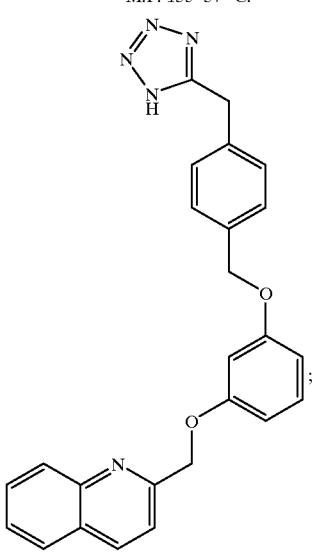
M.P. 210–13° C.
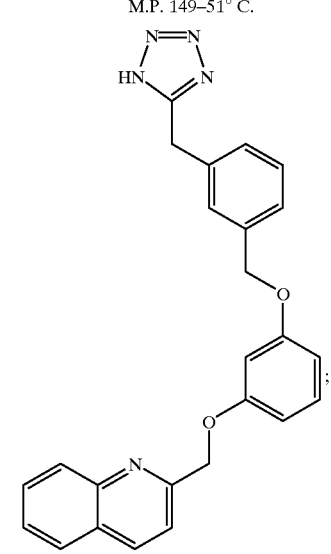
M.P. 149–51° C.
M.P. 154–56° C.
M.P. 161–64° C.

-continued
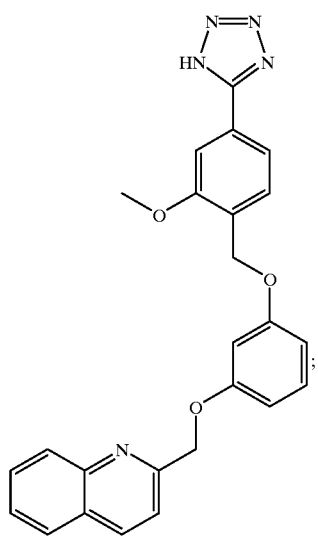
M.P. 204–5° C.
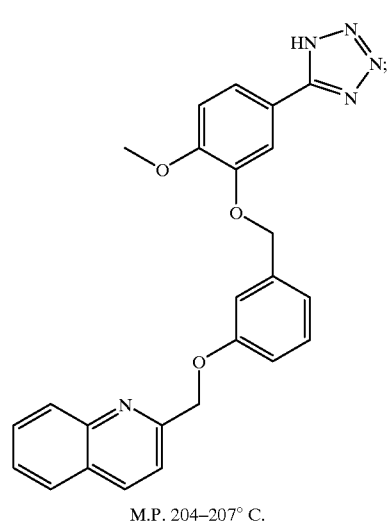
M.P. 204–207° C.
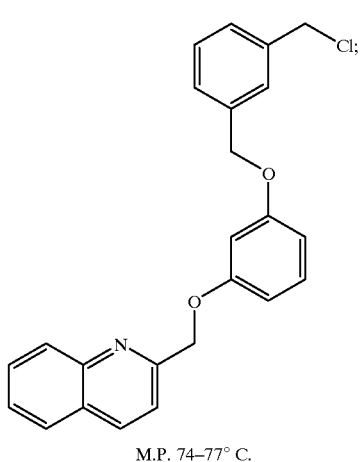
M.P. 74–77° C.
-continued
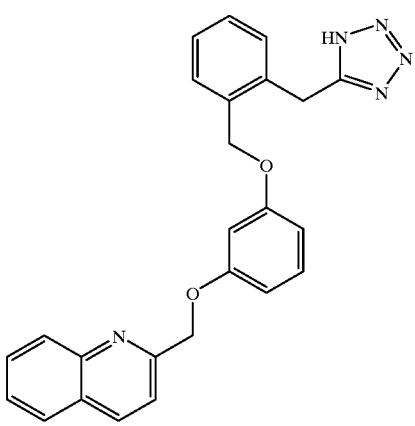
M.P. 144–47° C.
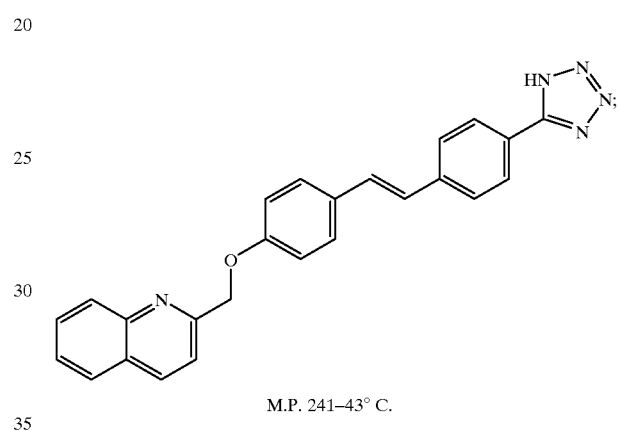
M.P. 241–43° C.
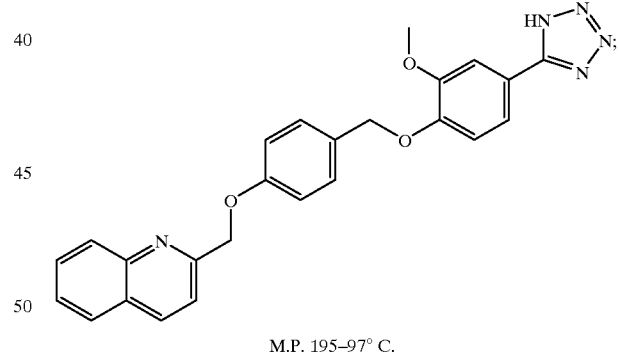
M.P. 195–97° C.
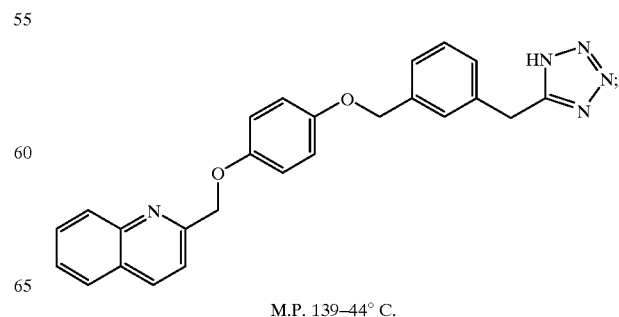
M.P. 139–44° C.

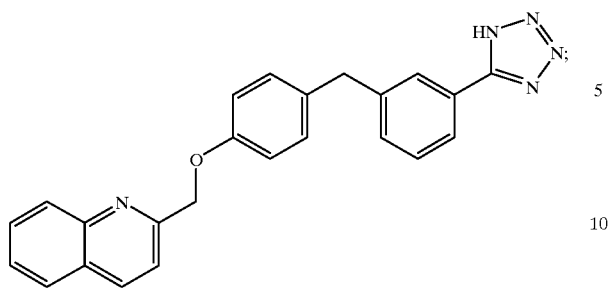
M.P. 186–89° C.
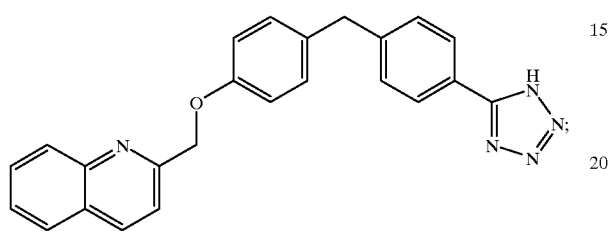
M.P. 206–209° C.
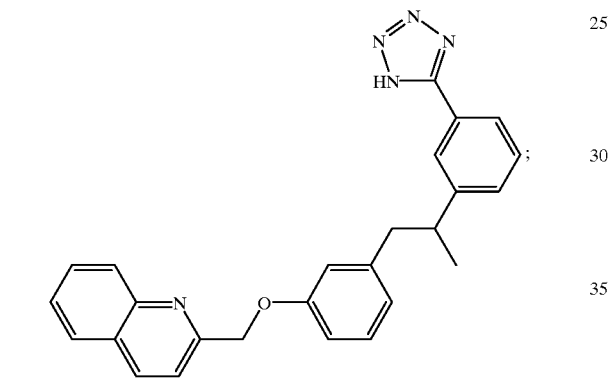
M.P. 83–86° C.
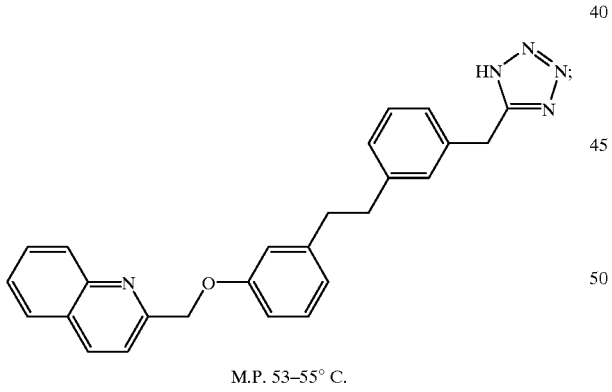
M.P. 53–55° C.
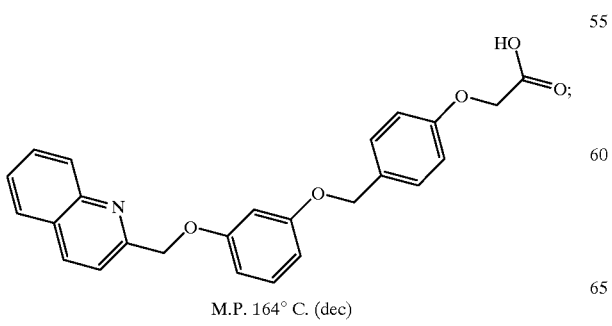
M.P. 164° C. (dec)
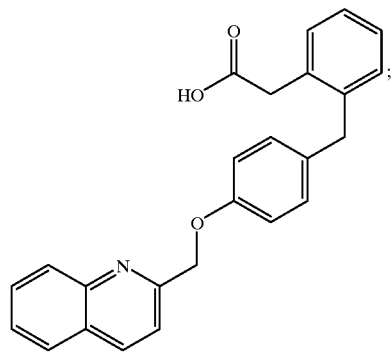
M.P. 183–86° C.
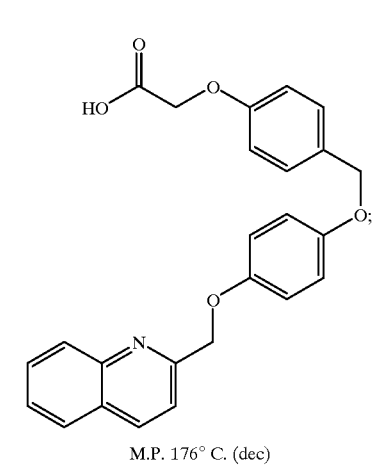
M.P. 176° C. (dec)
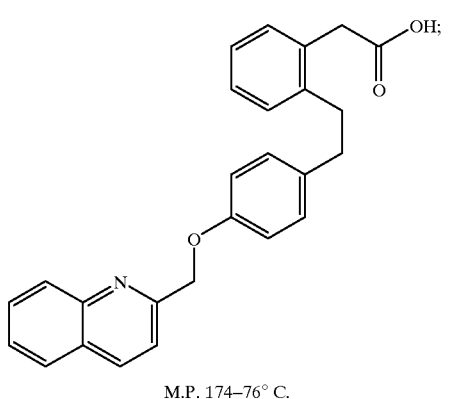
M.P. 174–76° C.
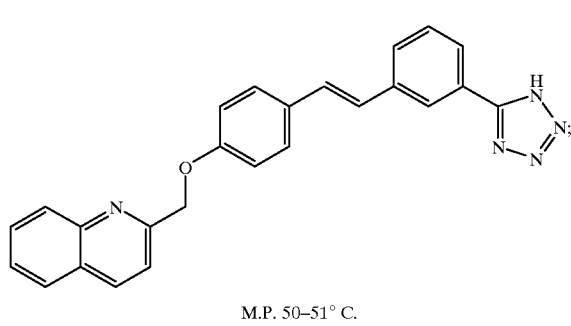
M.P. 50–51° C.

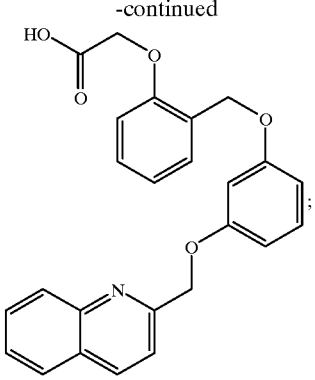
M.P. 169–72° C.
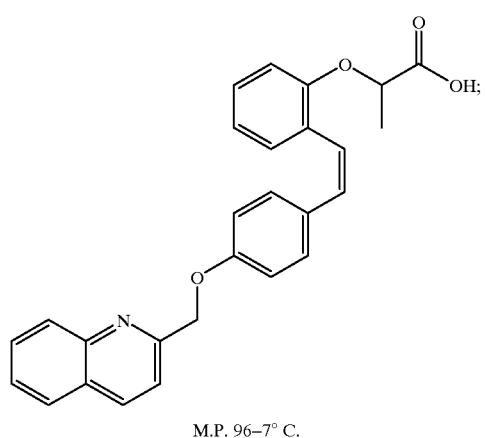
M.P. 96–7° C.
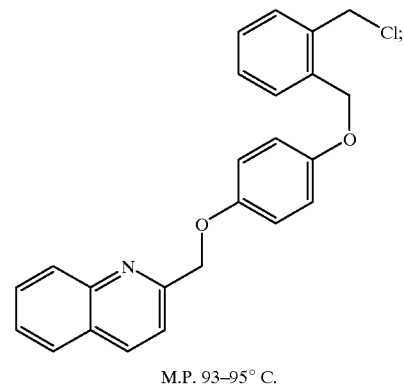
M.P. 93–95° C.
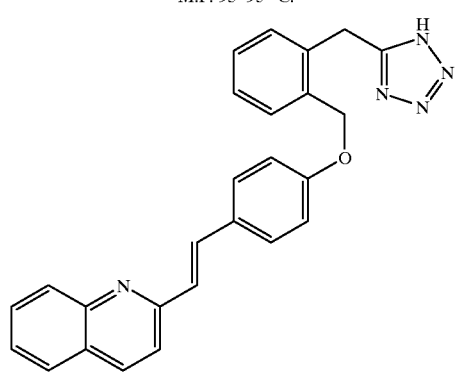
M.P. 191–96° C.
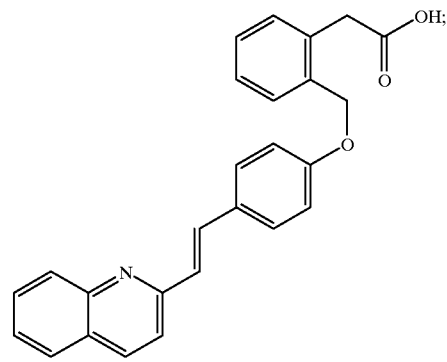
M.P. 180–82° C.
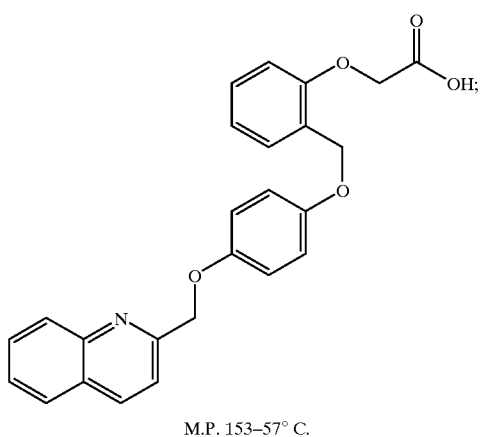
M.P. 153–57° C.
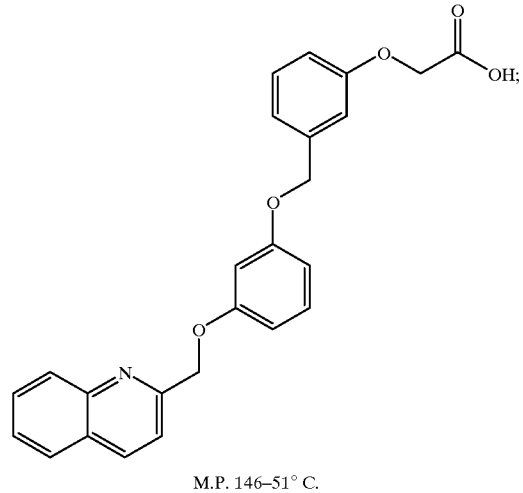
M.P. 146–51° C.
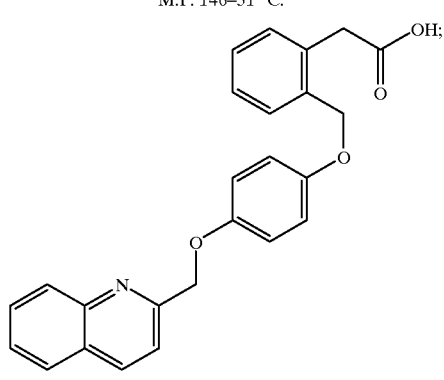
M.P. 181–183° C.

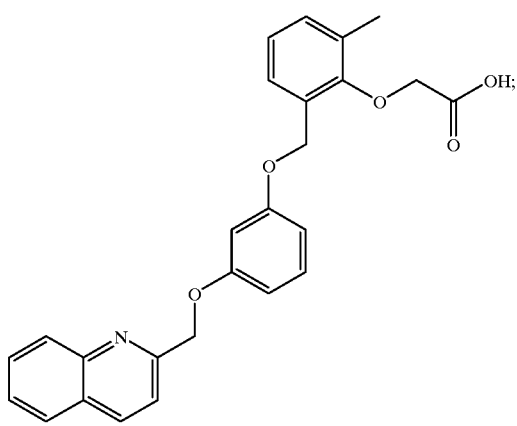
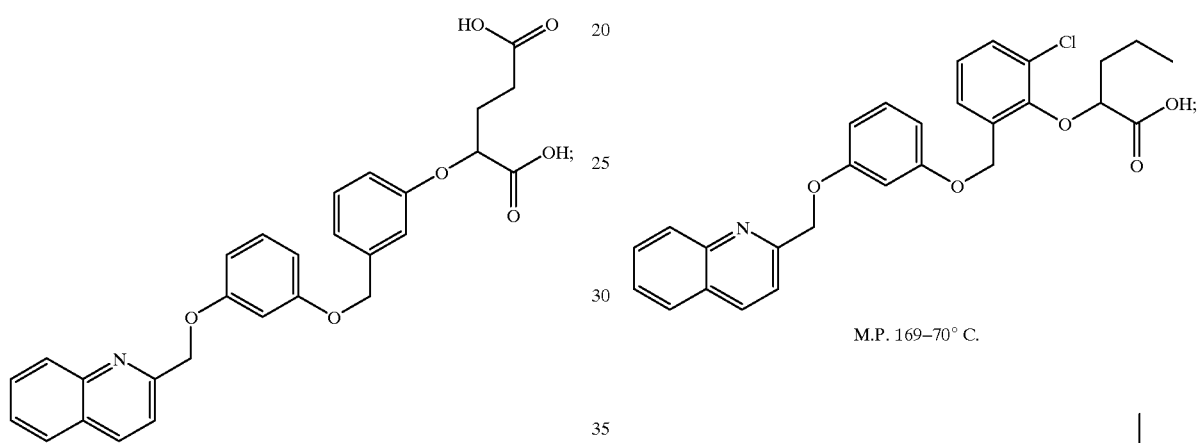
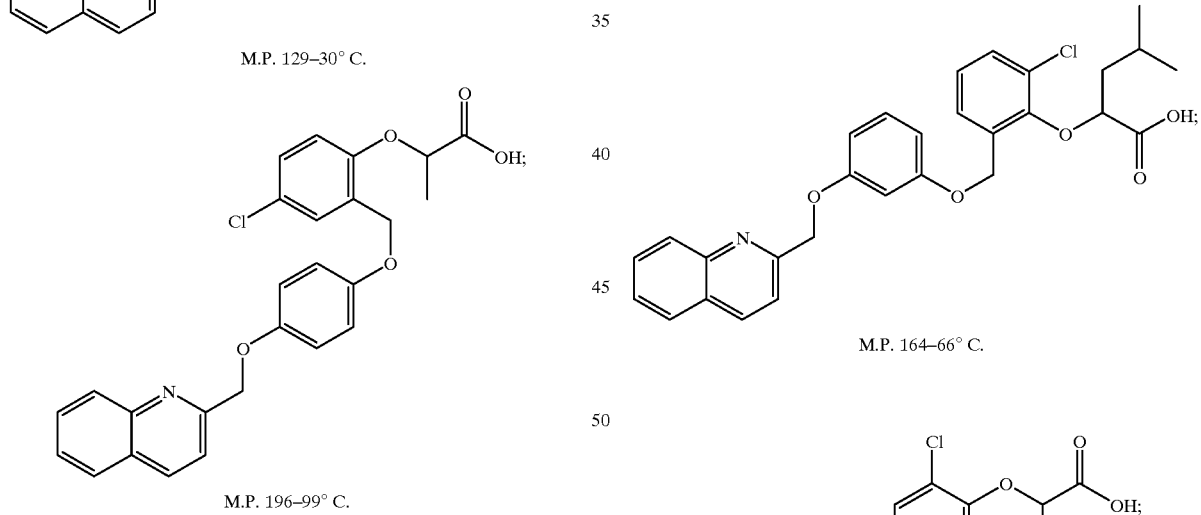
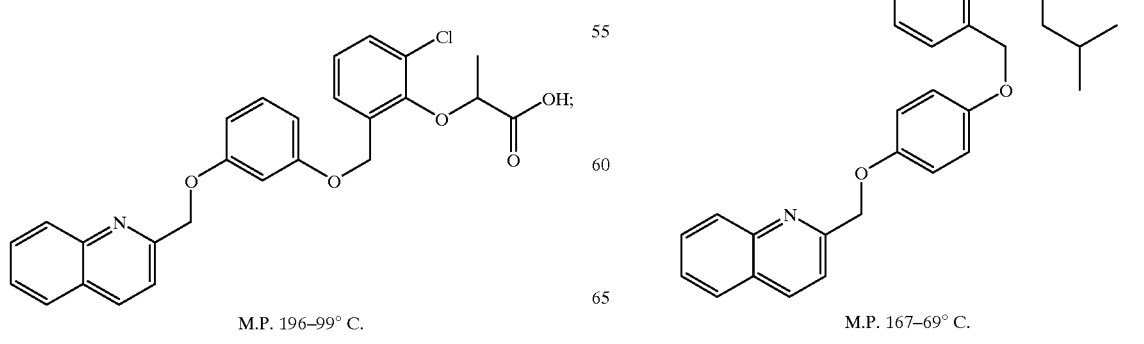

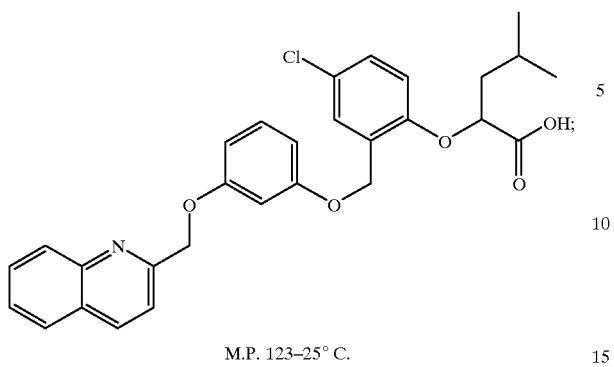
M.P. 123–25° C.
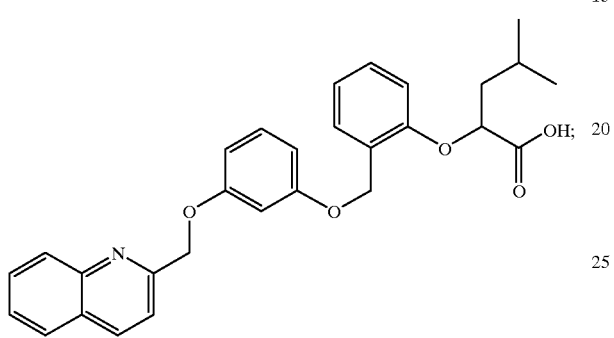
M.P. 76–87° C.
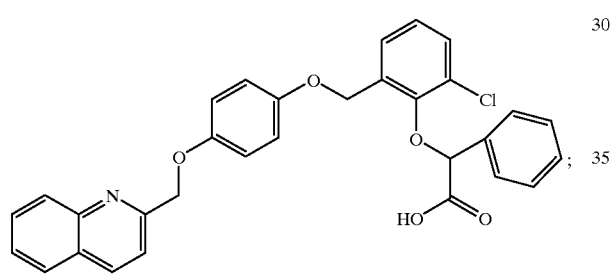
M.P. 156–57° C.
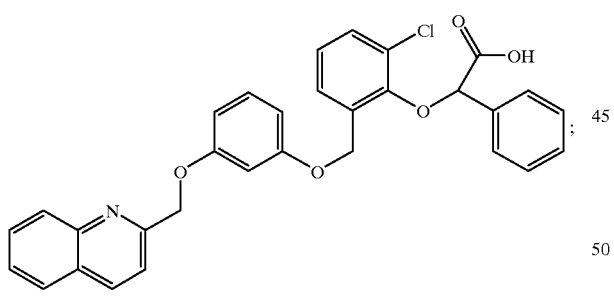
M.P. 180–81° C.
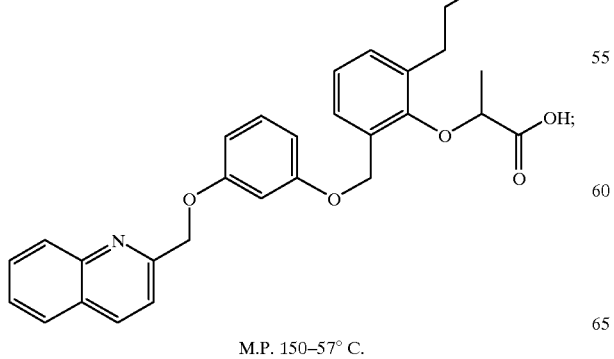
M.P. 150–57° C.
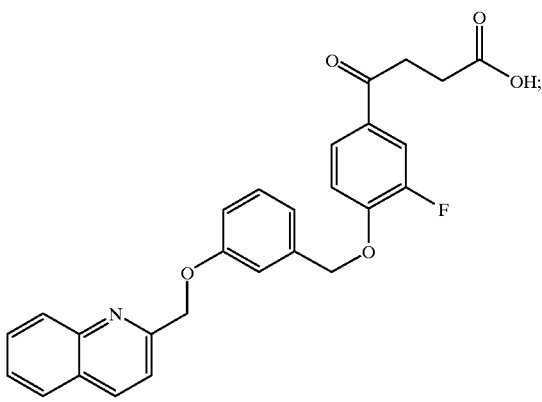
M.P. 145–47° C.
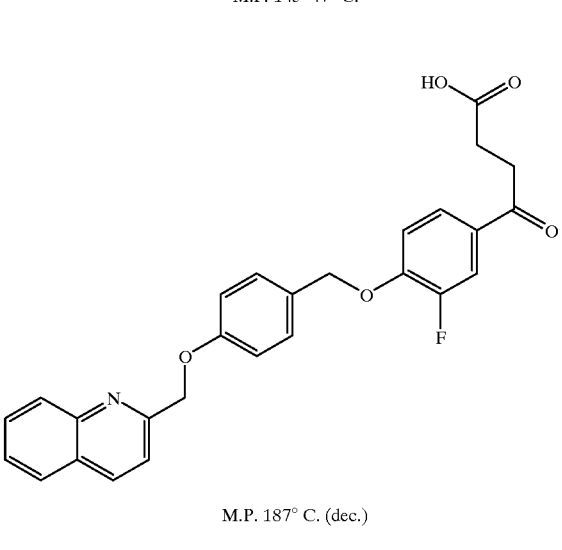
M.P. 187° C. (dec.)
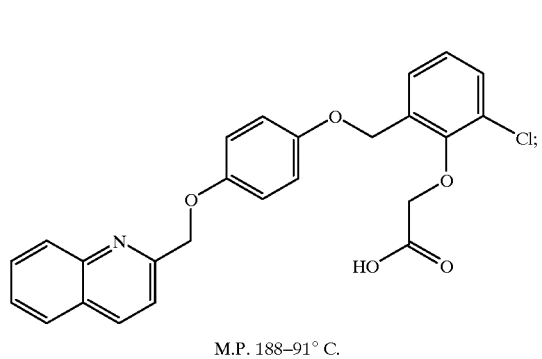
M.P. 188–91° C.
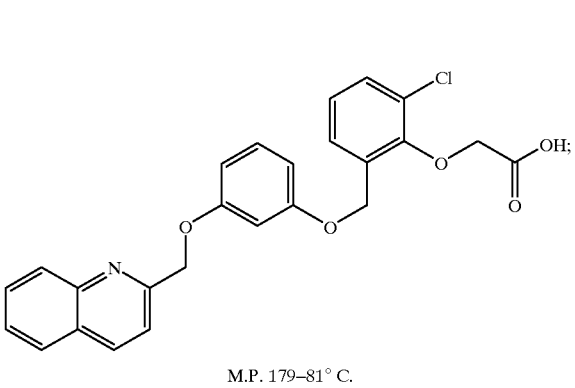
M.P. 179–81° C.

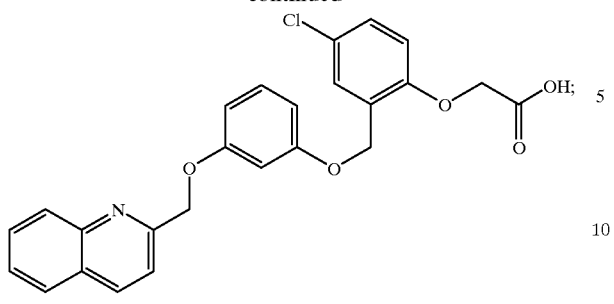
M.P. 189–91° C.
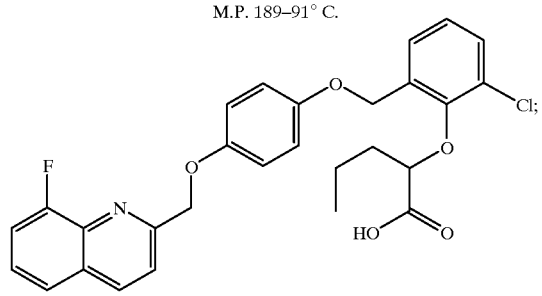
M.P. 173–77° C.
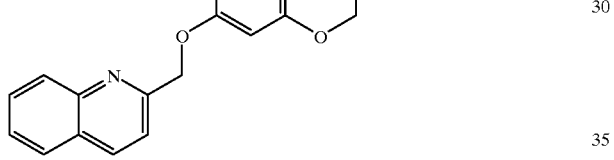
Calc: C, 76.46; H, 6.42; N, 3.07.
Found: C, 74.10; H, 6.16; N, 2.93.
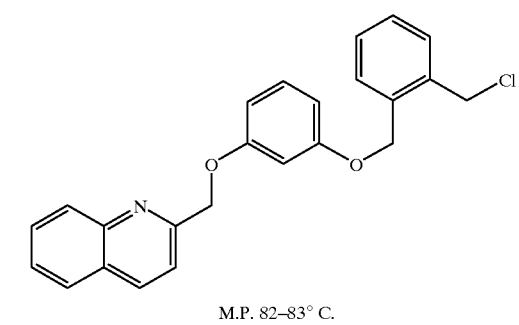
M.P. 82–83° C.
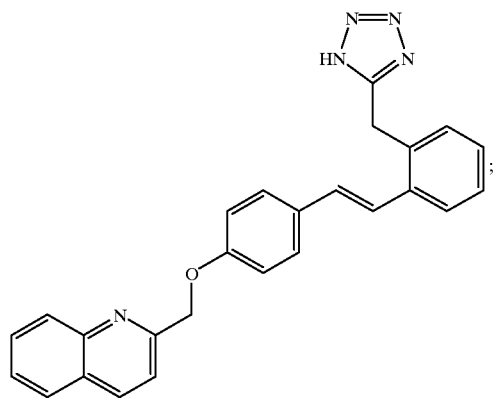
M.P. 138–40° C.
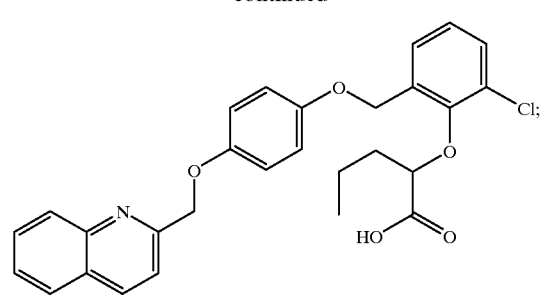
M.P. 161–162° C.
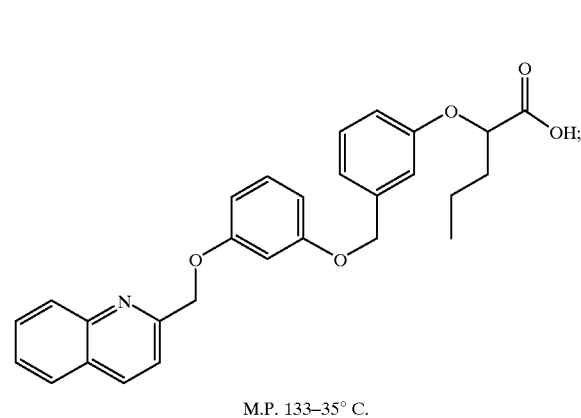
M.P. 133–35° C.
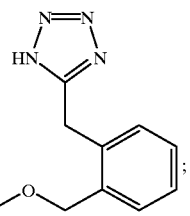
M.P. 152–55° C.
M.P. 174–75° C.
and -continued

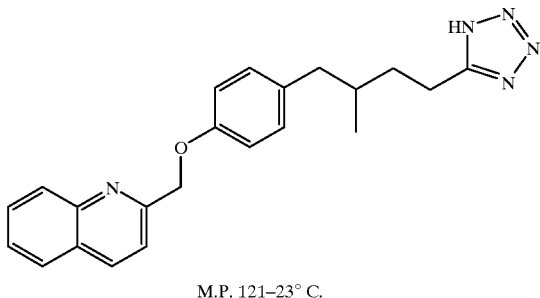

M.P. 121–23° C.

Using a combination of the above Examples, various compounds may be made within the scope of this invention.

Compounds according to the invention exhibit marked pharmacological activities according to tests described in the literature which tests results are believed to correlate to pharmacological activity in humans and other mammals. The following pharmacological test results are typical characteristics of compounds of the present invention.

The compounds of the present invention have potent activity as PPAR-γ ligand receptor binders and possess anti-diabetic, anti-lipidemic, anti-hypertensive, and anti-arteriosclerotic activity and are also anticipated to be effective in the treatment of diabetes, obesity and other related diseases.

The activity of the compound of formula VI was examined in several relevant in vitro and in vivo preclinical assays, benchmarking with Troglitazone®. Initial results show that the compound of formula VI is a more potent PPAR-γ ligand receptor binder than Troglitazone® and shows significantly better efficacy in diabetic models.

It was determined that the compounds of the invention act through the PPAR-γ pathway and the biological efficacy in the appropriate in vitro and in vivo models were evaluated. These experiments included benchmarking against a known therapeutic compound in the field, Troglitazone® (CSO-45). The assays carried out are as follows:

Adipocyte Differentiation
  Evaluation of the capacity to induce differentiation of primary human pre-adipocyte cultures to adipocytes.
LTD$_4$ Binding
  The data obtained for the compound of formula VI shows it to be a potent antagonist of the guinea pig receptor (Kd=3 nM).
Oral efficacy in db/db mice
  An in-feed study in this genetic model of type II diabetes was performed. The two specific aims of this study were to demonstrate efficacy and to determine potency relative to the marketed compound, Troglitazone®.

Adipocyte Differentiation

The capacity of Compound VI to induce adipocyte differentiation of primary human pre-adipocyte cultures was evaluated and compared directly to Troglitazone®.

Human subcutaneous preadipocytes were isolated from adipose tissue obtained by liposuction surgery. Preadipocytes were inoculated at high density in preadipocyte medium (DME/F-10, 1:1, (v/v) containing 10% fetal calf serum). Cells were kept in preadipocytic medium overnight for attachment. Drug treatment was initiated the second day by changing to serum free medium containing the tested compound at the appropriate concentration. The basal medium, which was used as the negative control, contained DME/F-10, biotin (33 μM), pantothenate (17 μM), insulin (100 nM), and dexamethasone (1 μM). The culture was maintained for 14 days with the compound treatment during the first five days. At the end of the culture, cells were fixed in 5% formalin and stained with oil red-O dye. The dye was extracted by isopropanol and quantitated by measuring the optical density at 500 nm.

Figure 2:
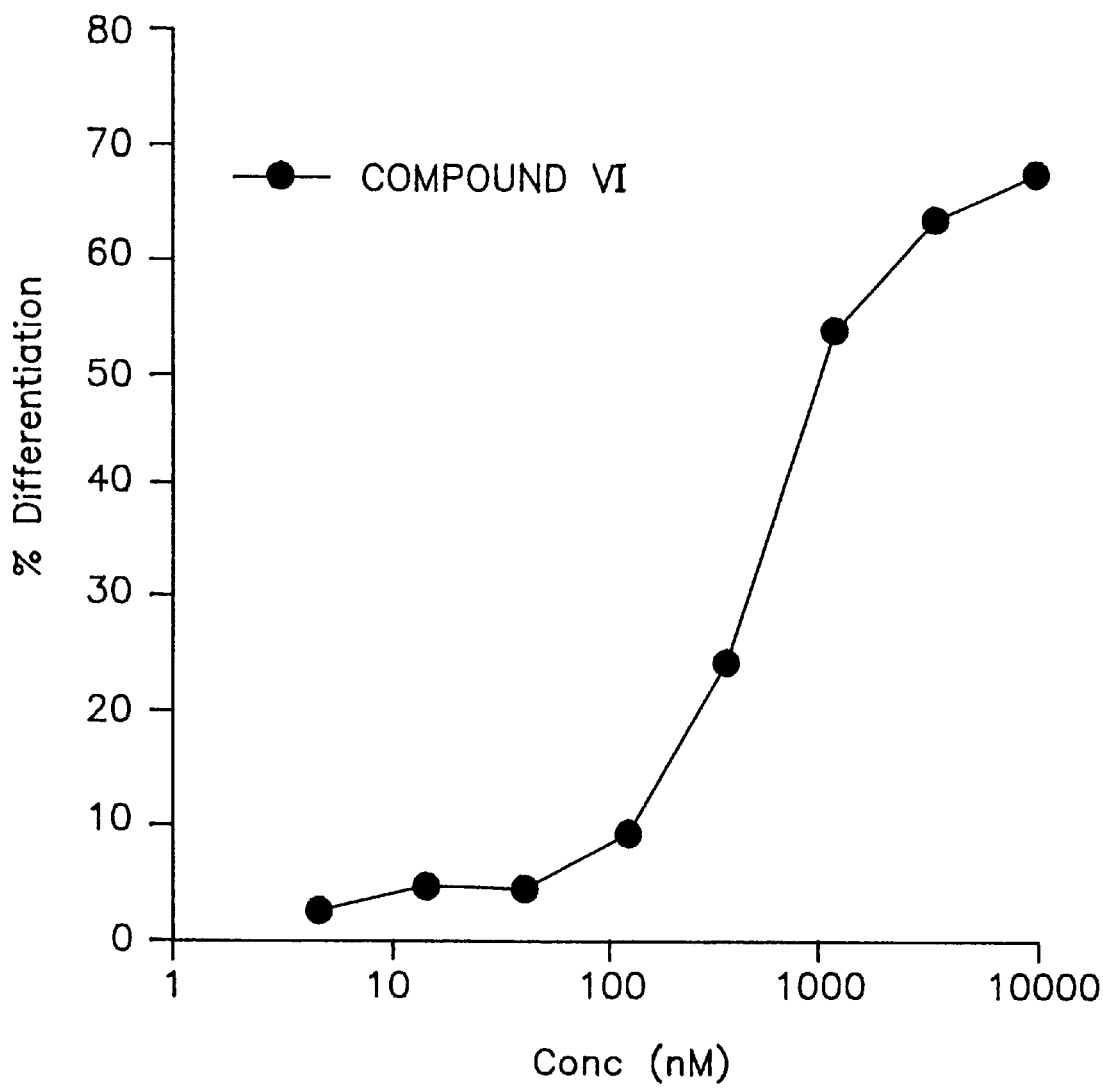
FIG. 2 represents a graph of the effect of the compound of formula VI on the adipocyte differentiation of human preadipocytes.
Figure 3A:
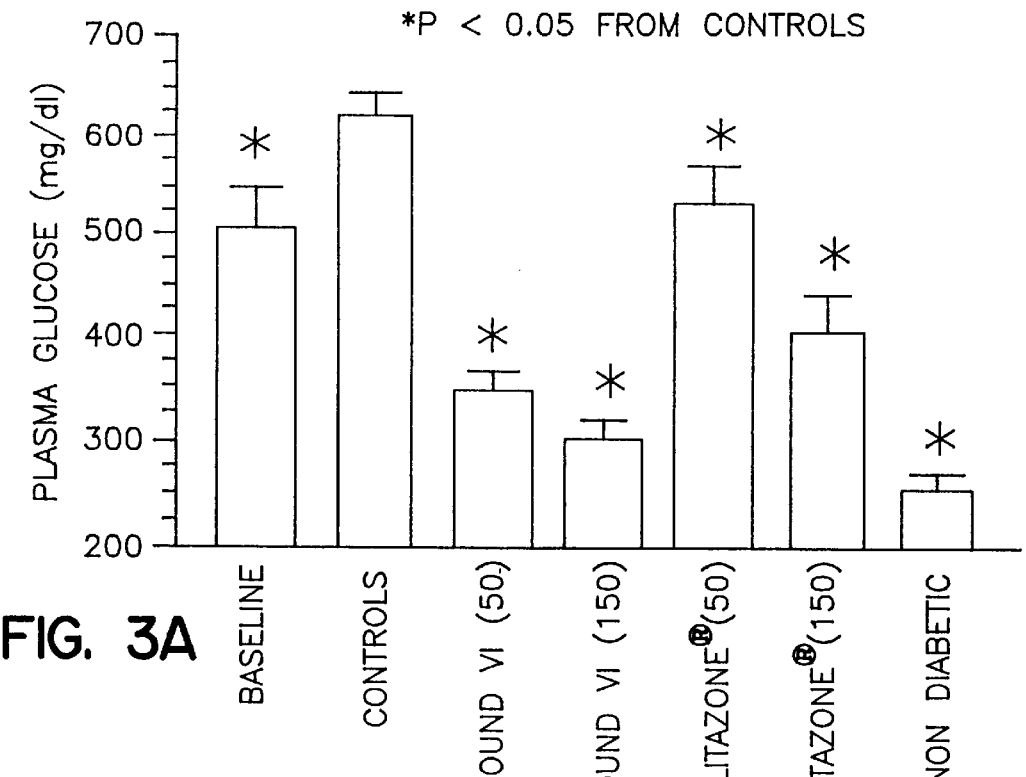
FIG. 3A represents graphs of the effect of the compound of formula VI and Troglitazone® on plasma parameters in the mouse db/db model of type II diabetes wherein the groups of animals (n=12) were administered compounds as a mixed feed and wherein the plasma parameter is plasma glucose.
Figure 3B:
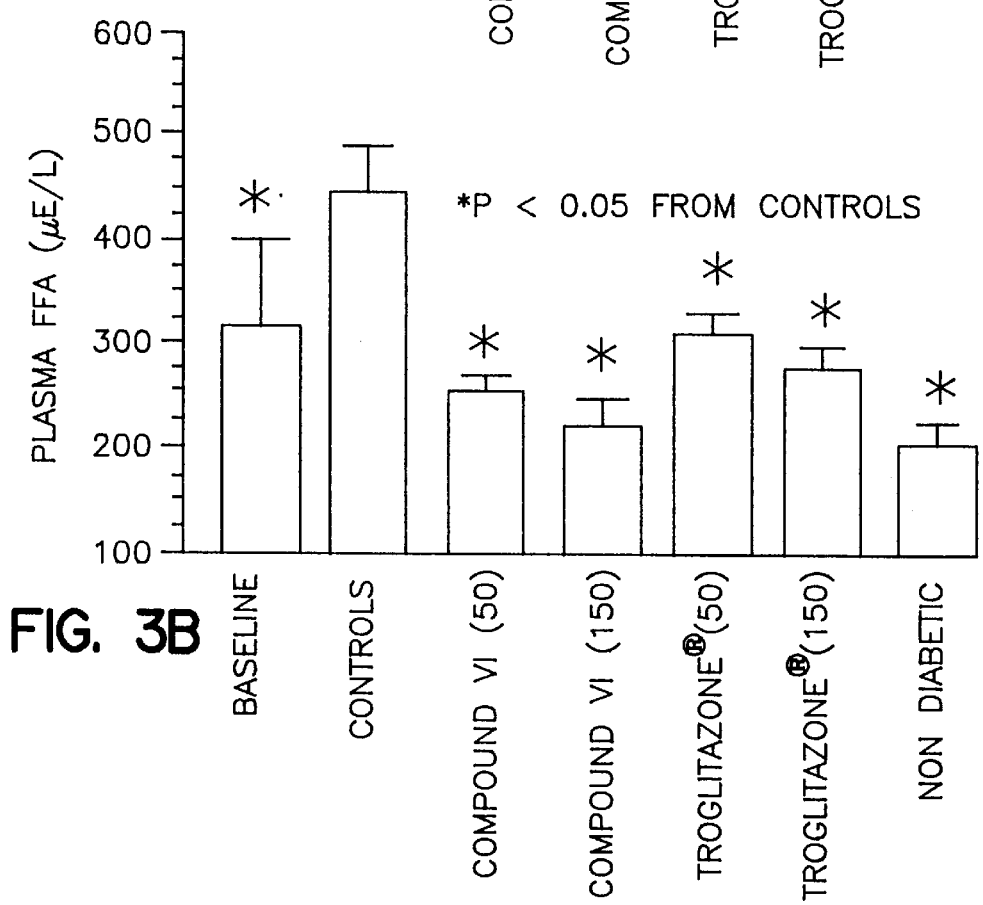
FIG. 3B represents graphs of the effect of the compound of formula VI and Troglitazone® on plasma parameters in the mouse db/db model of type II diabetes wherein the groups of animals (n=12) were administered compounds as a mixed feed and wherein the plasma parameter is free fatty acids (FFA).
Figure 3C:
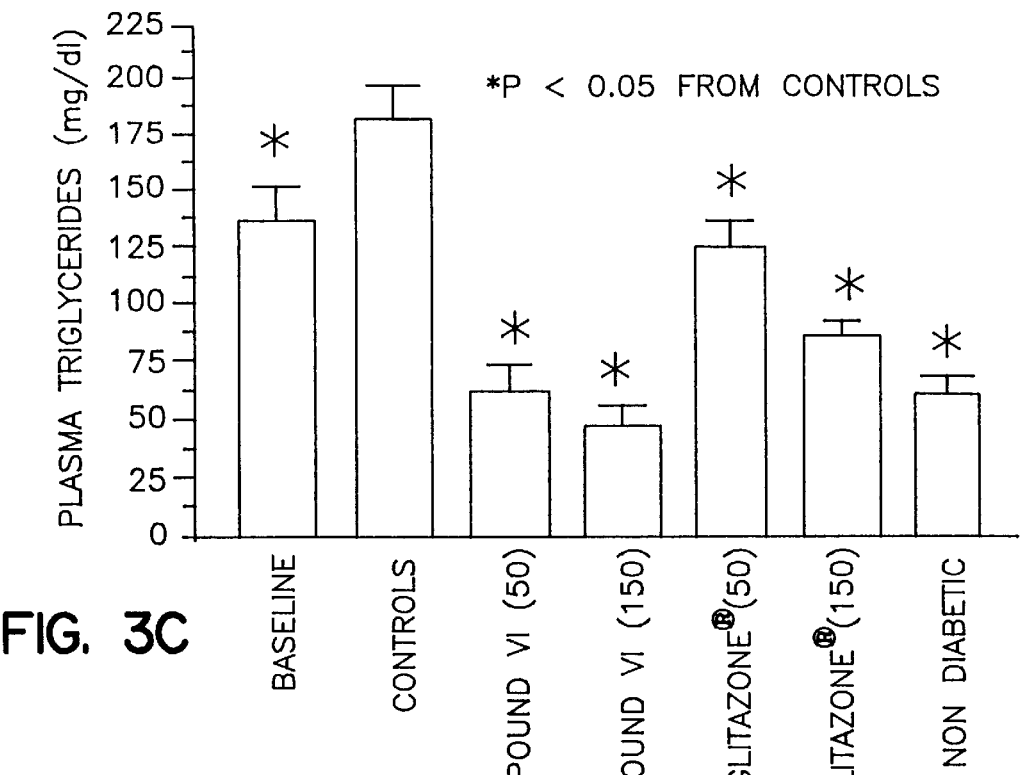
FIG. 3C represents graphs of the effect of the compound of formula VI and Troglitazone® on plasma parameters in the mouse db/db model of type II diabetes wherein the groups of animals (n=12) were administered compounds as a mixed feed and wherein the plasma parameter is triglycerides.
Figure 3D:
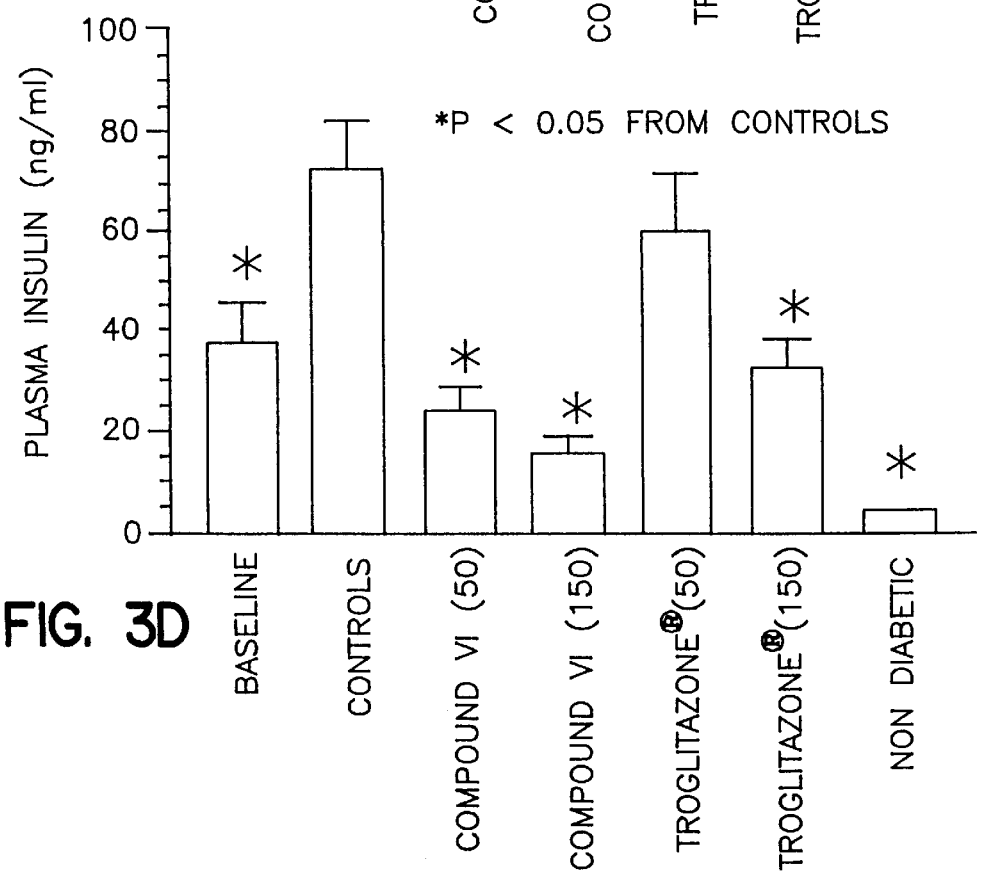
FIG. 3D represents graphs of the effect of the compound of formula VI and Troglitazone® on plasma parameters in the mouse db/db model of type II diabetes wherein the groups of animals (n=12) were administered compounds as a mixed feed and wherein the plasma parameter is insulin.

The in vitro results are summarized in the table below and in FIG. 1 and FIG. 2. These results show that the compound of formula VI is active in the differentiation assay and has better potency than Troglitazone® (CS-045) in the assay. The compound of formula VI also binds tightly to the LTD$_4$ receptor, while Troglitazone® is devoid of this activity.

TABLE 1

Summary of EC$_{50}$/IC$_{50}$ (nM) for PPAR ligand receptor binding

|  | Adipocyte[a] Differentiation | LTD$_4$[b] Binding |
|---|---|---|
| Compound VI | 100–300 | 38 |
| Compound VI in serum | 1000–3000 | 88 |
| Troglitazone ® (Rezulin ™) | >3000 | >10000 |

[a]Human adipocyte differentiation of compound in presence of insulin and dexamethasone
[b]K$_b$ for binding of compound to the LTD$_4$ receptor in THP-1 cells The Compound of Formula VI in db/db Mice The compound of formula VI and Troglitazone® were studied in a genetic model of diabetes (db/db mice). A total of 70 female db/db mice (C57Bl/Ks db+/+; Jackson Labs, Maine), 3 months of age, received either meal chow only (rodent chow # 5001), 50 or 150 mg/kg/day of the compound of formula VI and 50 or 150 mg/kg/day of Troglitazone® mixed with the food. Six animals were sacrificed on Day 0 to obtain baseline values, the remaining 64 animals were randomly distributed into 5 groups. On days 0, 8, 12 and 16 whole blood samples were taken via the tail vein and blood glucose was determined (in duplicate) using the One Touch® gluco-meter. On Day 16, animals were anesthetized using pentobarbital, blood was drawn into EDTA tubes and the following organs were removed: heart, liver, brain, white and brown adipose tissue and the tibia. Plasma was prepared and kept frozen until samples were analyzed for glucose, free fatty acids, insulin and triglycerides.

| Group I | control | control | N = 12 |
|---|---|---|---|
| Group II | locomp. VI | 50 mg/kg/day (compound of formula VI) | N = 13 |
| Group III | hicomp. VI | 150 mg/kg/day (compound of formula VI) | N = 13 |
| Group IV | loTro | 50 mg/kg/day Troglitazone ® | N = 13 |
| Group V | hiTro | 150 mg/kg/day Troglitazone ® | N = 13 |

Plasma was analyzed for glucose, triglycerides, free fatty acids and insulin. The latter two methods were slightly modified to use smaller amounts of plasma. Glucose Analysis. Plasma glucose was measured with a Sigma Chemicals Diagnostic kit (#315-500). Triglyceride Analysis. Plasma triglycerides was measured with a Sigma Chemicals Diagnostic kit (#339-500P). Insulin Analysis. Plasma insulin was measured using a radioimmunoassay (RIA) kit from Linco Research Inc. (#RI-13K). This kit was modified slightly using 10 μl of plasma. This kit utilizes an antibody made specifically against rat insulin. The cross-reactivity of this antibody with mouse insulin is 100 percent. Free Fatty Acid Analysis. Plasma free fatty acids were measured using a kit obtained from Wako Chemicals Inc. (NEFA-C; #994-75409). This kit utilizes an in vitro enzymatic colorimetric method for the quantitation of non-esterified fatty acids in serum or plasma. This method relies upon the acylation of coenzyme A by the fatty acids in the presence of added acyl-CoA synthetase. This method was modified slightly to utilize 5 µl of plasma and was performed in a 96-well format (M. Johnson & J. Peters, *J. Animal Science* 71:753–756, 1993).

Figure 4:
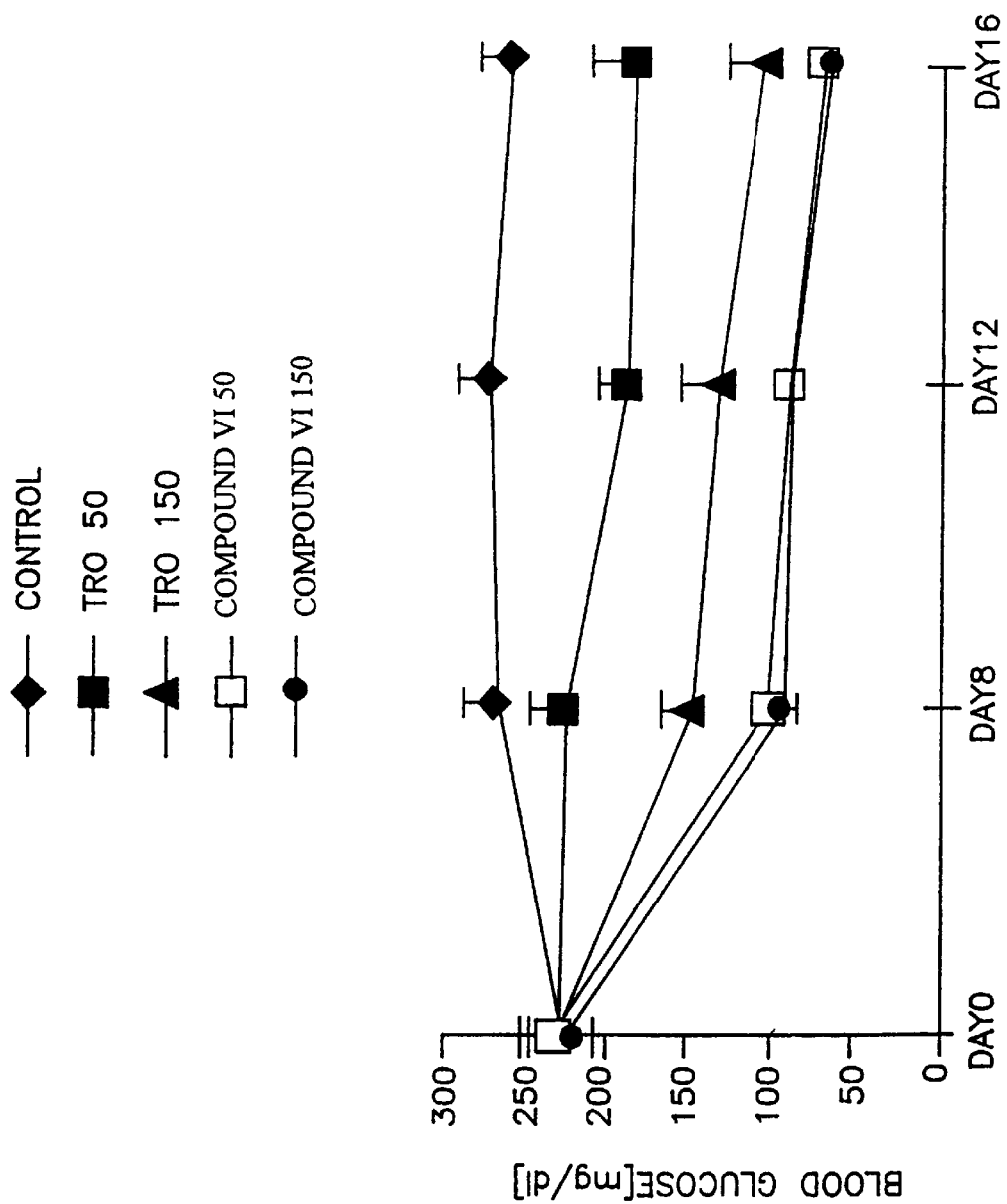
FIG. 4 represents a graph of the time course of the effect of the compound of formula VI and Troglitazone® on lowering blood glucose in the mouse db/db model, with in-feed administration.

The genetically diabetic C57BL/6J-db/db mouse has been used as a counterpart in humans characterised by hyperglycemia, hypertriglyceridemia, insulin resistance and obesity. In the past it has been used as a model to assess the anti-diabetic effects of various therapeutic agents, for example thiazolidinediones, Troglitazone®, englitazone and ciglitazone. Data from the db/db mouse experiment show that the compound of formula VI is effective in this model at lowering glucose, free fatty acids, triglycerides and insulin in this NIDDM model (FIGS. 3A–3D). The profile is parallel to what has been reported for other insulin sensitizers in the thiazolidinedione class of compounds. Additionally, the compound is more efficacious than Troglitazone® at the same doses. Specifically, the data in FIG. 4 shows that Compound VI has at least three times the potency of Troglitazone® in lowering glucose in the db/db mouse. These data suggest that the compound of formula VI has significant oral anti-diabetic activity.

It would be obvious to the skilled person that PPAR-γ ligand receptor binding studies could also be carried out to demonstrate binding of the compounds of the present invention to human PPAR-γ using a known PPAR-γ ligand receptor binder as the radioligand (e.g. $^{14}$C-Troglitazone®). A skilled person could easily synthesise radiolabelled Troglitazone®, for example, by reacting ethyl 3-[4-[(6-acetoxy-2,5,7,8-tetramethylchroman-2-yl)-methoxy]phenyl]-2-chloropropionate with $^{14}$C-thiourea, following the procedure outlined in J. Med. Chem. 1989, 32, 421.

A binding assay for PPAR-γ could be carried out by the following procedure: Purified GST-PPAR-γ-LBD protein (5 mg/100 ml PBS/well) is incubated with shaking in a glutathione coated 96-wells plate (Pierce) for 4 hours (GST= glutathione S-tranferase, LBD=ligand binding domain). The supernants are discarded. The plate is washed three times with the binding buffer (10 mM Tris, 50 mM KCl, 10 mM DTT. 0.05% Tween-20, pH=8.0). For Scatchard analysis, a radiolabelled known PPAR-γ ligand receptor binder (e.g. $^{14}$C-Troglitazone®) is added (5–150 nM) with or without a 100-fold excess of the unlabeled known PPAR-γ ligand receptor binder and incubate at RT for 3 hours. Unbound material is removed by aspiration. The plate is washed three times with the binding buffer. Liquid scintillant is added to the plate (100 ml/well)and the plate counted on a β-counter. For competition binding assays, varying amounts of a compound of the present invention (e.g. the compound of formula VI) (1–200 nM) is added and incubated at RT for 3 hours in the presence of 60 nM of a radiolabelled known PPAR-γ ligand receptor binder. The ligand binding mixtures are aspirated, the plate washed three times with the binding buffer, liquid scintillant is added to the plate (100 ml/well) and the plate read on a β-counter. Inhibition of the binding of the known PPAR-γ ligand receptor binder (e.g. $^{14}$C-Troglitazone®) by a compound of the present invention would be shown in a graph of Specific Activity (cpm) versus Log[inhibitor](nM).

The compounds useful according to the invention can be administered to a patient in a variety of forms adapted to the chosen route of administration, i.e., orally, or parenterally.

Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be from about 2% to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds useful according to this invention may be administered to a patient alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 mM/day or from about 0.1 mg to about 50 mg/kg of body weight per day, or 10 mg to about 50 mg/kg of body eight per day, or more preferably 30 mg to about 50 mg/kg of body weight per day, and higher, although it may be administered in several different dosage units. Higher dosages are required for oral administration.

The compounds useful according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

One skilled in the art will readily appreciate that the present invention is well adapted to carry out the objects of the invention and obtain the ends and advantages mentioned, as well as those inherent therein. The compounds, compositions and method described herein are presented as representative of the preferred embodiments, or intended to be exemplary and not intended as limitations on the scope of the present invention.

We claim:
1. A method of treating a physiological condition in a patient, wherein said condition is associated with a physiologically detrimental level of insulin, glucose, free fatty acids (FFA), or triglycerides comprising administering to the patient a pharmaceutically effective amount of the compound of formula

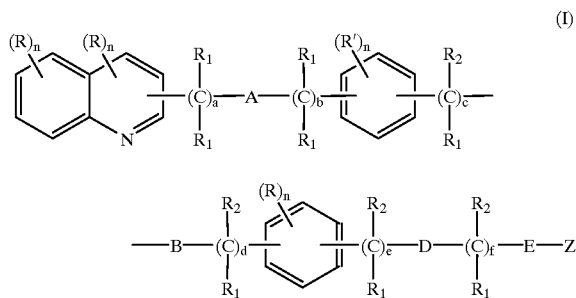

wherein:
A is O, S

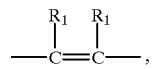

or a chemical bond;
B is O, S, SO, $SO_2$, $NR_1$, a chemical bond,

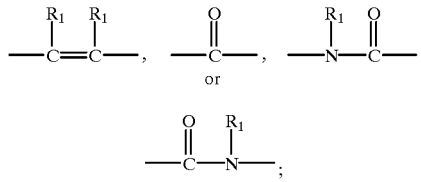

D is O, S, $NR_1$,

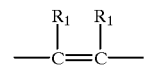

or a chemical bond;
E is a chemical bond or

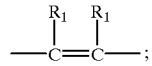

a is 0–2;
b is 0–1;
c is 0–4;
d is 0–5;
e is 0–4;
f is 0–5;
n is 0–2;
R is independently hydrogen, alkyl, hydroxy, alkoxy, carboxy, alkoxycarbonyl, halo, nitro, cyano or acyl;
R' is independently hydrogen, alkyl, hydroxy, alkoxy or halo;
$R_1$ is independently hydrogen, alkyl or aralkyl, or geminal $R_1$ and $R_1$ taken together with the carbon atom to which the geminal $R_1$ and $R_1$ are attached to form =$CHR_1$;
$R_2$ is —$(CH_2)_q$—X, or two vicinal $R_2$ taken together with the carbon atoms through which the two vicinal $R_2$ are linked form cycloalkylene, or geminal $R_1$ and $R_2$ taken together with the carbon atom to which the geminal $R_1$ and $R_2$ are attached form cycloalkylene, =$CHR_1$, or carbonyl;

q is 0–3;

X is hydrogen, alkyl, alkenyl, cycloalkyl, heterocyclyl, aryl, heteroaryl, aralkyl, heteroaralkyl, hydroxy, alkoxy, aralkoxy, heteroaralkoxy, carboxy, alkoxycarbonyl, tetrazolyl, acylHNSO$_2$—, Y$^1$Y$^2$N— or Y$^3$Y$^4$NCO—;

Y$^1$ and Y$^2$ are independently hydrogen, alkyl, aryl, aralkyl or heteroaralkyl, or one of Y$^1$ and Y$^2$ is hydrogen or alkyl and the other of Y$^1$ and Y$^2$ is acyl or aroyl;

Y$^3$ and Y$^4$ are hydrogen, alkyl, aryl, aralkyl or heteroaralkyl;

Z is R$_1$O$_2$C—, CN, halo, R$_3$O$_2$SHNCO—, (R$_1$)$_2$NCO—, R$_1$O— or tetrazolyl; and R$_3$ is hydrogen, alkyl, phenyl or benzyl, or a pharmaceutically acceptable salt thereof.

2. The method according to claim 1, wherein the physiological condition is hyperglycemia.

3. The method according to claim 2, wherein the hyperglycemia is diabetes.

4. The method according to claim 2, wherein the hyperglycemia is Type II diabetes.

5. The method according to claim 1, wherein the physiological condition is hyperinsulinism.

6. The method according to claim 5, wherein the hyperinsulinism is Syndrome X.

7. The method according to claim 1, wherein the physiological condition is insulin resistance.

8. The method according to claim 1, wherein the physiological condition is cardiovascular condition.

9. The method according to claim 8, wherein the cardiovascular condition is atherosclerosis.

10. The method according to claim 1, wherein the physiological condition is hyperlipidemia.

11. The method according to claim 1, wherein the physiological condition is hypertension.

12. The method according to claim 1, wherein the physiological condition is an eating disorder.

13. A method of treating a physiological condition in a patient, wherein said condition is associated with a physiologically detrimental level of insulin, glucose, free fatty acids (FFA), or triglycerides comprising administering to the patient a pharmaceutically effective amount of a compound selected from the group

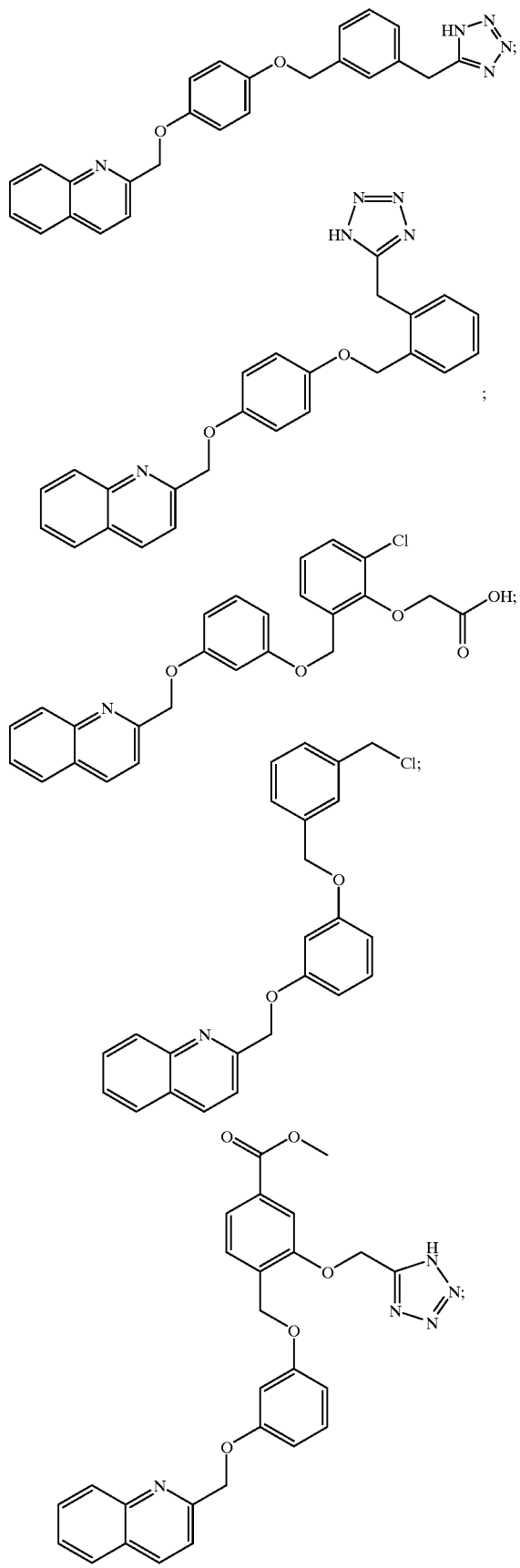

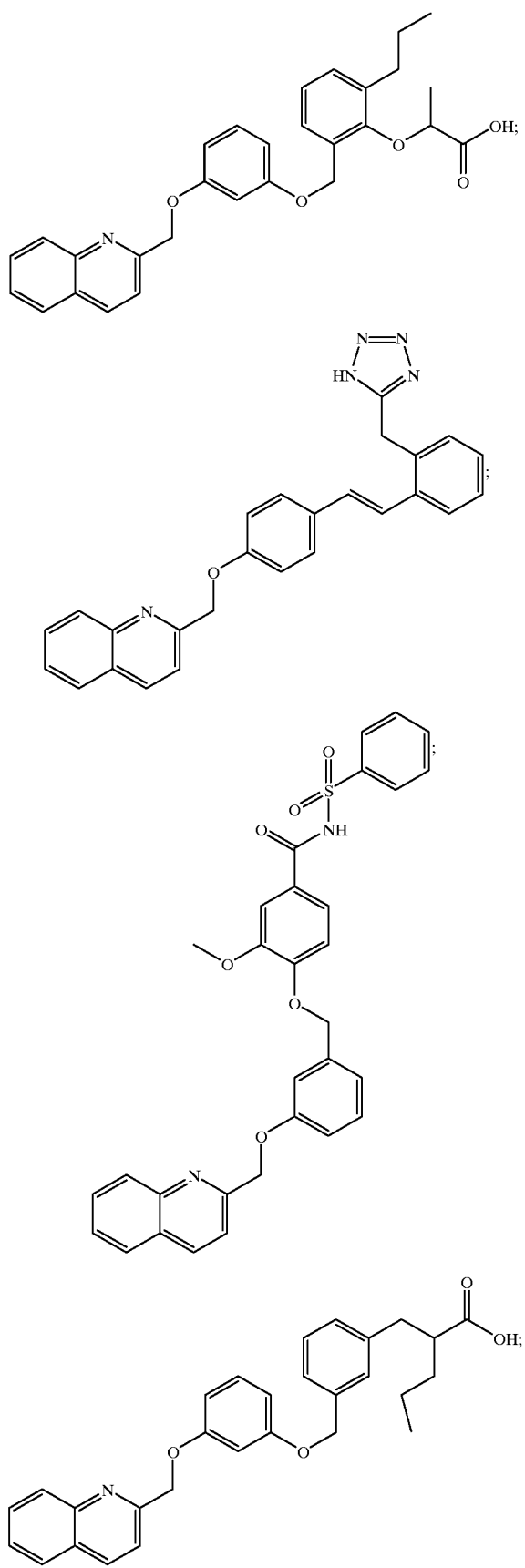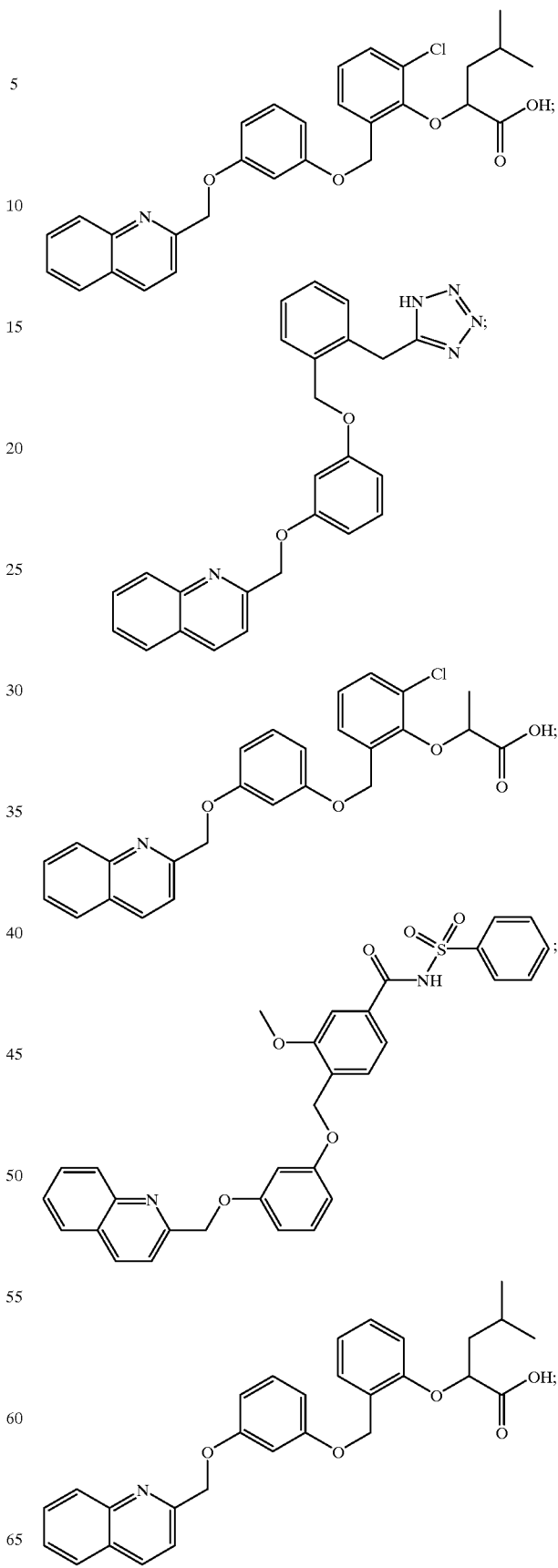

105
-continued
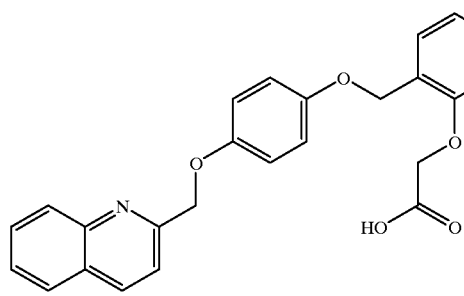
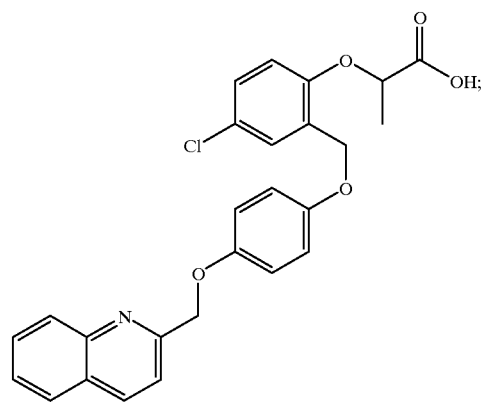
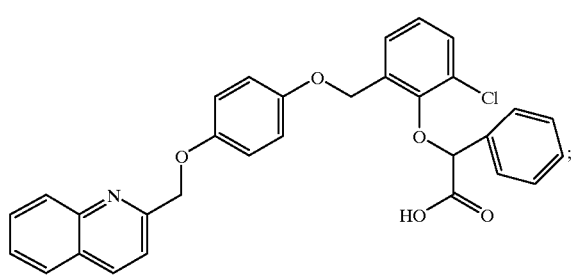
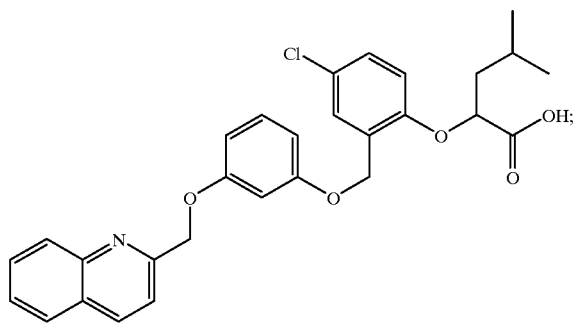
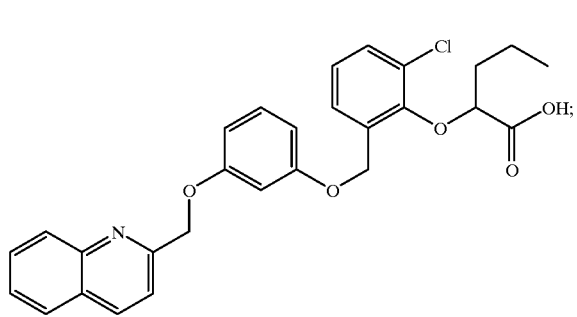
106
-continued
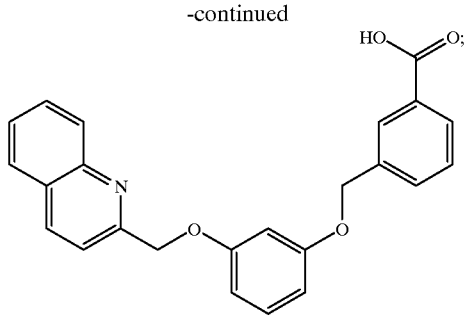
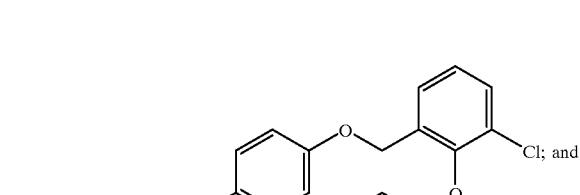
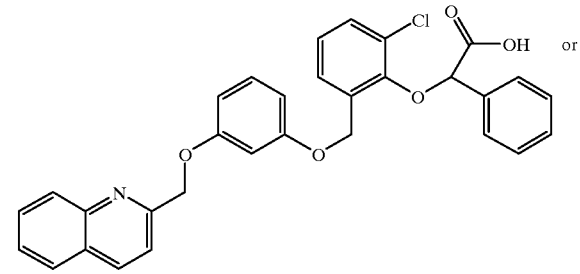
a pharmaceutically acceptable salt thereof.
14. The method according to claim 13 wherein the compound is selected from the group consisting of formulae
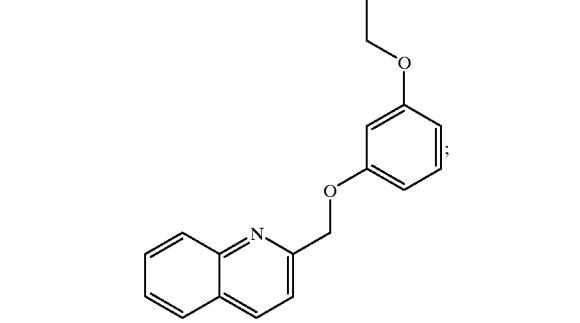

107

-continued

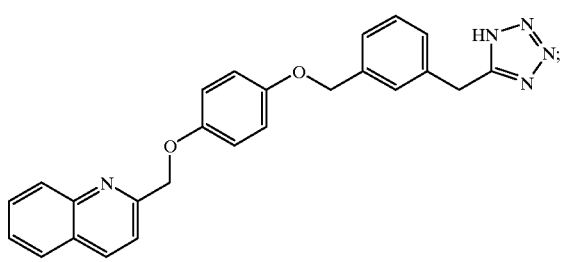

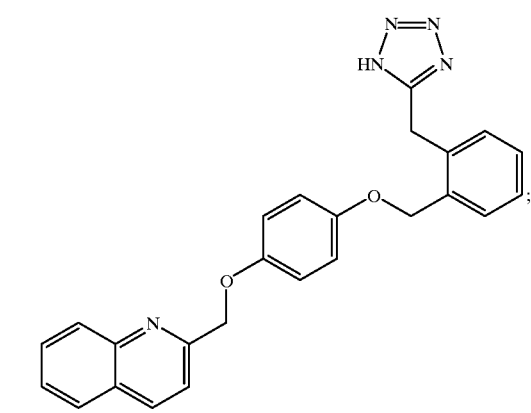

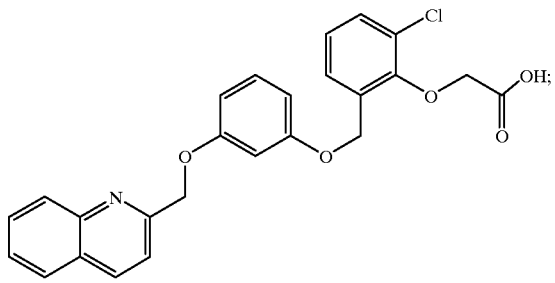

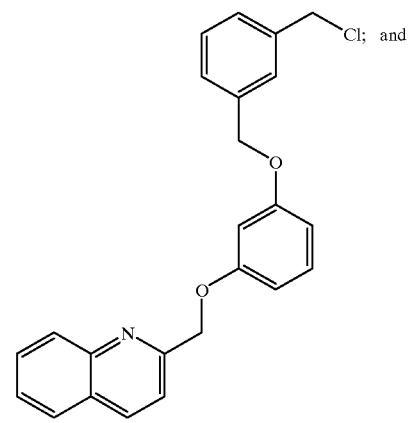

108

-continued or a pharmaceutically acceptable salt thereof.

15. The method according to claim 13 wherein the compound is of formula a pharmaceutically acceptable salt thereof.

16. The method according to claim 13 wherein the compound is of formula a pharmaceutically acceptable salt thereof.

17. The method according to claim 1, which further comprises administering a hypoglycemic agent.

18. The method according to claim 17, wherein the hypoglycemic agent is metformin.

* * * * *